(12) United States Patent
Bradner et al.

(10) Patent No.: US 9,789,120 B2
(45) Date of Patent: *Oct. 17, 2017

(54) MALE CONTRACEPTIVE COMPOSITIONS AND METHODS OF USE

(71) Applicants: Dana-Farber Cancer Institute, Inc., Boston, MA (US); Baylor College of Medicine, Houston, TX (US)

(72) Inventors: James Elliott Bradner, Cambridge, MA (US); Martin Matzuk, Houston, TX (US); Jun Qi, Sharon, MA (US)

(73) Assignees: Dana-Farber Cancer Institute, Inc., Boston, MA (US); Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/977,343

(22) Filed: Dec. 21, 2015

(65) Prior Publication Data

US 2016/0317547 A1  Nov. 3, 2016

Related U.S. Application Data

(63) Continuation of application No. 13/698,006, filed as application No. PCT/US2011/036667 on May 16, 2011, now Pat. No. 9,301,962.

(60) Provisional application No. 61/334,991, filed on May 14, 2010, provisional application No. 61/370,745, filed on Aug. 4, 2010, provisional application No. 61/375,863, filed on Aug. 22, 2010, provisional application No. 61/467,376, filed on Mar. 24, 2011, provisional application No. 61/467,299, filed on Mar. 24, 2011.

(51) Int. Cl.
| | | |
|---|---|---|
| *A01N 43/00* | (2006.01) | |
| *A61K 31/553* | (2006.01) | |
| *A61K 31/554* | (2006.01) | |
| *A61K 31/551* | (2006.01) | |
| *C07D 495/14* | (2006.01) | |
| *A61K 31/5517* | (2006.01) | |

(52) U.S. Cl.
CPC ........ *A61K 31/551* (2013.01); *A61K 31/5517* (2013.01); *C07D 495/14* (2013.01)

(58) Field of Classification Search
None
See application file for complete search history.

(56) References Cited

U.S. PATENT DOCUMENTS

| | | | |
|---|---|---|---|
| 3,681,343 A | 8/1972 | Hester, Jr. | |
| 3,709,898 A | 1/1973 | Hester, Jr. | |
| 3,812,259 A | 5/1974 | Collins | |
| 4,621,083 A | 11/1986 | Casals-Stenzel et al. | |
| 5,104,543 A | 4/1992 | Brandt et al. | |
| 5,593,988 A | 1/1997 | Tahara et al. | |
| 5,712,274 A * | 1/1998 | Sueoka ............... | C07D 495/14 514/219 |
| 5,721,231 A | 2/1998 | Moriwaki et al. | |
| 5,753,649 A | 5/1998 | Tahara et al. | |
| 5,760,032 A | 6/1998 | Kitajima et al. | |
| 5,846,972 A | 12/1998 | Buckman et al. | |
| 5,854,238 A | 12/1998 | Kempen | |
| 6,444,664 B1 | 9/2002 | Princen et al. | |
| 6,861,422 B2 | 3/2005 | Hoffmann et al. | |
| 7,015,213 B1 | 3/2006 | Bigg et al. | |
| 7,528,143 B2 | 5/2009 | Noronha et al. | |
| 7,528,153 B2 | 5/2009 | Noronha et al. | |
| 7,589,167 B2 | 9/2009 | Zhou et al. | |
| 7,750,152 B2 | 7/2010 | Hoffman et al. | |
| 7,786,299 B2 | 8/2010 | Hoffman et al. | |
| 7,816,530 B2 | 10/2010 | Grauert | |
| 7,825,246 B2 | 11/2010 | Noronha et al. | |
| 8,003,786 B2 | 8/2011 | Hoffman et al. | |
| 8,044,042 B2 * | 10/2011 | Adachi ............... | C07D 495/14 514/219 |
| 8,133,900 B2 | 3/2012 | Hood et al. | |
| 8,138,199 B2 | 3/2012 | Noronha et al. | |
| 8,338,464 B2 | 12/2012 | Melnick et al. | |
| 8,476,260 B2 | 7/2013 | Miyoshi et al. | |
| 8,604,042 B2 | 12/2013 | Noronha et al. | |
| 8,981,083 B2 | 3/2015 | Bradner et al. | |
| 9,301,962 B2 | 4/2016 | Bradner et al. | |
| 9,320,741 B2 | 4/2016 | Bradner et al. | |
| 2002/0032200 A1 | 3/2002 | Cai et al. | |
| 2002/0169158 A1 | 11/2002 | Hunt, III et al. | |
| 2003/0130268 A1 | 7/2003 | Sagara et al. | |
| 2003/0216758 A1 | 11/2003 | Signore | |
| 2004/0176380 A1 | 9/2004 | Hoffmann et al. | |
| 2006/0074088 A1 | 4/2006 | Munzert et al. | |
| 2006/0142257 A1 | 6/2006 | Nieschlag et al. | |
| 2006/0223055 A1 | 10/2006 | Howley et al. | |

(Continued)

FOREIGN PATENT DOCUMENTS

| | | |
|---|---|---|
| CA | 2020806 A1 | 1/1991 |
| CA | 2710740 A1 | 7/2009 |

(Continued)

OTHER PUBLICATIONS

International Search Report and Written Opinion for PCT/US2015/059622, mailed Mar. 30, 2016.
International Search Report and Written Opinion for PCT/US2015/059551, mailed Jan. 13, 2016.
International Search Report and Written Opinion for PCT/US2011/036667, mailed Aug. 15, 2011.
International Preliminary Report on Patentability for PCT/US2011/036667, mailed Nov. 29, 2012.
International Search Report and Written Opinion for PCT/US2011/036647, mailed Aug. 17, 2011.
International Preliminary Report on Patentability for PCT/US2011/036647, mailed Nov. 29, 2012.
International Search Report and Written Opinion for PCT/US2011/036701, mailed Feb. 1, 2012.
International Preliminary Report on PAtentability for PCT/US2011/036701, mailed Nov. 29, 2012.

(Continued)

*Primary Examiner* — Jared D Barsky
(74) *Attorney, Agent, or Firm* — Wolf, Greenfield & Sacks, P.C.

(57) ABSTRACT

The invention relates to compositions and methods for effecting male contraception.

26 Claims, 19 Drawing Sheets

(56) References Cited

U.S. PATENT DOCUMENTS

| | | |
|---|---|---|
| 2007/0105839 A1 | 5/2007 | Imbach et al. |
| 2007/0179178 A1 | 8/2007 | Buettelmann et al. |
| 2007/0218135 A1 | 9/2007 | Mukharya et al. |
| 2008/0004308 A1 | 1/2008 | Dhanak et al. |
| 2008/0081781 A1 | 4/2008 | Lippa et al. |
| 2008/0305113 A1 | 12/2008 | Kwon et al. |
| 2009/0012064 A1 | 1/2009 | Sagara et al. |
| 2009/0238828 A1 | 9/2009 | Munzert et al. |
| 2009/0280115 A1 | 11/2009 | Maier et al. |
| 2009/0281191 A1 | 11/2009 | Rangwala et al. |
| 2010/0041643 A1 | 2/2010 | Adachi et al. |
| 2010/0249412 A1 | 9/2010 | Linz et al. |
| 2010/0286127 A1 | 11/2010 | Miyoshi et al. |
| 2011/0028405 A1 | 2/2011 | Harrison et al. |
| 2011/0098288 A1 | 4/2011 | Major et al. |
| 2011/0172231 A1 | 7/2011 | Baenteli et al. |
| 2011/0201606 A1 | 8/2011 | Garcia-Cheverria et al. |
| 2011/0212077 A1 | 9/2011 | Noronha et al. |
| 2011/0245245 A1 | 10/2011 | Mortensen et al. |
| 2012/0014979 A1 | 1/2012 | Dent |
| 2012/0040961 A1 | 2/2012 | Gray et al. |
| 2012/0202798 A1 | 8/2012 | Sagara |
| 2012/0329803 A1 | 12/2012 | Guenter et al. |
| 2013/0184264 A1 | 7/2013 | Bradner et al. |
| 2013/0210813 A1 | 8/2013 | Bradner et al. |
| 2013/0245013 A1 | 9/2013 | Gangloff et al. |
| 2013/0252331 A1 | 9/2013 | Bradner et al. |
| 2013/0274239 A1 | 10/2013 | Arnold et al. |
| 2013/0280332 A1 | 10/2013 | Moss et al. |
| 2014/0011862 A1 | 1/2014 | Bradner et al. |
| 2014/0243322 A1 | 8/2014 | Arnold et al. |
| 2016/0033519 A1 | 2/2016 | Bradner et al. |
| 2016/0168154 A1 | 6/2016 | Bradner et al. |
| 2016/0231314 A1 | 8/2016 | Bradner et al. |
| 2016/0332993 A1 | 11/2016 | Bradner et al. |
| 2016/0347749 A1 | 12/2016 | Bradner et al. |
| 2017/0008895 A1 | 1/2017 | Bradner et al. |

FOREIGN PATENT DOCUMENTS

| | | |
|---|---|---|
| CH | 622019 A5 | 3/1981 |
| CN | 1227555 A | 9/1999 |
| CN | 103037865 A | 4/2013 |
| DE | 3724164 A1 | 2/1988 |
| EP | 0 087 850 A1 | 9/1983 |
| EP | 0 368 175 A1 | 5/1990 |
| EP | 0 387 613 A1 | 9/1990 |
| EP | 0 934 940 A1 | 8/1999 |
| EP | 0 989 131 A1 | 3/2000 |
| EP | 1 297 836 A1 | 4/2003 |
| EP | 2 239 264 A1 | 10/2010 |
| FR | 7532815 A1 | 5/1977 |
| FR | WO 2329668 | 5/1977 |
| JP | WO 61-87684 | 5/1986 |
| JP | 1-299231 | 12/1989 |
| JP | 6-157316 | 6/1994 |
| JP | H10500998 A | 1/1998 |
| JP | 11-228576 | 8/1999 |
| JP | WO 11-512107 | 10/1999 |
| JP | 3001979 | 11/1999 |
| JP | 3096299 | 8/2000 |
| JP | WO 2008-156311 | 7/2008 |
| JP | 5913292 B2 | 4/2016 |
| WO | WO 97/13537 | 4/1997 |
| WO | WO 97/37705 | 10/1997 |
| WO | WO 97/47622 A1 | 12/1997 |
| WO | WO 98/11111 A1 | 3/1998 |
| WO | WO 99/34850 | 7/1999 |
| WO | WO 01/95912 A1 | 12/2001 |
| WO | WO 2007/095188 | 8/2007 |
| WO | WO 2008/083056 A2 | 7/2008 |
| WO | WO 2008/137081 A1 | 11/2008 |
| WO | WO 2009/084693 | 7/2009 |
| WO | WO 2009/084693 A1 | 7/2009 |
| WO | WO 2010/015387 A1 | 2/2010 |
| WO | WO 2010/049466 A1 | 5/2010 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/143651 A1 | 11/2011 |
| WO | WO 2011/143657 A1 | 11/2011 |
| WO | WO 2011/143660 A2 | 11/2011 |
| WO | WO 2011/143669 A2 | 11/2011 |
| WO | WO 2011/161031 | 12/2011 |
| WO | WO 2012/075383 | 6/2012 |
| WO | WO 2012/075456 A1 | 6/2012 |
| WO | WO 2012/116170 | 8/2012 |
| WO | WO 2012/118812 A2 | 9/2012 |
| WO | WO 2013/033268 A2 | 3/2013 |
| WO | WO 2013/033269 A1 | 3/2013 |
| WO | WO 2013/033270 A2 | 3/2013 |
| WO | WO 2013/097601 | 7/2013 |
| WO | WO 2013/148197 A1 | 10/2013 |
| WO | WO 2014/071247 | 5/2014 |
| WO | WO 2015/081284 | 6/2015 |

OTHER PUBLICATIONS

International Search Report and Written Opinion for PCT/US2011/036672, mailed Jan. 27, 2012.

International Preliminary Report on Patentability for PCT/US2011/036672, mailed Nov. 29, 2012.

[No Author Listed], PubChem CID—55504609. Create date Jan. 25, 2012. https://pubchem.ncbi.nlm.nih.gov/compound/55504609. Last accessed Feb. 23, 2016.

[No Author Listed], PubChem CID—56267130. Create date Jan. 25, 2012. https://pubchem.ncbi.nlm.nih.gov/compound/56267130. Last accessed Feb. 23, 2016.

[No Author Listed], Methanesulfonyl chloride: Difference between revisions. Wikipedia entry. http://en.wikipedia.org/w/index.phptitle=Methanesulfonyl_chloride&diff=602110747&oldid=601684911. Last accessed Feb. 23, 2016. 2 pages.

Abbate et al., "Structure of the papillomavirus DNA-tethering complex E2:Brd4 and a peptide that ablates HPV chromosomal association," Mol Cell 24, 877-889, (2006).

Arango et al., "Reversible Azoospermia in a Patient Treated with Triazolam," Eur J Contracept Reprod Health Care, 1(3):293-294 (1996).

Berkovits et al., "The First Bromodomain of the Testis-Specific Double Bromodomain Protein Brdt is Required for Chromocenter Organization That is Modulated by Genetic Background," Dev Biol., 360(2):358-368 (2011).

Berkovits et al., "The Role of the Double Bromodomain-Containing BET Genes During Mammalian Spermatogenesis," Current Topics in Developmental Biology, 102: 293-326 (2013).

Buchdinger et al.,"Inhibition of the Abl Protein-Tyrosine Kinase In Vitro and In Vivo by a 2-Phenylaminopyrimidine Derivative," Cancer Res, 56:100-104 (1996).

Buchdinger et al., "Selective inhibition of the platelet-derived growth factor signal transduction pathway by a protein-tyrosine kinase inhibitor of the 2-phenylaminopyrimidine class," Proc Natl Acad Sci, 92:2558-2562 (1995).

Bullock et al., "Structural basis of Inhibitor Specificity of the Human Protooncogene Proviral Insertion site in Moloney Murine 1Leukemia virus (PIM-1) kinase," J Med Chem, 48:7604-7614 (2005).

Cellai et al., Mechanistic Insight Into WEB-2170-induced Apoptosis in Human Acute Myelogenous Leukemia Cells: the Crucial Role of PTEN, Exp Hematol, 37(10):1176-1185 (2009).

Cellai et al., Specific PAF Antagonist WEB-2086 Induces Terminal Differentiation of Murine and Human Leukemia Cells. FASEB, 16:733-735 (2002).

Cole, "Chemical probes for histone-modifying enzymes," Nat Chem Biol 4, 590-597 (2008).

Crawford et al., "Bromodomain 4 activation predicts breast cancer survival," Proc Natl Acad Sci, 105, 6380-6385, (2008).

(56) References Cited

OTHER PUBLICATIONS

Denis et al., "An Emerging Role for Bromodomain-Containing Proteins in Chromatin Regulation and Transcriptional Control of Adipogenesis," FEBS Lett., 584(15): 3260-3268 (2010).
Dey et al., "Brd4 Marks Select Genes of Mitotic Chromatin and Directs Postmitotic Transcription," Molecular Biology of the Cell, 20:4899-4909 (2009).
Druker et al, "Effects of a selective inhibitor of the Abl Tyrosine kinase on the Growth of Bcr-Abl positive cells," Nat Med, 2:561-566 (1996).
Druker et al., "Efficacy and safety of a specific inhibitor of the BCR-ABL tyrosine kinase in chronic myeloid leukemia," N Engl J Med 344, 1031-1037 (2001).
Fedorov et al.,"A Systematic Interaction Map of Validated Kinase Inhibitors with Ser/Thr kinases," Proc Natl Acad Sci., 104(51):20523-20528 (2007).
Filippakopoulos, "Selective Inhibition of BET Bromodomains," Nature, 468(7327): 1067-1073 (2010).
French et al.,"BRD4 Bromodomain Gene Rearrangement in Aggressive Carcinoma with Translocation t(15;19)," At J Pathol, 159(6):1987-1992 (2001).
French et al.,"BRD4-Nut Fusion Oncogene: a Novel Mechanism in Aggressive Carcinoma," Cancer Res, 63:304-307 (2003).
French et al., "BRD-NUT Oncoproteins: a Family of Closely Related Nuclear Proteins that Block Epithelial Differentiation and Maintain the Growth of Carcinoma Cells," Oncogene, 27:2237-2242 (2008).
French, "Demystified Molecular pathology of NUT Midline Carcinomas," J Clin Pathol, 63 :492-496 (2010).
Greenwald et al., "E.u-BRD2 Transgenic Mice Develop B-Cell Lymphoma and Leukemia," Blood, 103(4):1475-1484 (2004).
Haack et al., "Diagnosis ofNUT Midline Carcinoma Using a NUT-specific Monoclonal Antibody," At J Surg Pathol, 33:984-991 (2009).
He et al., The histone methyltransferase Ezh2 is a crucial epigenetic regulator of allogeneic T-cell responses mediating graft-versus-host disease. Blood. Dec. 12, 2013;122(25):4119-28. Doi: 10.1182/blood-2013-05-505180. Epub Oct. 18, 2013.
Houzelstein et al., Growth and early postimplantation defects in mice deficient for the bromodomain-containing protein Brd4. Mol Cell Biol. Jun. 2002;22(11):3794-802.
Hu et al., Adjudin targeting rabbit germ cell adhesion as a male contraceptive: a pharmacokinetics study. J Androl. Jan.-Feb. 2009;30(1):87-93. doi: 10.2164/jandrol.108.004994. Epub Sep. 18, 2008.
Huang et al., "Brd4 Coactivates Transcriptional Activation of NF-κB via Specific Binding to Acetylated RelA," Mol Cell Biol, 29(5):1375-1387 (2009).
Kadota et al., "Identification of Novel Gene Amplifications in Breast Cancer and Coexistence of Gene Amplification With an Activating Mutation of PIK3CA," Cancer Res, 69: 7357-7365 (2009).
Kim et al., "Berberine Improves Lipid Dysregulation in Obesity by Controlling Central and Peripheral AMPK Activity," At. J. Physiol. Endocrinol. Metab., 296: E812-E819 (2009).
Konze et al., An orally bioavailable chemical probe of the Lysine Methyltransferases EZH2 and EZH1. ACS Chem Biol. 2013;8(6):1324-34. Doi: 10.1021/cb400133j. Epub Apr. 24, 2013.
Lawless et al., Histone Deacetylase Inhibitors Target Diabetes Via Chromatin Remodeling or as Chemical Chaperones? Curr Diabetes Rev, 5(3):201-209 (2009).
Le Coutre et al., In vivo eradication of human BCR/ABL-positive leukemia cells with an ABL kinase inhibitor. J Natl Cancer Inst, 91:163-168 (1999).
Lee et al., "Berberine, a Natural Plant Product, Activates AMP-Activated Protein Kinase with Beneficial Metabolic Effects in Diabetic and Insulin-Resistant States," Diabetes, 55: 2256-2264 (2006).
Marushige, Activation of Chromatin by Acetylation of Histone Side Chains, Proc. Nat'l. Acad. Sci., 73(11): 3937-3941 (1976).

Matzuk, "Small-Molecule Inhibition of BRDT for Male Contraception," Cell: 150: 673-684 (2012).
Meguro et al., "Heterocycles. VI. Synthesis of 4H-s-Triazolo[4,3-a][1,4]benzodiazepines, Novel Tricyclic Psychosedatives," Chem. Pharm. Bull., 21(11):2382-2390 (1973).
Men-Ger et al., "Use of All-Trans Retinoic Acid in the Treatment of Acute Promyelocytic Leukemia," Blood, 72(2): 567-572 (1988).
Mochizuki et al., "The Bromodomain Protein Brd4 Stimulates G1 Gene Transcription and Promotes Progression to S Phase," J Biol Chem, 283(14):9040-9048 (2008).
Niesen et al., "The use of Differential Scanning Fluorimetry to Detect Ligand Interactions that Promote Protein Stability," Nat Protoc, 2(9):2212-2221 (2007).
Nishimura et al., Fertility and Reproduction Studies of Apafant (WEB 2086 BS) in Rats Dosed Orally. Oyo Yakuri/Pharmacometrics. Oct. 1, 1996. 52(3/4):185-200.
Owen et al., "The Structural Basis for the Recognition of Acetylated Histone R4 by the Bromodomain of Histone Acetyltransferase Gcn5p," The EMBO Journal, 19(22): 6141-6149 (2000).
Patani et al., "Bioisosterism: A Rational Approach in Drug Design," Chem. Rev., 96:3147-3176 (1996).
Phelps et al., "Clinical Response and Pharmacokinetics :from a Phase 1 Study of an Active Dosing Schedule ofFlavopiridol in Relapsed Chronic Lymphocytic Leukemia," Blood, 113(12):2637-2645 (2009).
Presiler et al., "Assessment of c-myc Expression in Individual Leukemic Cells," Leuk Res, 12(6): 507-516 (1988).
Ptashne, "Binding Reactions: Epigenetic Switches, Signal Transduction and Cancer," Current Biology, 19(6):R234-R241 (2009).
Quinn et al.,"A homogeneous method for investigation of methylation-dependent protein-protein interactions in epigenetics," Nucleic Acids Res, 38(2):el 1(1-10) (2010).
Rahl et al., "c-Myc Regulates Transcriptional Pause Release," Cell, 141 :432-445 (2010).
Santillan et al., "Bromodomain and Histone Acetyltransferase Domain Specificities Control Mixed Lineage Leukemia Phenotype," Cancer Res, 66(20):10032-10039 (2006).
Schindler et al., "Structural mechanism for STI-571 Inhibition of Abelson Tyrosine kinase. Science, "289:1938-1942 (2000).
Schreiber et al., "Signaling Network Model of Chromatin," Cell, 111:771-778 (2002).
Seyrig et al., "Effects of a Chronic Administration ofTwo Benzodiazepines on Food Intake in Rats Given a Highly Palatable Diet," Pharmacology Biochemistl y & BehT;ior, 25:913-918 (1986).
Shang et al., "The First Bromodomain of Brdt, a Testis-Specific Member of the BET Sub-Family of Double-Bromodomain-Containing Proteins, is Essential for Male Germ Cell Differentiation," Development, 134: 3507-3515 (2007).
Taskinen et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin Cancer Res, 13(19): 5784-5785 (2007).
Verma et al., Identification of Potent, Selective, Cell-Active Inhibitors of the Histone Lysine Methyltransferase EZH2. ACS Med Chem Lett. Oct. 19, 2012;3(12):1091-6. Doi: 10.1021/m13003346. eCollection 2012.
Vollmuth et al., "Structures of the dual bromodomains of the P-TEFb-activating protein Brd4 at atomic resolution," J Biol Chem, 284:36547-36556 (2009).
Von Voigtlander et al.,"Alprazolam: Review of Pharmacological, Pharmacokinetic and Clinical Data," Drug Development Research, 6:1-12 (1985).
Wang et al., "Brd2 Disruption in Mice Causes Severe Obesity Without Type 2 Diabetes," Biochem. J., 425:71-83 (2010).
Wang et al., A seamless trespass: germ cell migration across the seminiferous epithelium during spermatogenesis. J Cell Biol. Aug. 13, 2007;178(4):549-56.
Yang et al., "Brd4 recruits P-TEFb to chromosomes at late mitosis to promote G1 gene expression and cell cycle progression," Mol Cell Biol, 28(3):967-976 (2008).

(56) References Cited

OTHER PUBLICATIONS

Yang et al., "Multisite Protein Modification and Intramolecular Signaling," Oncogene, 24:1653-1662 (2005).
Yang et al., "Recruitment of P-TEFb for Stimulation of Transcriptional Elongation by the Bromodomain Protein Brd4," Molecular Cell, 16:535-545 (2005).
You et al., "Kaposi's sarcoma-associated herpesvirus latency-associated nuclear antigen interacts with bromodomain protein Brd4 on host mitotic chromosomes," J Virol 80, 8909-8919, (2006).
You et al., "Regulation of Aurora B Expression by the Bromodomain Protein Brd4," Mol Cell Biol, 29:5094-5103 (2009).
Zeng et al., "Bromodomain: an Acetyl-lysine Binding Domain," FEBS Letters, 513:124-128 (2002).
Zhang et al., "Down-Regulation of NF-κB Transcriptional Activity in HIV-Associated Kidney Disease by BRD4 Inhibition," J. Biol Chem, 287(34):28840-28851 (2012).
Zhang et al., "Down-Regulation of NF-κB Transcriptional Activity in HIV-Associated Kidney Disease by BRD4 Inhibition," J. Biol Chem, 287(46):38956 (2012).
Zhao et al., "Research Development on Fusion Protein Transcription Factor siRNA Specifically Targeting Leukemia," Sciencepaper• Online: 1-6 and J. J Med Res ., 39(2):6-9 (Feb. 2010) (English-language translation entitled "Progiess ofResearch on siRNA that Targets Leukemia Specific Transcription Regulation Factor Fusion Proteins," pp. 1-10).
Zuber et al.,"RNAi Screen Identifies Brd4 as a Therapeutic Target in Acute Myeloid Leukaemia," Nature: 478: 524-528 (2011), with "Supplementary Information" from www.nature.com/nature, pp. 1-33.
International Search Report and Written Opinion for PCT/US2014/023386, dated Jul. 9, 2014.
International Preliminary Report on Patentability for PCT/US2014/023386, dated Sep. 24, 2015.
Extended European Search Report for PCT/US2014/048230, dated Jan. 31, 2017.
Invitation to Pay Additional Fees for PCT/US2014/48230, dated Nov. 17, 2014.
International Search Report and Written Opinion for PCT/US2014/48230, dated Jan. 30, 2015.
International Preliminary Report on Patentability for PCT/US2014/48230, dated Feb. 4, 2016.
Invitation to Pay Additional Fees for PCT/US2015/14109, dated Apr. 20, 2015.
International Search Report and Written Opinion for PCT/US2015/14109, dated Jul. 6, 2015.
International Preliminary Report on Patentability for PCT/US2015/14109, dated Aug. 11, 2016.
International Search Report and Written Opinion for PCT/US2015/14044, dated Apr. 23, 2015.
International Preliminary Report on Patentability for PCT/US2015/14044, dated Aug. 11, 2016.
International Search Report and Written Opinion for PCT/US2015/14039, dated Apr. 23, 2015.
International Preliminary Report on Patentability for PCT/US2015/14039, dated Aug. 11, 2016.
International Search Report and Written Opinion for PCT/US2015/14120, dated Apr. 23, 2015.
International Preliminary Report on Patentability for PCT/US2015/14120, dated Aug. 11, 2016.
International Search Report and Written Opinion for PCT/US2015/044180, dated Nov. 5, 2015.
International Preliminary Report on Patentability for PCT/US2015/044180, dated Feb. 23, 2017.
Invitation to Pay Additional Fees for PCT/US2015/044303, dated Oct. 21, 2015.
International Search Report and Written Opinion for PCT/US2015/044303, dated Dec. 31, 2015.
International Preliminary Report on Patentability for PCT/US2015/044303, dated Feb. 23, 2017.
Invitation to Pay Additional Fees for PCT/US2016/051017, dated Oct. 31, 2016.
International Search Report and Written Opinion for PCT/US2016/051017, dated Jan. 10, 2017.
International Search Report and Written Opinion for PCT/US2016051107, dated Nov. 22, 2016.
Invitation to Pay Additional Fees for PCT/US2016/63502, dated Feb. 9, 2017.
Genbank Submission; NH/NCBI, Accession No. H86170. Hillier et al., Nov. 15, 1995. 2 pages.
Genbank Submission; NH/NCBI, Accession No. NP_001003694. Lubula et al., Oct. 6, 2016. 4 pages.
Genbank Submission; NH/NCBI, Accession No. NP_001420. Ledsaak et al., Sep. 15, 2016. 8 pages.
Genbank Submission; NH/NCBI, Accession No. NP_001717. Barda et al., Feb. 2, 2014. 2 pages.
Genbank Submission; NH/NCBI, Accession No. NP_003061. Agaimy et al., Dec. 10, 2016. 5 pages.
Genbank Submission; NH/NCBI, Accession No. NP_003063. Liao et al., May 2, 2016. 5 pages.
Genbank Submission; NH/NCBI, Accession No. NP_003843. Yuan et al., Dec. 20, 2003. 3 pages.
Genbank Submission; NH/NCBI, Accession No. NP_003875. Li et al., Oct. 7, 2016. 3 pages.
Genbank Submission; NH/NCBI, Accession No. NP_004371. Liu et al., Dec. 10, 2006. 3 pages.
Genbank Submission; NH/NCBI, Accession No. NP_004597. Herzfeld et al., Aug. 26, 2016. 5 pages.
Genbank Submission; NH/NCBI, Accession No. NP_005095. Xiao et al., Oct. 6, 2016. 4 pages.
Genbank Submission; NH/NCBI, Accession No. NP_005753. Dalgaard et al., Oct. 6, 2016. 6 pages.
Genbank Submission; NH/NCBI, Accession No. NP_009168. DiBernardo et al., Sep. 28, 2008. 2 pages.
Genbank Submission; NH/NCBI, Accession No. NP_031397. Shao et al., Jan. 4, 2017. 4 pages.
Genbank Submission; NH/NCBI, Accession No. NP_038478. Jones et al., Sep. 23, 2005. 2 pages.
Genbank Submission; NH/NCBI, Accession No. NP_054828. Hou et al., Sep. 15, 2016. 5 pages.
Genbank Submission; NH/NCBI, Accession No. NP_055392. Aberg et al., Mar. 22, 2014. 3 pages.
Genbank Submission; NH/NCBI, Accession No. NP_060404. Bezrookove et al., Oct. 7, 2016. 5 pages.
Genbank Submission; NH/NCBI, Accession No. NP_060635. Varela et al., Dec. 18, 2011. 3 pages.
Genbank Submission; NH/NCBI, Accession No. NP_060959. Kuryshev et al., Mar. 26, 2006. 2 pages.
Genbank Submission; NH/NCBI, Accession No. NP_061836. Perry et al. , Feb. 21, 2016. 7 pages.
Genbank Submission; NH/NCBI, Accession No. NP_066564. Wiper-Bergeron et al., Jun. 3, 2007. 3 pages.
Genbank Submission; NH/NCBI, Accession No. NP_076413. Clark et al., Jun. 27, 2007. 2 pages.
Genbank Submission; NH/NCBI, Accession No. NP_113601. Knijnenburg et al., Jan. 17, 2014. 3 pages.
Genbank Submission; NH/NCBI, Accession No. NP_490597. Duan et al., Oct. 6, 2016. 5 pages.
Genbank Submission; NH/NCBI, Accession No. NP_612411. Saare et al., Aug. 25, 2016. 2 pages.
Genbank Submission; NH/NCBI, Accession No. NP_722516. Xia et al., Nov. 22, 2015. 3 pages.
Genbank Submission; NH/NCBI, Accession No. NP_872579. Lee et al., Oct. 6, 2016. 4 pages.
Genbank Submission; NH/NCBI, Accession No. XP_039676. [No Author Listed], Aug. 19, 2004. 3 pages.
[No Author Listed], PubChem CID 5325760. Published Jan. 25, 2006. pubchem.ncbi.nlm.nih/gov//compound/5325760?from=summary#section=Top. Last accessed Oct. 20, 2014.
[No Author Listed], PubChem SID 225027960. Available date/deposit date: Feb. 2, 2015. pubchem.ncbi.nlm.nih.gov/substance/225027960. Last accessed Nov. 28, 2016.

(56) References Cited

OTHER PUBLICATIONS

[No Author Listed], PubChem SID 235048169. Feb. 13, 2015. Retrieved on Oct. 24, 2016. Available at https://pubchem.ncbi.nlm.nih.gov/substance/235048169.

[No Author Listed], PubChem SID 235671906. Feb. 13, 2015. Retrieved on Oct. 24, 2016. Available at https://pubchem.ncbi.nlm.nih.gov/substance/235671906#section=Top>.

Anders et al., Genome-wide localization of small molecules. Nat Biotechnol. Jan. 2014;32(1):92-6. doi: 10.1038/nbt.2776. Epub Dec. 15 2013.

Bartholomeeusen et al., Bromodomain and extra-terminal (BET) bromodomain inhibition activate transcription via transient release of positive transcription elongation factor b (P-TEFb) from 7SK small nuclear ribonucleoprotein. J Biol Chem. Oct. 19, 2012;287(43):36609-16. doi: 10.1074/jbc.M112.410746. Epub Sep. 5, 2012.

Baud et al., Chemical biology. A bump-and-hole approach to engineer controlled selectivity of Bet bromodomain chemical probes. Science. Oct. 31, 2014;346(6209):638-41. doi: 10.1126/science.1249830. Epub Oct. 16, 2014.

Berge et al., Pharmaceutical salts. J Pharm Sci. Jan. 1977;66(1):1-19.

CAPLUS Database Result for Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013. Accession No. 2013:1979798. Abstract Only.

Chaidos et al., Potent antimyeloma activity of the novel bromodomain inhibitors I-BET151 and I-BET762. Blood. Jan. 30, 2014;123(5):697-705. doi: 10.1182/blood-2013-01-478420. Epub Dec. 13, 2013.

Cheng et al., Adjudin disrupts spermatogenesis via the action of some unlikely partners: Eps8, Arp2/3 complex, drebrin E, PAR6 and 14-3-3. Spermatogenesis. Oct. 2011;1(4):291-297. Epub Oct. 1, 2011.

Choi et al., Brain Penetrant LRRK2 Inhibitor. ACS Med Chem Lett. Aug. 9, 2012;3(8):658-662.

Dawson et al., Inhibition of BET recruitment to chromatin as an effective treatment for MLL-fusion leukaemia. Nature. Oct. 2, 2011;478(7370):529-33. doi: 10.1038/nature10509.

Delbroek et al., Development of an enzyme-linked immunosorbent assay for detection of cellular and in vivo LRRK2 S935 phosphorylation. J Pharm Biomed Anal. Mar. 25, 2013;76:49-58.

Delmore et al., BET bromodomain inhibition as a therapeutic strategy to target c-Myc. Cell. Sep. 16, 2011;146(6):904-17. doi: 10.1016/j.cell.2011.08.017. Epub Sep. 1, 2011.

Deng et al., Characterization of a selective inhibitor of the Parkinson's disease kinase LRRK2. Nat Chem Biol. Apr. 2011;7(4):203-5.

Deng et al., Discovery of a benzo[e]pyrimido-[5,4-b][1,4]diazepin-6(11H)-one as a Potent and Selective Inhibitor of Big MAP Kinase 1. ACS Med Chem Lett. Mar. 10, 2011;2(3):195-200.

Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67.

Elkins et al., X-ray crystal structure of ERK5 (MAPK7) in complex with a specific inhibitor. J Med Chem. Jun. 13, 2013;56(11):4413-21.

Filippakopoulos et al., Targeting bromodomains: epigenetic readers of lysine acetylation. Nat Rev Drug Discov. May 2014;13(5):337-56. doi: 10.1038/nrd4286. Epub Apr. 22, 2014.

Kavanagh et al., the development of CNS-active LRRK2 inhibitors using property-directed optimisation.Bioorg Med Chem Lett. Jul. 1, 2013;23(13):3690-6.

Krueger et al., The mechanism of release of P-TEFb and HEXIM1 from the 7SK snRNP by viral and cellular activators includes a conformational change in 7SK. PLoS One. Aug. 23, 2010;5(8):e12335. doi: 10.1371/journal.pone.0012335.

Lotti et al., Ultrasound of the male genital tract in relation to male reproductive health. Hum Reprod Update. Jan.-Feb. 2015;21(1):56-83. doi: 10.1093/humupd/dmu042. Epub Jul. 19, 2014.

Mckeown et al., Biased multicomponent reactions to develop novel bromodomain inhibitors. J Med Chem. Nov. 13, 2014;57(21):9019-27. doi: 10.1021/jm501120z. Epub Oct. 31, 2014.

Roberts et al., A Bead-Based Proximity Assay for BRD4 Ligand Discovery. Curr Protoc Chem Biol. Dec. 2, 2015;7(4):263-78. doi: 10.1002/9780470559277.ch150024.

Schroder et al., Two-pronged binding with bromodomain-containing protein 4 liberates positive transcription elongation factor b from inactive ribonucleoprotein complexes. J Biol Chem. Jan. 6, 2012;287(2):1090-9. doi: 10.1074/jbc.M111.282855. Epub Nov. 14, 2011.

Smith et al., The Bromodomain: A New Target in Emerging Epigenetic Medicine. ACS Chem Biol. Mar. 18, 2016;11(3):598-608. doi: 10.1021/acschembio.5b00831. Epub Dec. 3, 2015.

Tanaka et al., Inhibitors of emerging epigenetic targets for cancer therapy: a patent review (2010-2014). Pharm Pat Anal. 2015;4(4):261-84. doi: 10.4155/ppa.15.16.

Wehner et al., Effects of natalizumab, an alpha4 integrin inhibitor, on fertility in male and female guinea pigs. Birth Defects Res B Dev Reprod Toxicol. Apr. 2009;86(2):108-16. doi: 10.1002/bdrb.20191.

Zuercher et al., Identification and structure-activity relationship of phenolic acyl hydrazones as selective agonists for the estrogen-related orphan nuclear receptors ERRbeta and ERRgamma.. J Med Chem. May 5, 2005;48(9):3107-9.

\* cited by examiner (+)-JQ1

FIG. 3

```
BRDT  M--------------------------------------SLPSRQTAIVNPPPEYINTKKNGRLT
BRD4  MSAESGPGTRLRNLPVMGDGLETSQMSTTQAQAQPQPANAASTNPPPETSNPNKPKRQT
                                             *   .* .******  *.:. *

BRDT  NQLQYLQKVVLKDLWKHSFSWPFQRPVDAVKLQLPDVYTIIKNPMDLNTIKKRLENKYYA
BRD4  NQLQYLLRVVLKTLWKHQFAWPFQQPVDAVKLNLPDYYKIIKTPMDMGTIKKRLENNYYW
      ****** :*** ******.**:****:***** ***.:  :* :***,*.* ** . **

BRDT  KASECIEDFNTMFESNCYLYNKPGDDIVLMAQALEKLFMQKLSQMPQEEQVVGVKERIKKG
BRD4  NAQECIQDFNTMFTNCYIYNKPGDDIVLMAEALEKLFLQKINELPTETETEIMIVQAKGRG
       *.****:******:.**:***********:*****:**:.:  . *:*: :.::..:*

BRDT  ---------------------------TQQNIAVSSAKEKSSPSATEKVFKQQEIPS
BRD4  RGRKETGTAKPGVSTVPNTTQASTPPQCTQTPQPNPPPVQATPHPPAVTPDLIVQTPVMT
                                  . *  .: .:. *  .: *:

BRDT  VFPKTSI----------------SPLNVVQGASVNSSSQTAAQVTKGVKRKADTTPAT--
BRD4  VVPPQPLQTPPPVPPQPQPPPAPQPPAPAPQPVQSHPPIIAATPQPVKTKKGVKRKADTTPTTI
      * *                    . *    :      ::      * ..:*:**********:*

BRDT  SAVKASSEFSP-------TFTEKSVALPPIKENMPKNVLPDSQQQYNVKTVKVTEQLRHCS
BRD4  DPIHEPPSLPPEPKTTKLGQRRESSRPVKP----PKKDVPDSQQHPAPEKSSKVSEQLKCCS
      .:  ::. *.: :: *  ;* ;* *::*** :   * ***;:*..;
```

FIG. 3 (continued)

```
BRDT  EILKEMLAKKHFSYAWPFYNPVDVNALGLHNYYDVVKNPMDLGTIKEKMDNQEVKDAYKF
BRD4  GILKEMFAKKHAAYAWPFYKPVDVEALGLHDYCDIITKHPMDMSTIKSKLEAREYRDAQEF
      .******:****:***.********:***:*****:**  ** ****:.****.:*:.:.:*

BRDT  AADVRLMFMNCYKYNPPDHEVVTMARMLQDVFETHFSKIPIEPVE------SMPLCYIKTD
BRD4  GADVRLMFSNCYKYNPPDHEVVAMARKLQDVFEMRFAKMPDEPEEPVVAVSSPAVPPPTK
      .*******:***********:***:****** *:*.:**:**:   *         *

BRDT  ITE--TTGRENTNEASSEGNSSDDSEDERVKRLAKLQEQLKAVHQQLQVLSQVPFRKLNK
BRD4  VVAPPSSSDSSSDSSSDSDSSTDDSEEERAQRLAELQEQLKAVHEQLAALSQ-PQQNKPK
      :*  ::*.::::*::******:****:*********::****.***  * *:

BRDT  KKEKSKKEKKKEKVNNSNENPRKMCEQMRLKEKSKRNQPKKRKQQFIG------------
BRD4  KKEKDKKEKKKEK-------HKRKEEVEENKKSKAKEPPPKKTKKNNSSNSNVSKKEPAPM
      ****.********       :.***:.::*: .** .* **:.

BRDT  ---------LKSEDEDNAKPMNYDEKRQLSLNINKLPGDKLGRVVHIIQSREPSLSNSNPDE
BRD4  KSKFPPTYESEEEDRCKPMSYEEKRQLSLDINKLPGEKLGRVVHIIQSREPSLKNSNPDE
              :*:**:  :***.*:*******:******:*******************.*****

BRDT  IEIDFETLKASTLRELEKYVSACLRKRPLKPPAKKTMMSKEELHSQKKQELEKRLLDVNN
BRD4  IEIDFETLKPSTLRELERYVTSCLRKK--RKPQAEKV-----------------DV----
      ********* ******* ***::****    **. *:*                 *:
```

FIG. 3 (continued)

```
BRDT  QLNSRKRQTKSDKTQPSKAVENVSRLSESSSSSSSSESESSSSDLSSSDSSSDSESEMFP
BRD4  ----------------------------TAGSSKMKGFSSSESESSES-SSSDSEDSETEMAP
                                  .*,   .   **********,  *****, ***,:** *

BRDT  K--------------------------------------------------------
BRD4  KSKKKGHPGREQKKHHHHHHHQQMQQAPAPVPQQPPPPPQQPPPPPQQQQQPPPPPPP
      *

BRDT  ------------------------------------------------FTE------
BRD4  SMPQQAAPAMKSSPPPFIATQVPVLEPQLPGSVFDPIGHFTQPILHLPQPELPPHLPQPP
                                                      **;

BRDT  ---------------------------------------------------------
BRD4  EHSTPPHLNQHAVVSPPPALHNALPQQPSRPSNRAAALPPKPARPPAVSPALTQTPLLPQP

BRDT  ------------------------------VKP------------------------
BRD4  PMAQPPQVLLEDEEPPAPPLTSMQMQLYLQQLQKVQPPTPLLPSVKVQSQPPPPLPPPPH
                                    *;*

BRDT  ---------------------------------------------------------
BRD4  PSVQQQLQQQPPPPPPPPPQPOPPPQQQHQPPPRPVHLQPMQFSTHIQQPPPPQGQQPPHPP
```

FIG. 3 (continued)

```
BRDT   ------------------------------------------------------------NDS
BRD4   PGQQPPPPPQPAKPQQVIQHHKSPRHHKSDPYSTGHLREAPSPLMIHSPQMSQFQSLTHQS
                                                                   ::*

BRDT   PSKENVKKMKNECIPPEGRTGVTQIGYCVQDTTSANTTLVHQTTPSHVMPPNHHQLAFNY
BRD4   PPQQNVQPKKQEL---RAASVVQPQPLVVVKEEKIHSPIIRSEPFSPSLRPEPPKHPESI
       *.:;**;   *  *  . :**:**:.     *   ;;;:::;  *     ;:  .

BRDT   QELEHLQTVKNISPLQ------ILPPSGDSEQLSNGITVMHPSGDSDTTMLESECQAPV--
BRD4   KAPVHLPQRPEMKPVDVGRPVIRPPEQNAP--------PPGAPDKDKQKQEPKTPVAP
       : **  . :*. *  :   .  :*  *             *.* *  * :  : :**

BRDT   QKDIKIRNADSWKSL--GKPVRPSGVMKSSDELFNQFRKAATEKEVKAPTQELIRKHLEQ
BRD4   KKDLKIKNMGSWASLVQKHPTTPSSTAKSSSDSFEQFRRAAREKEEREKALKAQAEHAEK
       :**:**:*  **.**   * .   *.:*** ** :****:** **:* ::::** ***

BRDT   NTKELKASQENQRDLGNGLTV--------ESPSNKIQNKCSGEEQKEHQQSSEA------
BRD4   EKERLRQERMRSREDEDALEQARRAHEEARRRQEQQQQRQEQQQQQQAAAVAAAATP
       :.*:*: :*.*  : :*.* .          *: .    .:* *** :*...      *

BRDT   ---QDKSKLWLLKDRDLARQKEQERPRREAMVGTIDMTLQSDIMTMFENNFD
BRD4   QAQSSQPQSMLDQQRELARKREQERRREAMAATIDMNFQSDLLSIFEENLF
          .. : ::::** *:*** :****:*****. ***:. ***::: **:* :
```

FIG. 4

```
hBRDT  MSLPSRQTAIIVNPPPPEYINTKKNGRLTNQLQYLQKVVLKDLWKHSFSWPFQRPVDAVK
mBRDT  MSLPSRQTA-IVNPPPPEYINTKKKSGRLTNQLQFLQRVVLKALWKHGFSWPFQQPVDAVK
       ******* ********** :**:*:**** *.********* hBRDT  LQLPDYYTIIKNPMDLNTIKKRLENKYYAKASECIEDFNTMFSNCYLYNKPGDDIVLMAQ
mBRDT  LKLPDYYTIIKTPMDLNTIKKRLENKYYEKASECIEDFNTMFSNCYLYNKTGDDIVVMAQ
       *:******. **********: ****************:*:* hBRDT  ALEKLFMQKLSQMPQEEQVVGVKERIKKGTQQNIAVSSAKEKSSPSATERVEKQQEIPSV
mBRDT  ALEKLFMQKLSQMPQEEQVVGGKERIKKDIQQKIAVSSAKEQIPSKAAENVFKRQEIPSG
       ******************.***  :********:  *:* *.* *:***** hBRDT  FPKTSISPLNVVQGASVNSSSQTAAQVTKGVKRKADTTTPATSAVKASSEFSPTFTEKSV
mBRDT  LPDISLSPLNMAQEAPPICDSQSLVQITKGVKRRADTTTPTTSIAKASSESPPTLRETKP
       :* :* ****:.*.:.  . **: .:********:******:** ***** *.*:*:*.

hBRDT  ALPPIKENMPKNVLPDSQQQYNVVKTVKVTEQLRHCSEILKEMLAKKHFSYAWPFYNPVD
mBRDT  VNMPVKENTVKNVLPDSQQQHKVLKTVKVTEQLKHCSEILKEMLAKKHLPYAWPFYNPVD
       . .*:*** .**********::*:*********:**************  *********
```

FIG. 4 (continued)

```
hBRDT  VNALGLHNYYDVVKNPMDLGTIKEKMDNQEYKDAYKFAADVRLMFMNCYKYNPPDHEVVT
mBRDT  ADALGLHNYYDVVKNPMDLGTIKGKMDNQEYKDAYEFAADVRLMFTMNCYKYNPPDHEVVA
       .:************* ************.*****.:****************:*****;

hBRDT  MARMLQDVFETHFSKIPIEPVESMPLCYIKTDITETTGRENTNEASSEGNSSDDSEDERV
mBRDT  MARTLQDVFELHFAKIPDEPIESMHACHLTTNSAQALSRESSSEASSGDASSEDSEDERV
       *.**.:::. * :*..*  ****..*.  **.:****** hBRDT  KRLAKLQEQLKAVHQQLQVLSQVPFRKLNKKKEKSKKEKKKEKVNNSNENPRKMCEQMRL
mBRDT  QHLAKLQEQLNAVHQQLQVLSQVPLRKLKKKNEKSKRAPKRKKVNNRDENPRKKPKQMKQ
       :.********.************ ***.**:****:. *:** *** .***** ::*:;

hBRDT  KEKSKRNQPKRKQFIGLKSEDEDNAKPMNYDEKRQLSLNINKLPGDKLGRVVHIIQSR
mBRDT  KEKAKINQPKKKKPL---LKSEEEDNAKPMNYDEKRQLSLDINKLPGDKLGRTVHIIQSR
       ***:*:*:.    **:*********** :******.**** hBRDT  EPSLSNSNPDEIEIDFETLKASTLRELEKYVSACLRKRPLKPPAKKIMSKEELHSQKKQ
mBRDT  EPSIRNSNPDEIEIDFETLKASTLRELEKYVLACLRKRSLKPQAKKVVRSKEELHSEKKL
       ***: ************************** *****.***.***:: **:**** **

hBRDT  ELEKRLLDVNNQLNSRKRQTK-----------------SDKTQPSKA
mBRDT  ELERRLLDVNNQLNCRKRQTKRPAKVEKPPPPPPPPPPPPELASGSRLTDSSSSSGS
       ***:**********.*****                   *:.:..: :
```

FIG. 4 (continued)

```
hBRDT  VENVSRLSESSSSSSSSSSESESSSSDLSSSDSSDSESEMFPKFTEVKPNDSPSKENVKKM
mBRDT  GSGSSSSSGSSSSSSSSSSGSASSSSDSSSSSSDSSDFEPEIFPKFTGVKQNDLPPKENIK---
       . *  ********  *.*  *****  ** ** ****** **.* :

hBRDT  KNECTPPEGRTGVTQIGYCVQDTTSANTTLVHQTTPSHVMPPNHHQLAFNYQELEHLQTV
mBRDT  ---------QIQSSVQDITSAEAPLAQQSTAPCGAPGKHSQQMLGCQVTQHLQAT
                *  ***  :*:.*:.    . *       :***:  * :***;:

hBRDT  KNISPLQILPPSGDSEQLSNGITVMHPSGDSDTTMLESECQAPVQKDIKIKNADSWKSLG
mBRDT  ENTASVQTQPLSGDCKRVLLGPPVVHTSAES-LTVLEPECHAPAQKDIKIKNADSWKSLG
       .*  : :.*  *     * :: :  *   *.*   *.***..************ hBRDT  KPVKPSGVMKSSDELFNQFRKAATEKEVKARTQELIRKHLEQNTKELKASQENQRDLGNG
mBRDT  KPVKASSVLKSSDELFNQFRKAATEKEVKARTQEQMRKHLEHNAKDPKVSQENQREPGSG
       **** *.*:***************** *:* :**.*  :  .:*******:  .* hBRDT  LTVESFSNKIQNKCSGEEQKEHQQSSEAQDKSKLWLLKDRDLARQKEQERRRREAMVGTI
mBRDT  LTLESLSSKVQDKSLEEDQSEQQPPSEAQDVSKLWLLKDRNLAREKEQERRRREAMAGTI
       ::*.*:*:*  *  : .:  .  * .********.::********* * hBRDT  DMTLQSDIMTMFENNFD
mBRDT  DMTLQSDIMTMFENNFD
       *****************
```

FIG. 8C
Vehicle
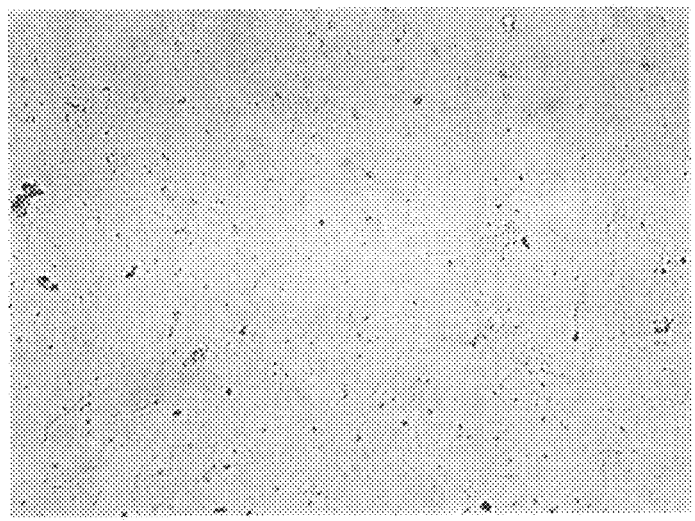
(+)-JQ1 50 mpk 8 weeks)

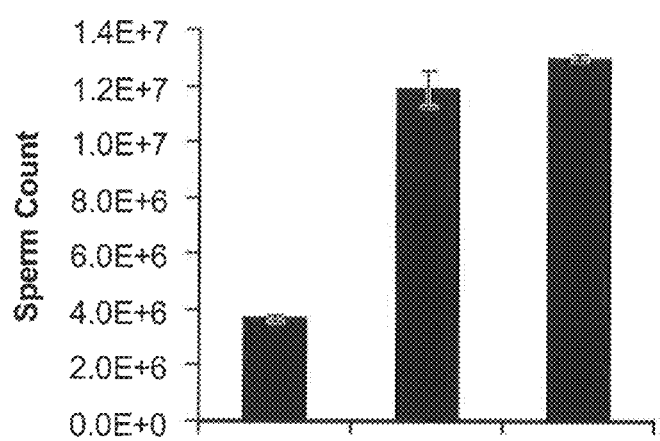

MALE CONTRACEPTIVE COMPOSITIONS AND METHODS OF USE

CROSS-REFERENCE TO RELATED APPLICATION

This application is a continuation of U.S. application Ser. No. 13/698,006, which is the U.S. National Stage of International Application No. PCT/US2011/036667, filed on May 16, 2011, published in English, which claims the benefit of U.S. Provisional Application No. 61/334,991, filed May 14, 2010; 61/370,745, filed on Aug. 4, 2010; 61/375,863, filed on Aug. 22, 2010; 61/467,376, filed on Mar. 24, 2011; and 61/467,299, filed Mar. 24, 2011. The contents of these applications are hereby incorporated by reference in their entirety.

STATEMENT OF RIGHTS TO INVENTIONS MADE UNDER FEDERALLY SPONSORED RESEARCH

This work was supported by the following grant from the National Institutes of Health, Grant No: K08CA128972 (Bradner). The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

File name: TDQ-00302_SEQLISTING.txt; created Dec. 21, 2015, 30 KB in size.

BACKGROUND OF THE INVENTION

Although ~4% of the mammalian genome encodes genes expressed in male germ cells during spermatogenesis, contraceptive drugs for men have remained elusive. To date, the only drugs in clinical trials are testosterone analogs that alter endogenous androgen production. This lack of contraceptive alternatives for men is partially responsible for the high rate of unplanned pregnancies, especially in teenagers, and the associated maternal mortality and ethical, social, and financial costs associated with abortions and deliveries to single mothers. To approach this dearth of contraceptive alternatives for men, it is desirable to develop small molecules that could target spermatogenic-specific proteins that have been shown to be essential for both spermatogenesis and fertility in mammals. One such contraceptive target is the bromodomain testis-specific protein, BRDT.

BRDT is a tissue-restricted, chromatin remodeling protein expressed in pachytene spermatocytes, diplotene spermatocytes, and round spermatids. During post-meiotic maturation, BRDT localizes to the nucleus and reorganizes hyperacetylated histones through twin acetyl-lysine recognition modules, or bromodomains. The essential role of BRDT in spermatogenesis is mediated by the first bromodomain (BRDT(1)), which binds the tetra-acetylated amino-terminal tail of histone 4 (H4Kac4) with moderate potency (20 µM). Structural studies of murine BRDT have demonstrated that BRDT(1) binds a diacetylated histone 4 peptide (H4K5ac8ac) in part through a conserved asparagine, akin to seminal studies of other bromodomain co-activator proteins. Genetic studies of BRDT have demonstrated that selective deletion of the BRDT(1)-encoding region is sufficient to confer sterility in homozygous male mice, and a recently published genome-wide association study of idiopathic male infertility identified single nucleotide polymorphisms of BRDT as significantly associated with oligozoospermia or azoospermia in European men. These insights establish a compelling rationale to target BRDT for a contraceptive effect.

SUMMARY OF THE INVENTION

As described below, this invention provides novel compounds and compositions for effecting male contraception. The invention also provides methods for using such compounds and compositions in a male subject.

In one aspect, the invention provides methods for reducing or inhibiting spermatogenesis in a male subject. In embodiments, the methods involve administering an effective amount of a compound or a salt thereof that inhibits a bromodomain testis-specific protein (BRDT) to the male subject.

In one aspect, the invention provides methods for reducing the rate of male fertility in a subject. In embodiments, the methods involve administering an effective amount of a compound or a salt thereof that inhibits a BRDT to the male subject.

In the above aspects, the methods involve administering the compound or a salt thereof in an amount sufficient to reduce sperm number and/or reduce sperm motility.

In the above aspects, the methods involve administering the compound or a salt thereof in an amount sufficient to induce azoospermia, oligozoospermia, and/or asthenozoospermia. In embodiments, the methods induce a contraceptive effect in the subject.

In aspect of the invention, the invention provides pharmaceutical compositions having a compound that inhibits BRDT or a pharmaceutically acceptable salt or prodrug thereof. In embodiments, the compound or a salt thereof is present in a amount effective to reduce or inhibit spermatogenesis in a male subject.

In embodiments, the compound or a salt thereof is present in an amount effective to reduce sperm number and/or reduce sperm motility.

In embodiments, the compound or a salt thereof is present in a amount effective to induce azoospermia, oligozoospermia, and/or asthenozoospermia. In related embodiments, the compound or a salt thereof is present in a amount effective to induce a contraceptive effect in the subject.

In any of the above aspects, the compound or a salt thereof is administered to the subject using any dosage and/or route of administration described herein. In embodiments, the compound or a salt thereof is administered to the subject orally, transdermally, or by injection. In related embodiments, the compound or a salt thereof is administered in the form of a tablet or capsule. In related embodiments, the compound or a salt thereof is administered by parenteral injection, intramuscular injection, intravenous injection, subcutaneous implantation, subcutaneous injection, or transdermal preparation.

In any of the above aspects, the compound or a salt thereof is administered in combination with a pharmaceutically acceptable carrier, excipient, or diluent.

In any of the above aspects, administration of the compound or a salt thereof reduces epididymal sperm number by at least about 25% of the sperm number present in a control. In embodiments, administration of the compound or a salt thereof reduces epididymal sperm number by at least about 10% of the sperm number present in a control. In related embodiments, only about 5% of the spermatozoa remaining show progressive motility after administration of the compound or a salt thereof.

In any of the above aspects, administration of the compound or a salt thereof lowers the spermatozoa concentration to not more than 3 million/mL, 2 million/L, 1 million/mL, 0.5 million/mL, 0.25 million-mL, or 0.1 million/mL. In related embodiments, administration of the compound or a salt thereof lowers the spermatozoa concentration to not more than 0.1 million/mL.

In one aspect, the invention provides kits for reducing male fertility. In embodiments, the kits contain an effective amount of a compound that inhibits BRDT or a pharmaceutically acceptable salt or prodrug thereof. In embodiments, the kits contain instructions for using the inhibitor in any of the methods described herein.

In any of the above aspects, the compound is JQ1 or a compound of any of Formulas I-XXII, or any compound disclosed herein, or a derivative or salt thereof. In embodiments, the compound is JQ1 or a pharmaceutically acceptable salt or prodrug thereof.

In any of the above aspects, the compound or a salt thereof is administered in combination with at least one additional male contraceptive agent or device. In embodiments, the additional male contraceptive is a condom. In embodiments, the additional male contraceptive is a modulator of testosterone production, androgen receptor function or stability.

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated in and constitute a part of this specification, illustrate several embodiments of the invention and, together with the description, serve to explain the principles of the invention.

Definitions

To facilitate an understanding of the present invention, a number of terms and phrases are defined below.

The term "reducing or inhibiting spermatozoa emission" refers to lowering the amount of spermatozoa present in seminal fluid during discharge of the seminal fluid from a male subject. Reduction or inhibition of spermatozoa levels in seminal fluid can be effected by suppressing spermatogenesis, inducing azoospermia, inducing oligozoospermia, and the like. Thus, in the context of the present invention, "reducing or inhibiting spermatozoa emission" has the effect of inhibiting and/or reducing the rate of fertilization when the discharged seminal fluid contacts ova from a female subject.

"Spermatogenesis" refers to the overall process of gametogenesis in the male. Spermatogenesis takes place in the seminiferous tubule and is directly regulated by levels of follicle stimulating hormone and androgen at the periphery of the seminiferous tubule, particularly upon the Sertoli cells.

The term "azoospermia" refers to a spermatozoa content below 1 million per mL seminal fluid, approaching levels of zero spermatozoa content, and are the result of suppression of spermatogenesis.

The term "oligozoospermia" refers to a spermatozoa content between 20 and one million per mL (mill/mL) seminal fluid, and are the result of inhibited levels of spermatogenesis.

By "bromodomain" is meant a portion of a polypeptide that recognizes acetylated lysine residues. In one embodiment, a bromodomain of a BET family member polypeptide comprises approximately 110 amino acids and shares a conserved fold comprising a left-handed bundle of four alpha helices linked by diverse loop regions that interact with chromatin.

By "BET family polypeptide" is meant a polypeptide comprising two bromodomains and an extraterminal (ET) domain or a fragment thereof having transcriptional regulatory activity or acetylated lysine binding activity. Exemplary BET family members include BRD2, BRD3, BRD4 and BRDT.

By "BRD2 polypeptide" is meant a protein or fragment thereof having at least 85% identity to NP_005095 that is capable of binding chromatin or regulating transcription.

The sequence of an exemplary BRD2 polypeptide follows:

MLQNVTPHNKLPGEGNAGLLGLGPEAAAPGKRIRKPSLLYEGFESPTMAS

VPALQLTPANPPPPEVSNPKKPGRVTNQLQYLHKVVMKALWKHQFAWPFR

QPVDAVKLGLPDYHKIIKQPMDMGTIKRRLENNYYWAASECMQDFNTMFT

NCYIYNKPTDDIVLMAQTLEKIFLQKVASMPQEEQELVVTIPKNSHKKGA

KLAALQGSVTSAHQVPAVSSVSHTALYTPPPEIPTTVLNIPHPSVISSPL

LKSLHSAGPPLLAVTAAPPAQPLAKKKGVKRKADTTTPTPTAILAPGSPA

SPPGSLEPKAARLPPMRRESGRPIKPPRKDLPDSQQQHQSSKKGKLSEQL

KHCNGILKELLSKKHAAYAWPFYKPVDASALGLHDYHDIIKHPMDLSTVK

RKMENRDYRDAQEFAADVRLMFSNCYKYNPPDHDVVAMARKLQDVFEFRY

AKMPDEPLBPGPLPVSTAMPPGLAKSSSESSSSESSSESSSEEEEEEDEE

DEEEEESESSDSEEERAHRLAELQEQLRAVHEQLAALSQGPISKPKRKRE

KKEKKKRKAEKHRGRAGADEDDKGPRAPRPPQPKKSKKASGSGGGSAAL

GPSGFGPSGGSGTKLPKKATKTAPPALPTGYDSEEEEESRPMSYDEKRQL

SLDINKLPGEKLGRVVHIIQAREPSLRDSNPEEIEIDFETLKPSTLRELE

RYVLSCLRKKPRKPYTIKKPVGKTKBELALEKKRELEKRLQDVSGQLNST

KKPPKKANEKTESSSAQQVAVSRLSASSSSSDSSSSSSSSSSSDTSDSDS

G

By "BRD2 nucleic acid molecule" is meant a polynucleotide encoding a BRD2 polypeptide or fragment thereof.

By "BRD3 polypeptide" is meant a protein or fragment thereof having at least 85% identity to NP_031397.1 that is capable of binding chromatin or regulating transcription.

The sequence of an exemplary BRD3 polypeptide follows:

```
 1  mstattvapa gipatpgpvn ppppevsnps kpqrktnqlq ymqnvvvktl wkhqfawpfy 61  qpvdaiklnl pdyhkiiknp mdmgtikkrl ennyywsase cmqdfntmft ncyiynkptd
```

-continued

```
121  divlmaqale  kiflqkyaqm  pqeevellpp  apkgkgrkpa  agaqsagtqq  vaayssvspa 181  tpfqsvpptv  sqtpviaatp  vptitanvts  vpvppaaapp  ppatpivpvv  pptppvvkkk 241  gvkrkadttt  pttsaitasr  sesppplsdp  kqakvvarre  sggrpikppk  kdledgevpq 301  hagkkgklse  hlrycdsilr  emlskkhaay  awpfykpvda  ealelhdyhd  iikhpmdlst 361  vkrkmdgrey  pdaggfaadv  rlmfsncyky  nppdhevvam  arklqdvfem  rfakmpdepv 421  eapalpapaa  pmvakgaess  rsseesssds  gssdseeera  trlaelqeql  kavheqlaal 481  sqapvnkpkk  kkekkekekk  kkdkekekek  hkvkaeeekk  akvappakqa  qqkkapakka 541  nstttagrql  kkggkqasas  ydseeeeegl  pmsydekrql  sldinrlpge  klgrvvhiiq 601  srepslrdsn  pdeieidfet  lkpttlrele  ryvksclqkk  qrkpfsasgk  kqaskskeel 661  agekkkelek  rlqdvsgqls  sskkparkek  pgsapsggps  rlssssses  gssssgsss 721  dssdee
```

By "Brd3 nucleic acid molecule" is meant a polynucleotide encoding a BRD3 polypeptide.

By "BRD4 polypeptide" is meant a protein or fragment thereof having at least 85% identity to NP_055114 that is capable of binding chromatin or regulating transcription.

```
1    msaesgpgtr  lrnlpvmgdg  letsqmsttq  aqaqpqpana  astnppppet  snpnkpkrqt 61   nqlqyllrvv  lktlwkhqfa  wpfqqpvdav  klnlpdyyki  iktpmdmgti  kkrlennyyw 121  naqeciqdfn  tmftncyiyn  kpgddivlma  ealeklflqk  inelpteete  imivqakgrg 181  rgrketgtak  pgvstvpntt  qastppqtqt  pqpnpppvqa  tphpfpavtp  flivqtpvmt 241  vvppqplqtp  ppvppqpqpp  papapqpvqs  hppiiaatpq  pvktkkgvkr  kadtttptti 301  dpiheppslp  pepkttklgq  rreserpvkp  pkkdvpdsqq  hpapeksskv  seqlkccsgi 361  lkemfakkha  ayawpfykpv  dvealglhdy  cdiikhpmdm  stiksklear  eyrdaqefga 421  dvrlmfsncy  kynppdhevv  amarklqdvf  emrfakmpde  peepvvavss  pavppptkvv 481  appsssdsss  dsssdsdsst  ddseeeraqr  laelqeqlka  vheqlaalsq  pqqnkpkkke 541  kdkkekkkek  hkrkeeveen  kkskakeppp  kktkknnssn  snvskkepap  mkskppptye 601  seeedkckpm  syeekrqlsl  dinklpgekl  grvvhiiqsr  epslknsnpd  eieidfetlk 661  pstlrelery  vtsclrkkrk  pqaekvdvia  gsskmkgfss  sesesssess  ssdsedsetg 721  pa
```

By "Brd4 nucleic acid molecule" is meant a polynucleotide that encodes a BRD4 polypeptide.

By "BRDT polypeptide is meant a protein or fragment thereof having at least 85% identity to NP_001717 that is capable of binding chromatin or regulating transcription.

```
1    mslpsrqtai  ivnppppeyi  ntkkngrltn  qlqylqkvvl  kdlwkhsfsw  pfqrpvdavk 61   lqlpdyytii  knpmdlntik  krlenkyyak  aseciedfnt  mfsncylynk  pgddivlmaq 121  aleklfmqkl  sqmpqeeqvv  gvkerikkgt  qqniavssak  eksspsatek  vfkqqeipsv 181  fpktsispln  vvwgasvnss  sqtaaqvtkg  vkrdadtttp  atsavkasse  fsptfteksv 241  alppikenmp  knvlpdsqqq  ynvvktvkvt  eglrhcseil  kemlakkhfs  yawpfynpvd 301  vnalglhnyy  dvvknpmdlg  tikekmdnqe  ykdaykfaad  vrlmfmncyk  ynppdhevvt 361  marmlqdvfe  thfskipiep  vesmplcyik  tditettgre  ntneassegn  ssddsederv 421  krlaklqeql  kavhqqlqvl  sqvpfrklnk  kkekskkekk  kekvnnsnen  prkmceqmrl
```

```
481  kekskrnqpk  krkqqfiglk  sedednakpm  nydekrqlsl  ninklpgdkl  grvvhiiqsr 541  epslsnsnpd  eieidfetlk  astlreleky  vsaclrkrpl  kppakkimms  keelhsqkkq 601  elekrlldvn  nqlnsrkrqt  ksdktqpska  venvsrlses  ssssssses  essssdlass 661  dssdsesemf  pkftevkpnd  spskenvkkm  knecilpegr  tgvtqigycv  qdttsanttl 721  vhqttpshvm  ppnhhqlafn  yqelehlqtv  knisplqilp  psgdseqlsn  gitmvhpsgd 781  sdttmlesec  qapvqkdiki  knadswkslg  kpvkpsgvmk  ssdelfnqfr  kaaiekevka 841  rtqelirkhl  eqntkelkas  qenqrdlgng  ltvesfsnki  qnkcsgeeqk  ehqqsseaqd 901  ksklwllkdr  dlarqkeqer  rrreamvgti  dmtlqsdimt  mfennfd
```

By "BRDT nucleic acid molecule" is meant a polynucleotide encoding a BRDT polypeptide.

"Administering" is defined herein as a means of providing an agent to a subject in a manner that results in the agent being inside the subject's body. Such an administration can be by any route including, without limitation, oral, transdermal, mucosal (e.g., vagina, rectum, oral, or nasal mucosa), by injection (e.g., subcutaneous, intravenous, parenterally, intraperitoneally, intrathecal), or by inhalation (e.g., oral or nasal). Pharmaceutical preparations are given by forms suitable for the desired route of administration.

By "agent" or "compound" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains at least some of the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be unsubstituted, or optionally substituted with one or more substituents, such as amino, alkylamino, arylamino, heteroarylamino, alkoxy, alkylthio, oxo, halo, acyl, nitro, hydroxyl, cyano, aryl, heteroaryl, alkylaryl, alkylheteroaryl, aryloxy, heteroaryloxy, arylthio, heteroarylthio, arylamino, heteroarylamino, carbocyclyl, carbocyclyloxy, carbocyclylthio, carbocyclylamino, heterocyclyl, heterocyclyloxy, heterocyclylamino, heterocyclylthio, and the like. Lower alkyls are typically preferred for the compounds of this invention.

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or optionally is substituted with one or more substituents, e.g., substituents as described herein for alkyl groups (including without limitation alkyl (preferably, lower alkyl or alkyl substituted with one or more halo), hydroxy, alkoxy (preferably, lower alkoxy), alkylthio, cyano, halo, amino, boronic acid (—B(OH)$_2$, and nitro). In certain embodiments, the aryl group is a monocyclic ring, wherein the ring comprises 6 carbon atoms.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricycle ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents, e.g., substituents as described herein for aryl groups. Examples of heteroaryl groups include, but are not limited to, pyridyl, furanyl, benzodioxolyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heterocyclic" as used herein, refers to organic compounds that contain at least at least one atom other than carbon (e.g., S, O, N) within a ring structure. The ring structure in these organic compounds can be either aromatic or, in certain embodiments, non-aromatic. Some examples of heterocyclic moieties include, are not limited to, pyridine, pyrimidine, pyrrolidine, furan, tetrahydrofuran, tetrahydrothiophene, and dioxane.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom ($C^{12}$) would be one in which the carbon atom of the compound is replaced with the $C^{13}$ isotope.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model.

By a "computer system" is meant the hardware means, software means and data storage means used to analyse atomic coordinate data. The minimum hardware means of the computer-based systems of the present invention comprises a central processing unit (CPU), input means, output means and data storage means. Desirably a monitor is provided to visualize structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

By "computer readable media" is meant any media which can be read and accessed directly by a computer e.g. so that the media is suitable for use in the above-mentioned computer system. The media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "effective amount" is meant the amount of an agent required to provide contraception to an otherwise fertile male. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents. Examples of heteroaryl groups include, but are not limited to, pyridyl, furanyl, benzodioxolyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heterocyclic" as used herein, refers to organic compounds that contain at least at least one atom other than carbon (e.g., S, O, N) within a ring structure. The ring structure in these organic compounds can be either aromatic or non-aromatic. Some examples of heterocyclic moieties include, are not limited to, pyridine, pyrimidine, pyrrolidine, furan, tetrahydrofuran, tetrahydrothiophene, and dioxane.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom ($C^{12}$) would be one in which the carbon atom of the compound is replaced with the $C^{13}$ isotope.

The invention provides a number of targets that are useful for the development of highly specific drugs to reduce fertility in a male subject. In addition, the methods of the invention provide a facile means to identify other contraceptive therapies that are safe for use in male subjects. In addition, the methods of the invention provide a route for analyzing virtually any number of compounds for effects on a disease described herein with high-volume throughput, high sensitivity, and low complexity.

By "fitting" is meant determining by automatic, or semi-automatic means, interactions between one or more atoms of an agent molecule and one or more atoms or binding sites of a BET family member (e.g., a bromodomain BRD2, BRD3, BRD4 and BRDT), and determining the extent to which such interactions are stable. Various computer-based methods for fitting are described further herein.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

The term "obtaining" as in "obtaining compound" is intended to include purchasing, synthesizing or otherwise acquiring the compound.

The term "optical isomers" as used herein includes molecules, also known as chiral molecules, that are exact non-superimposable mirror images of one another.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcutiular, intraarticulare, subcapsular, subarachnoid, intraspinal and intrasternal injection and infusion.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or adjuvant" refers to an excipient, carrier or adjuvant that can be administered to a subject, together with an agent, e.g., any of the compounds described herein, and which does not destroy the pharmacological activity thereof and is nontoxic when administered in doses sufficient to deliver a therapeutic amount of the agent.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbanyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "polymorph" as used herein, refers to solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing.

The term "prodrug" includes compounds with moieties which can be metabolized in vivo. Generally, the prodrugs are metabolized in vivo by esterases or by other mechanisms to active drugs. Examples of prodrugs and their uses are well-known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower alkyl amides, di-lower alkyl amides, and hydroxy amides. Preferred prodrug moieties are propionoic acid esters and acyl esters. Prodrugs which are converted to active forms through other mechanisms in vivo are also included.

Furthermore the indication of stereochemistry across a carbon-carbon double bond is also opposite from the general chemical field in that "Z" refers to what is often referred to as a "cis" (same side) conformation whereas "E" refers to what is often referred to as a "trans" (opposite side) conformation. Both configurations, cis/trans and/or Z/E are encompassed by the compounds of the present invention.

With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA, or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well-known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well-known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 85% identity to a reference amino acid sequence (for example, any one of the amino acid sequences described herein) or nucleic acid sequence (for example, any one of the nucleic acid sequences described herein). Preferably, such a sequence is at least 85%, 90%, 95%, 99% or even 100% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e.sup.-3 and e.sup.-100 indicating a closely related sequence.

By "reduces" or "increases" is meant a negative or positive alteration, respectively, of at least about 10%, 25%, 50%, 75%, or 100% relative to a reference.

By "root mean square deviation" is meant the square root of the arithmetic mean of the squares of the deviations from the mean.

By "reducing cell survival" is meant to inhibit the viability of a cell or to induce cell death relative to a reference cell.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "subject" is meant a mammal, including, but not limited to, a human or non-human mammal, such as a bovine, equine, canine, ovine, or feline.

By "specifically binds" is meant a compound or antibody that recognizes and binds a polypeptide of the invention, but which does not substantially recognize and bind other molecules in a sample, for example, a biological sample, which naturally includes a polypeptide of the invention.

The term "sulfhydryl" or "thiol" means —SH.

As used herein, the term "tautomers" refers to isomers of organic molecules that readily interconvert by tautomerization, in which a hydrogen atom or proton migrates in the reaction, accompanied in sonic occasions by a switch of a single bond and an adjacent double bond.

As used herein, the terms "treat," "treating," "treatment," and the like refer to reducing or ameliorating a disorder and/or symptoms associated therewith. By "ameliorate" is meant decrease, suppress, attenuate, diminish, arrest, or stabilize the development or progression of a disease. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

"An effective amount" refers to an amount of a compound, which confers a contraceptive effect on the treated subject. The effect may be objective (i.e., measurable by some test or marker) or subjective (i.e., subject gives an indication of or feels an effect). An effective amount of a compound described herein may range from about 1 mg/Kg to about 5000 mg/Kg body weight. Effective doses will also vary depending on route of administration, as well as the possibility of co-usage with other agents. In embodiments of the present invention, "an effective amount" of an agent or composition is an amount sufficient to effect contraception.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

The term "including" is used herein to mean, and is used interchangeably with, the phrase "including but not limited to."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compounds, compositions, or methods provided herein can be combined with one or more of any of the other compounds, compositions, and methods provided herein.

DESCRIPTION OF THE DRAWINGS

FIG. 2A is the structure of the active (+)-JQ1 enantiomer. FIG. 2B is a plot showing the competitive inhibition of BRDT binding to synthetic biotinylated H4Kac4 by (+)-JQ1 (IC50: 11 nM) using a proximity detection assay. FIG. 2C includes a graph showing the results of the assay with 500 nM of the indicated compound. Error bars show standard deviation.

FIG. 3 is a MAFFT alignment of human BRDT and human BRD4.

FIG. 4 is a MAFFT alignment of human BRDT and mouse BRDT.

FIG. 5A includes an image providing a gross analysis of testes from 9-meek old mice injected with control or JQ1. FIG. 5B includes a graphical representation of testes weights (mg) from mice treated with control or JQ1 for 3-6 weeks, 6-9 weeks, or 6-12 weeks of age. Data represent the mean±standard error of the mean (SEM), and are annotated with P-values as obtained from a two-tailed t-test (* indicates significant at P<0.05). FIGS. 5C-5F include histological stains showing the histology of testes of 6-week old mice treated with (FIG. 5C) control or (FIG. 5D) JQ1 from 3-6 weeks of age, and 12-week old mice treated with (FIG. 5E) control or (FIG. 5F) JQ1 from 6-12 weeks of age. Intertubular islands of Leydig cells are depicted with arrows in FIGS. 5C-5F. Sertoli cell vacuolization (V) is highlighted in several tubules in FIG. 5F. FIGS. 5G and 5H include histological stains showing the histology of the epididymides from males treated with (FIG. 5G) control or (FIG. 5H) JQ1 from 6-12 weeks of age. Fewer spermatozoa and multiple large nucleated cells (black arrow) are observed in the epididymal lumen of the JQ1-treated mice (FIG. 5H) compared to the control epididymal lumen (FIG. 5G), which is densely packed with mature spermatozoa. FIGS. 5C-5H were photographed at the same magnification.

FIG. 6A is a graphical representation of the sperm counts obtained from the entire epididymides of males treated with JQ1 or control from 6-9 weeks of age or the tail (cauda) of the epididymis of males treated from 6-12 weeks of age. FIG. 6B includes a graph showing the in vitro developmental potential of oocytes obtained from superovulated females mated to males treated for 5 weeks with a control or JQ1. All data represent the mean±SEM, and are annotated with P-values as obtained from a two-tailed t-test (* indicates significant at P<0.05).

FIG. 7A includes a graph showing the quantitative RT-PCR results for males treated from 6-12 weeks of age with JQ1 or a control solution. The mouse genes tested were Plzf (promyelocytic leukemia zinc-finger or Zbtb16), Stra8 (stimulated by retinoic acid gene 8), Brdt (bromodomain, testis-specific), Cena1 (cyclin A1), Hist1h1t (histone cluster 1, histone 1, testis-specific), Papolb (poly (A) polymerase beta or Tpap), Klf17 (Kruppel-like factor 17 or Zfp393), and Prm1 (protamine 1). Data represent the mean±SEM, and are annotated with P-values as obtained from a two-tailed t-test (* indicates significant at P<0.05; the P-value for Prm1 is 0.06). FIGS. 7B and 7C include immunohistochemical staining images of TNP2 in control-treated (FIG. 7B) and JQ1-treated (FIG. 7C) testes.

FIGS. 8A-8C show the effect of JQ1 on sperm count and testicular mass. In a repeat study, C57B6 mice were treated with JQ1 (50 mpk×8 weeks). FIG. 8A includes a graph showing sperm count in the test mice. FIG. 8B includes a graph showing testes weight in the test mice. FIG. 8C includes phase contrast images of sperm from test mice.

FIGS. 9A-9C show that the effects of JQ1 are reversed upon removal. FIG. 9A includes a graph showing sperm motility levels in test mice two months and four months after termination of JQ1 treatment. FIG. 9B includes a graph showing testes weight in test mice two months and four months after termination of JQ1 treatment. FIG. 9C includes a graph showing the sperm counts in test mice two months and four months after termination of JQ1 treatment.

DETAILED DESCRIPTION OF THE INVENTION

Figure 1:
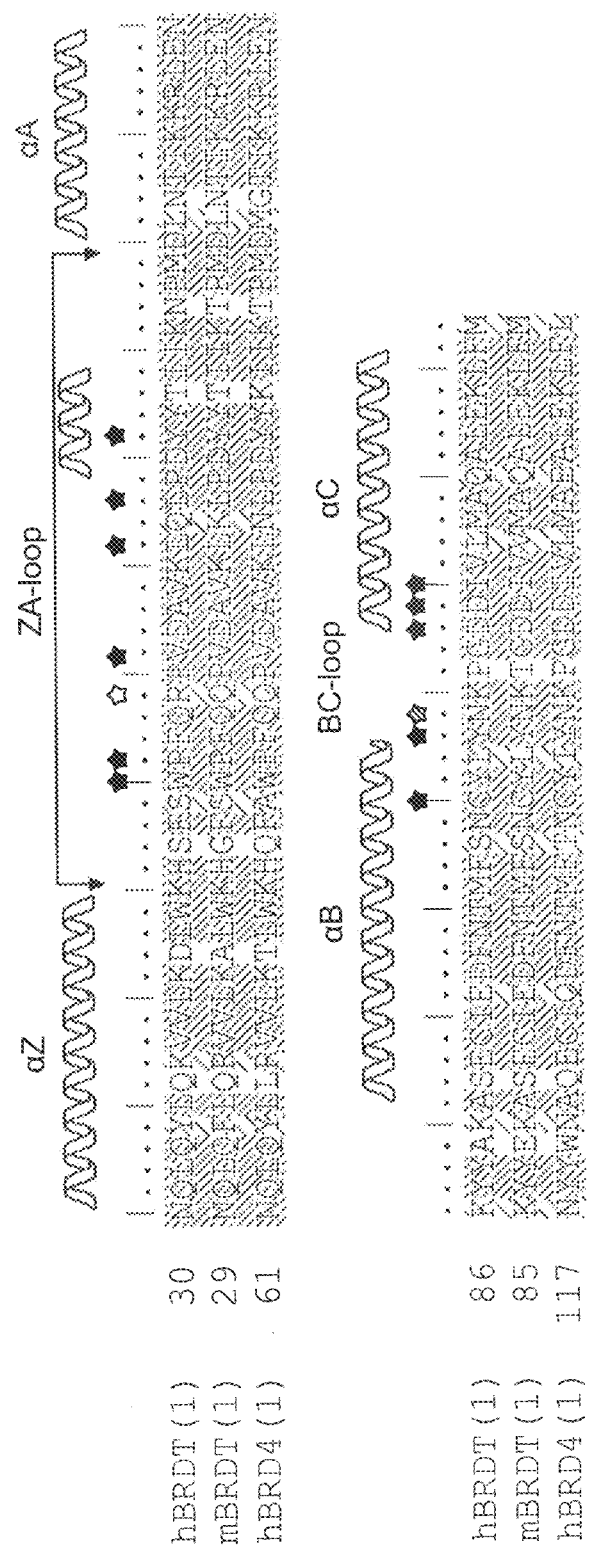
FIG. 1 is a sequence comparison of human BRDT(1) with human BRD4(1) and mouse BRDT(1). Protein sequence alignment reveals a high degree of sequence identity between homologous and orthologous domains. Identical (red) and similar (yellow) residues are highlighted. Depicted above the residue sequences are schematic representations of major helical elements. Contacts between (+)-JQ1 and BRDT(1) are depicted with a black star. The conserved asparagine mediating acetyl-lysine recognition is depicted with a blue star.

This invention is based, at least in part, on the discovery that a small-molecule inhibitor (JQ1) of the bromodomain and extra-terminal (BET) subfamily of epigenetic reader proteins is essential for chromatin remodeling during spermiogenesis. Biochemical analysis confirms that occupancy of the BRDT acetyl-lysine binding pocket by JQ1 prevents recognition of acetylated histone H4. The invention is also based on the discovery that treatment of mice with JQ1 reduced the number and motility of spermatozoa, as well as testis size. Although JQ1-treated males mate normally, inhibitory effects of JQ1 evident at the spermatocyte stage cause a dramatic decrease in fertilized oocytes and a reversible contraceptive effect in males. Accordingly, the present invention is directed to a novel type of male contraceptive that can cross the blood:testis boundary and inhibits bromodomain activity during spermatogenesis.

Bromodomain-Containing Proteins

Gene regulation is fundamentally governed by reversible, non-covalent assembly of macromolecules. Signal transduction to RNA polymerase requires higher-ordered protein complexes, spatially regulated by assembly factors capable of interpreting the post-translational modification states of chromatin. Epigenetic readers are structurally diverse proteins each possessing one or more evolutionarily conserved effector modules, which recognize covalent modifications of histone proteins or DNA. The ε-N-acetylation of lysine residues (Kac) on histone tails is associated with an open chromatin architecture and transcriptional activation[3]. Context-specific, molecular recognition of acetyl-lysine is principally mediated by bromodomains.

Bromodomain-containing proteins are of substantial biological interest, as components of transcription factor complexes (TAF1, PCAF, Gen5 and CBP) and determinants of epigenetic memory[4]. There are 41 human proteins containing a total of 57 diverse bromodomains. Despite large sequence variations, all bromodomains share a conserved fold comprising a left-handed bundle of four alpha helices ($\alpha_Z$, $\alpha_A$, $\alpha_B$, $\alpha_C$), linked by diverse loop regions (ZA and BC loops) that determine substrate specificity. Co-crystal structures with peptidic substrates showed that the acetyl-lysine is recognized by a central hydrophobic cavity and is anchored by a hydrogen bond with an asparagine residue present in most bromodomains[5]. The bromodomain and extra-terminal (BET)-family (BRD2, BRD3, BRD4 and BRDT) shares a common domain architecture comprising two N-terminal bromodomains that exhibit high level of sequence conservation, and a more divergent C-terminal recruitment domain[6].

The invention features compositions and methods that are useful for inhibiting human bromodomain proteins.

Compounds of the Invention

The invention provides compounds (e.g., JQ1 and compounds of formulas delineated herein) that bind in the binding pocket of the apo crystal structure of the first bromodomain of a BET family member (e.g., BRDT, BRD2, BRD3, BRD4). Without wishing to be bound by theory, these compounds are particularly effective in reducing male fertility. In one approach, compounds useful for reducing male fertility are selected using a molecular docking program to identify compounds that are expected to bind to a bromodomain structural binding pocket. In certain embodiments, a compound of the invention can prevent, inhibit, or disrupt, or reduce by at least 10%, 25%, 50%, 75%, or 100% the biological activity of a BET family member (e.g., BRD2, BRD3, BRD4, BRDT) and/or disrupt the subcellular localization of such proteins, e.g., by binding to a binding site in a bromodomain apo binding pocket.

In certain embodiments, a compound of the invention is a small molecule having a molecular weight less than about 1000 daltons, less than 800, less than 600, less than 500, less than 400, or less than about 300 daltons. Examples of compounds of the invention include JQ1 and other compounds that bind the binding pocket of the apo crystal structure of the first bromodomain of a BET family member (e.g., BRD4 (hereafter referred to as BRD4(1); PDB ID 2OSS). JQ1 is a novel thieno-triazolo-1,4-diazepine. The invention further provides pharmaceutically acceptable salts of such compounds.

In one aspect, the compound is a compound of Formula I:

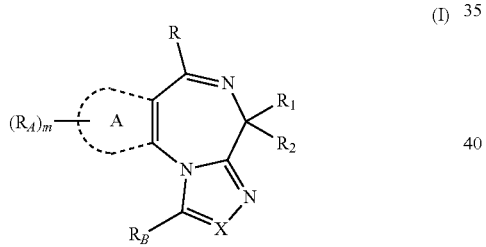

(I)

wherein

X is N or $CR_5$;

$R_5$ is H, alkyl, cycloalkyl, heterocycloalkyl, aryl, or heteroaryl, each of which is optionally substituted;

$R_B$ is H, alkyl, hydroxyalkyl, aminoalkyl, alkoxyalkyl, haloalkyl, hydroxy, alkoxy, or —COO—$R_3$, each of which is optionally substituted;

ring A is aryl or heteroaryl;

each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

R is alkyl, cycloalkyl, heterocycloalkyl, aryl, or heteroaryl; each of which is optionally substituted;

$R_1$ is —(CH$_2$)$_n$-L, in which n is 0-3 and L is H, —COO—$R_3$, —CO—$R_3$, —CO—N($R_3R_4$), —S(O)$_2$—$R_3$, —S(O)$_2$—N($R_3R_4$), N($R_3R_4$), N($R_4$)C(O)$R_3$, optionally substituted aryl, or optionally substituted heteroaryl;

$R_2$ is H, D (deuterium), halogen, or optionally substituted alkyl;

each $R_3$ is independently selected from the group consisting of:
(i) H, aryl, substituted aryl, heteroaryl, or substituted heteroaryl;
(ii) heterocycloalkyl or substituted heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted; and
(iv) NH$_2$, N═CR$_4$R$_6$;

each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that (a) if ring A is thienyl, X is N, R is phenyl or substituted phenyl, $R_2$ is H, $R_B$ is methyl, and $R_1$ is —(CH$_2$)$_n$-L, in which n is 1 and L is —CO—N($R_3R_4$), then $R_3$ and $R_4$ are not taken together with the nitrogen atom to which they are attached to form a morpholino ring;

(b) if ring A is thienyl, X is N, R is substituted phenyl, $R_2$ is H, $R_B$ is methyl, and $R_1$ is —(CH$_2$)$_n$-L, in which n is 1 and L is —CO—N($R_3R_4$), and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if ring A is thienyl, X is N, R is substituted phenyl, $R_2$ is H, $R_B$ is methyl, and $R_1$ is —(CH$_2$)$_n$-L, in which n is 1 and L is —COO—$R_3$, then $R_3$ is not methyl or ethyl;

or a salt, solvate or hydrate thereof.

In certain embodiments, R is aryl or heteroaryl, each of which is optionally substituted.

In certain embodiments, L is H, —COO—$R_3$, —CO—N($R_3R_4$), —S(O)$_2$—$R_3$, —S(O)$_2$—N($R_3R_4$), N($R_3R_4$), N($R_4$)C(O)$R_3$ or optionally substituted aryl. In certain embodiments, each $R_3$ is independently selected from the group consisting of: H, —C$_1$-C$_8$ alkyl, containing 0, 1, 2, or 3 heteroatoms selected from O, S, or N; or NH$_2$, N═CR$_4$R$_6$.

In certain embodiments, $R_2$ is H, D, halogen or methyl.

In certain embodiments, $R_B$ is alkyl, hydroxyalkyl, haloalkyl, or alkoxy; each of which is optionally substituted.

In certain embodiments, $R_B$ is methyl, ethyl, hydroxymethyl, methoxymethyl, trifluoromethyl, COOH, COOMe, COOEt, or COOCH$_2$OC(O)CH$_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.

In certain embodiments, m is 1 or 2, and at least one occurrence of $R_A$ is methyl.

In certain embodiments, each $R_A$ is independently H, an optionally substituted alkyl, or any two $R_A$ together with the atoms to which each is attached, can form an aryl.

In another aspect, the compound is a compound of Formula II:

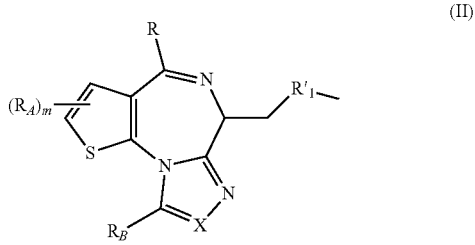

(II)

wherein
  X is N or $CR_5$;
  $R_5$ is H, alkyl, cycloalkyl, heterocycloalkyl, aryl, or heteroaryl, each of which is optionally substituted;
  $R_B$ is H, alkyl, hydroxylalkyl, aminoalkyl, alkoxyalkyl, haloalkyl, hydroxy, alkoxy, or —COO—$R_3$, each of which is optionally substituted;
  each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
  R is alkyl, cycloalkyl, heterocycloalkyl, aryl, or heteroaryl, each of which is optionally substituted;
  $R'_1$ is H, —COO—$R_3$, —CO—$R_3$, optionally substituted aryl, or optionally substituted heteroaryl;
  each $R_3$ is independently selected from the group consisting of:
    (i) H, aryl, substituted aryl, heteroaryl, substituted heteroaryl;
    (ii) heterocycloalkyl or substituted heterocycloalkyl;
    (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; cycloalkyl, substituted —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl; each of which may be optionally substituted;
  m is 0, 1, 2, or 3; provided that if $R'_1$ is —COO—$R_3$, X is N, R is substituted phenyl, and $R_B$ is methyl, then $R_3$ is not methyl or ethyl;
  or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, $R'_1$ is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, $R'_1$ is —COO—$R_3$, and $R_3$ is methyl, ethyl, propyl, i-propyl, butyl, sec-butyl, or t-butyl; or $R'_1$ is H or optionally substituted phenyl.

In certain embodiments, $R_B$ is methyl, ethyl, hydroxy methyl, methoxymethyl, trifluoromethyl, COOH, COOMe, COOEt, $COOCH_2OC(O)CH_3$.

In certain embodiments, $R_B$ is methyl, ethyl, hydroxy methyl, methoxymethyl, trifluoromethyl, COOH, COOMe, COOEt, or $COOCH_2OC(O)CH_3$.

In certain embodiments, each $R_A$ is independently an optionally substituted alkyl, or any two $R_A$ together with the atoms to which each is attached, can form a fused aryl.

In certain embodiments, each $R_A$ is methyl.

In another aspect, the compound is a compound of formula III:

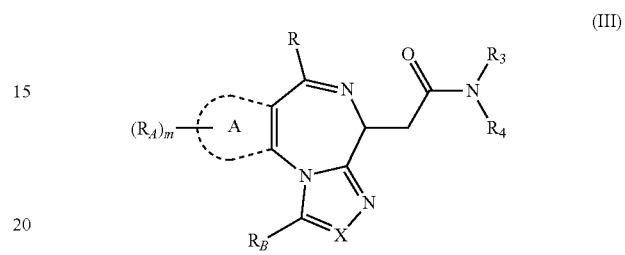

(III)

wherein
  X is N or $CR_5$;
  $R_5$ is H, alkyl, cycloalkyl, heterocycloalkyl, aryl, or heteroaryl, each of which is optionally substituted;
  $R_B$ is H, alkyl, hydroxylalkyl, aminoalkyl, alkoxyalkyl, haloalkyl, hydroxy, alkoxy, or —COO—$R_3$, each of which is optionally substituted;
  ring A is aryl or heteroaryl;
  each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
  R is alkyl, cycloalkyl, heterocycloalkyl, aryl, or heteroaryl, each of which is optionally substituted;
  each $R_3$ is independently selected from the group consisting of:
    (i) H, aryl, substituted aryl, heteroaryl, or substituted heteroaryl;
    (ii) heterocycloalkyl or substituted heterocycloalkyl;
    (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
    (iv) $NH_2$, N=$CR_4R_6$;
  each $R_4$ is independently H, alkyl, alkyl, cycloalkyl, heterocycloalkyl, aryl, or heteroaryl, each of which is optionally substituted;
  or $R_3$ and $R_4$ are taken together with the nitrogen atom to which they are attached to form a 4-10-membered ring;
  $R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;
  m is 0, 1, 2, or 3;
  provided that:
    (a) if ring A is thienyl, X is N, R is phenyl or substituted phenyl, $R_B$ is methyl, then $R_3$ and $R_4$ are not taken together with the nitrogen atom to which they are attached to form a morpholino ring; and (b) if ring A is thienyl, X is N, R is substituted phenyl, $R_2$ is H, $R_B$ is methyl, and one of $R_3$ and $R_4$ is H, then the other of $R_3$ and $R_4$ is not methyl, hydroxyethyl, alkoxy, phenyl, substituted phenyl, pyridyl or substituted pyridyl; and or a salt, solvate or hydrate thereof.

In certain embodiments, R is aryl or heteroaryl, each of which is optionally substituted. In certain embodiments, R is phenyl or pyridyl, each of which is optionally substituted.

In certain embodiments, R is p-Cl-phenyl, o-Cl-phenyl, m-Cl-phenyl, p-F-phenyl, o-F-phenyl, m-F-phenyl or pyridinyl. In certain embodiments, $R_3$ is H, $NH_2$, or $N=CR_4R_6$.

In certain embodiments, each $R_4$ is independently H, alkyl, cycloalkyl, heterocycloalkyl, aryl, heteroaryl; each of which is optionally substituted.

In certain embodiments, $R_6$ is alkyl, alkenyl, cycloalkyl, heterocycloalkyl, aryl, or heteroaryl, each of which is optionally substituted.

In another aspect, the compound is a compound of formula IV:

(IV)

wherein

X is N or $CR_5$;

$R_5$ is H, allyl, cycloalkyl, heterocycloalkyl, aryl, or heteroaryl, each of which is optionally substituted;

$R_B$ is H, alkyl, hydroxylalkyl, aminoalkyl, alkoxyalkyl, haloalkyl, hydroxy, alkoxy, or —COO—$R_3$, each of which is optionally substituted;

ring A is aryl or heteroaryl;

each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

$R_1$ is —$(CH_2)_n$-L, in which n is 0-3 and L is H, —COO—$R_3$, —CO—$R_3$, —CO—N($R_3R_4$), —S(O)$_2$—$R_3$, —S(O)$_2$—N($R_3R_4$), N($R_3R_4$), N($R_4$)C(O)$R_3$, optionally substituted aryl, or optionally substituted heteroaryl;

$R_2$ is H, D, halogen, or optionally substituted alkyl;

each $R_3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) $NH_2$, $N=CR_4R_6$;

each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that (a) if ring A is thienyl, X is N, $R_2$ is H, $R_B$ is methyl, and $R_1$ is —$(CH_2)_n$-L, in which n is 0 and L is —CO—N($R_3R_4$), then $R_3$ and $R_4$ are not taken together with the nitrogen atom to which they are attached to form a morpholino ring;

(b) if ring A is thienyl, X is N, $R_2$ is H, $R_B$ is methyl, and $R_1$ is —$(CH_2)_n$-L, in which n is 0 and L is —CO—N($R_2R_4$), and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if ring A is thienyl, X is N, $R_2$ is H, $R_B$ is methyl, and $R_1$ is —$(CH_2)_n$-L, in which n is 0 and L is —COO—$R_3$, then $R_3$ is not methyl or ethyl; or a salt, solvate or hydrate thereof.

In certain embodiments, $R_1$ is —$(CH_2)_n$-L, in which n is 0-3 and L is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, n is 1 or 2 and L is alkyl or —COO—$R_3$, and $R_3$ is methyl, ethyl, propyl, i-propyl, butyl, sec-butyl, or t-butyl; or n is 1 or 2 and L is H or optionally substituted phenyl.

In certain embodiments, $R_2$ is H or methyl.

In certain embodiments, $R_B$ is methyl, ethyl, hydroxy methyl, methoxymethyl, trifluoromethyl, COOH, COOMe, COOEt, COOCH$_2$OC(O)CH$_3$.

In certain embodiments, ring A is phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, each $R_A$ is independently an optionally substituted alkyl, or any two $R_A$ together with the atoms to which each is attached, can form an aryl.

The methods of the invention also relate to compounds of Formulae V-XXII, and to any compound described herein.

In another aspect, the compound is a compound represented by the formula:

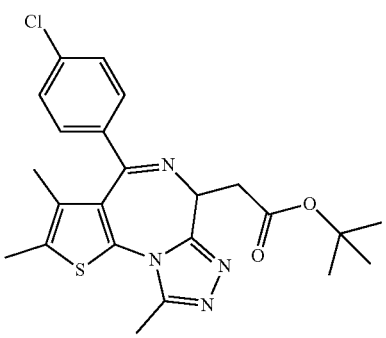 [SMILES: Cc1sc2c(c1C)C(c1ccc(Cl)cc1)=NC(CC(=O)OC(C)(C)C)c1nnc(C)n1-2]
or a salt, solvate or hydrate thereof.
In certain embodiments, the compound is (+)-JQ1:
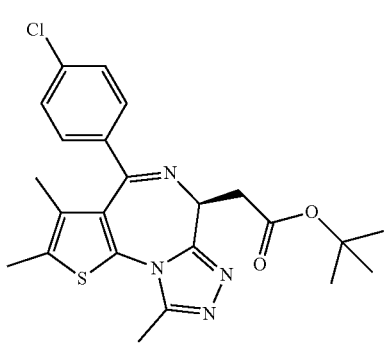 [SMILES: Cc1sc2c(c1C)C(c1ccc(Cl)cc1)=N[C@@H](CC(=O)OC(C)(C)C)c1nnc(C)n1-2]
or a salt, solvate or hydrate thereof.
In another aspect, the compound is a compound represented by the formula:
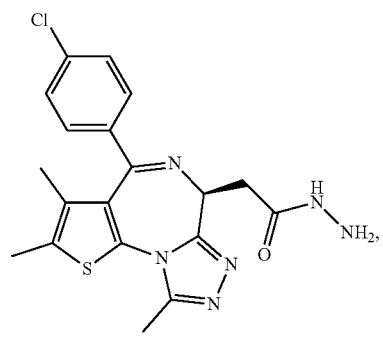
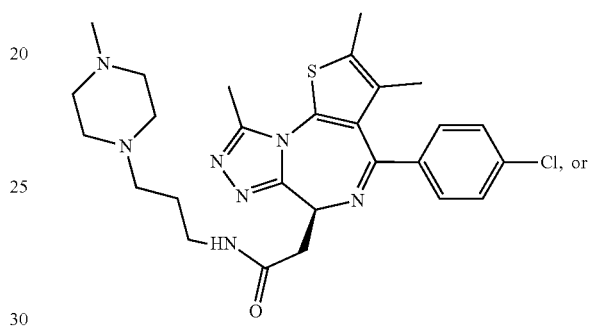
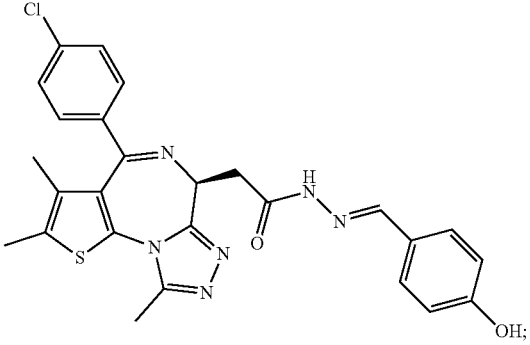
or a salt, solvate or hydrate thereof.
In another aspect, the compound is a compound represented by the formula:
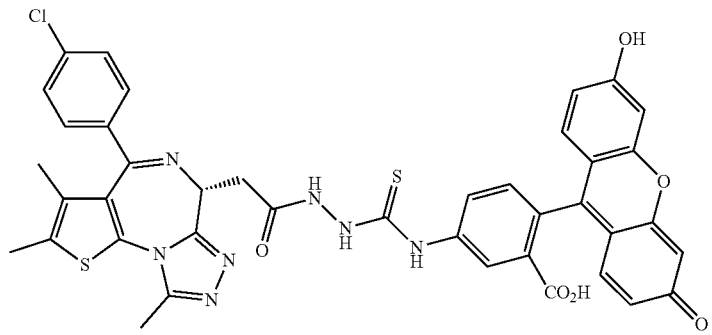
or

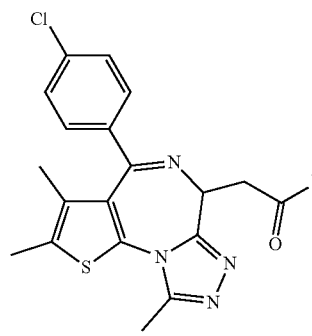
or a salt, solvate or hydrate thereof.
In another aspect, the compound is a compound represented by any one of the following formulae:
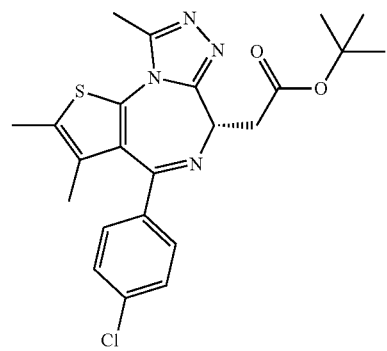
JQ1S
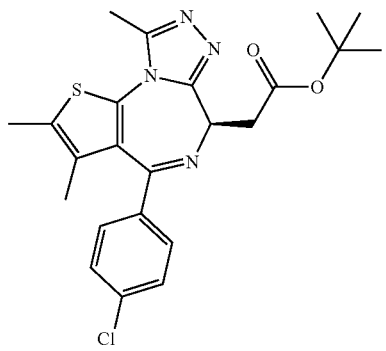
JQIR
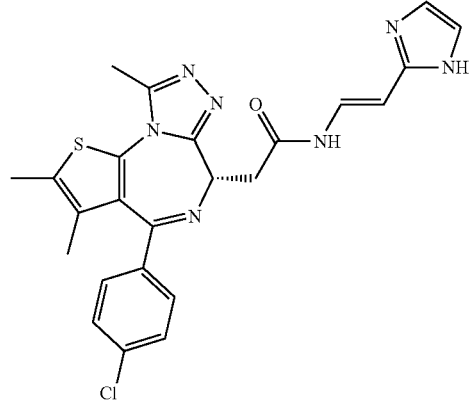
JQ6
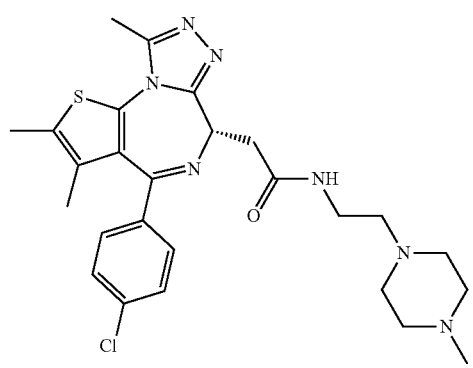
JQ13
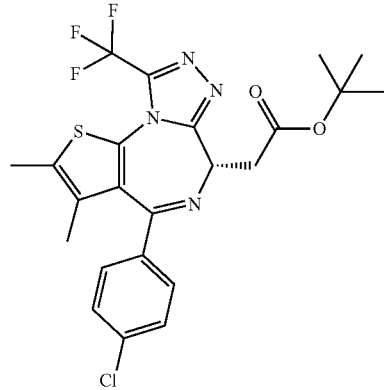
JQ11
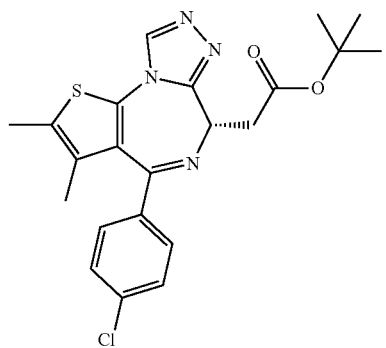
JQ21

-continued
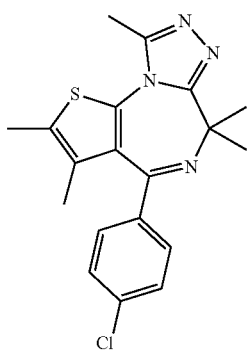
JQ20
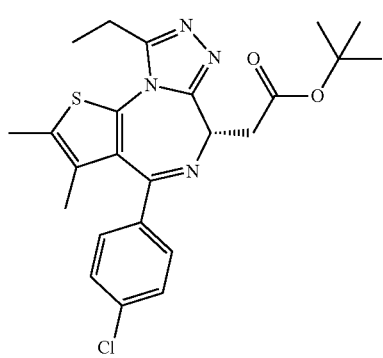
JQ19
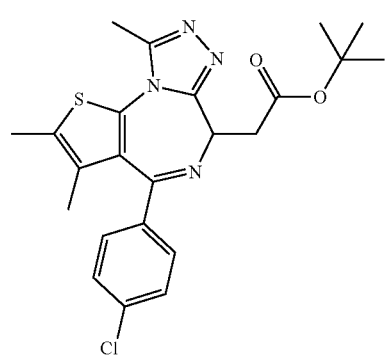
JQ24B
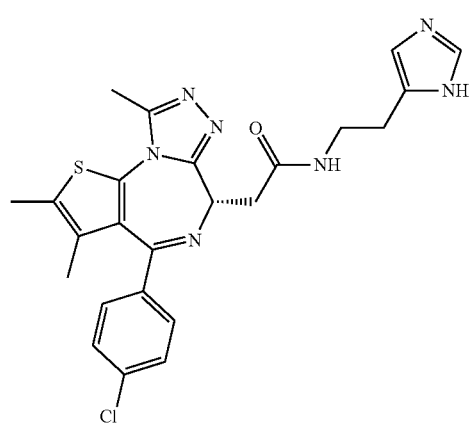
JQ8
-continued
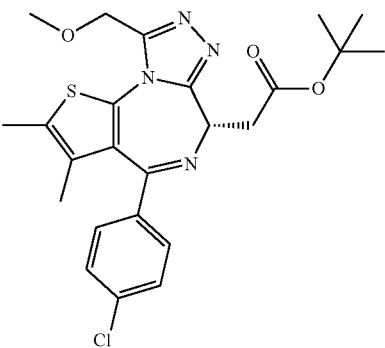
JQ18
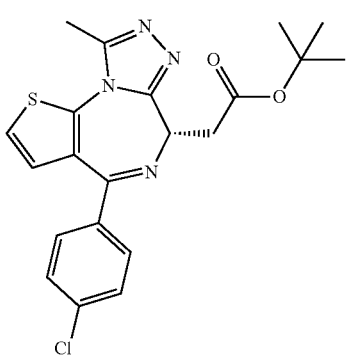
KS1
or a salt, solvate or hydrate thereof.
In another aspect, the compound is a compound represented by any one of the following formulae:
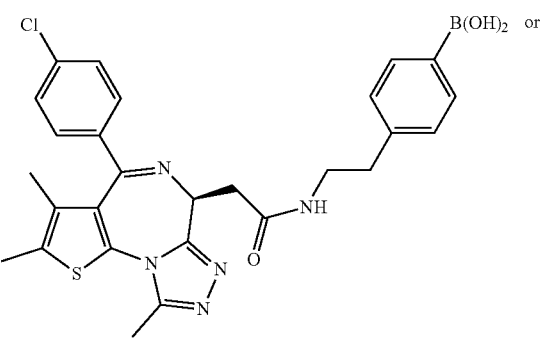
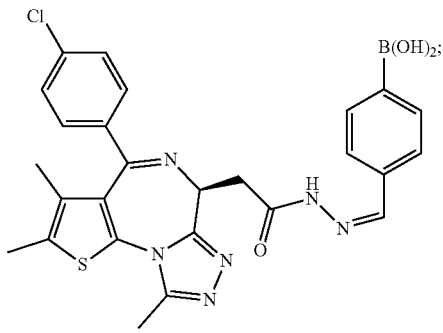
or a salt, solvate or hydrate thereof.
In another aspect, the compound is a compound represented by any one of the following structures:

31
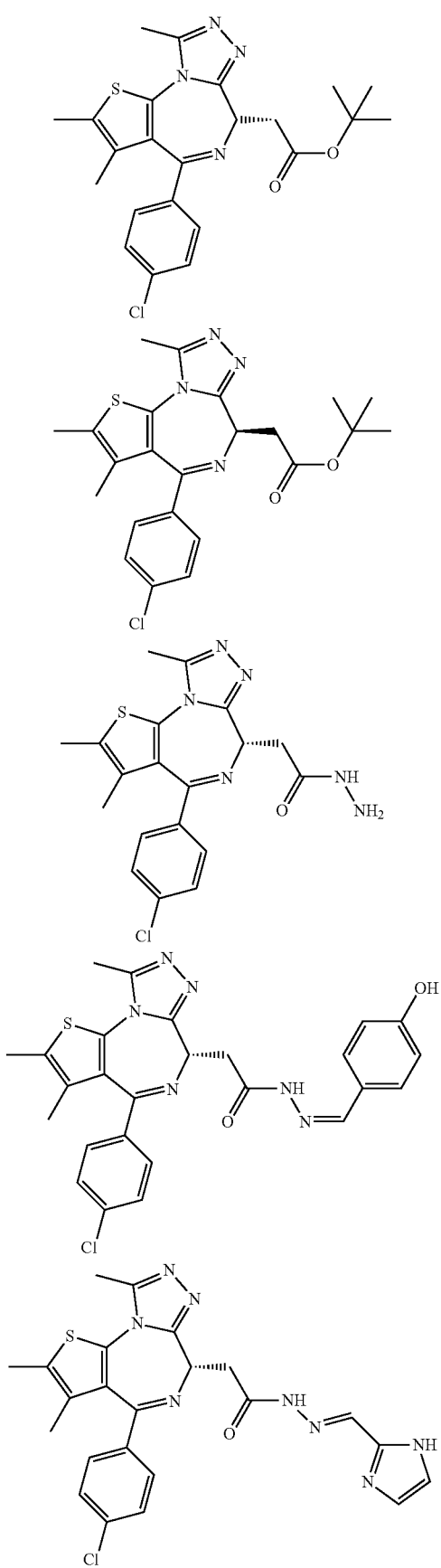
32
-continued
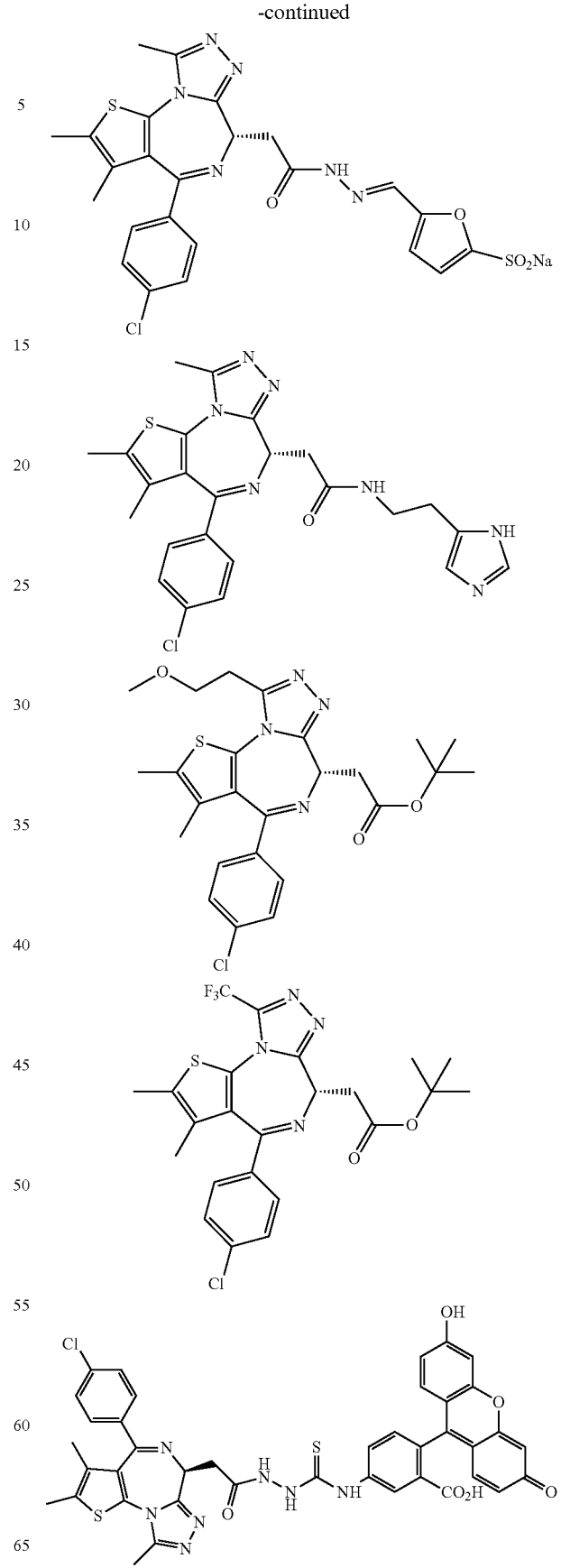

33
-continued
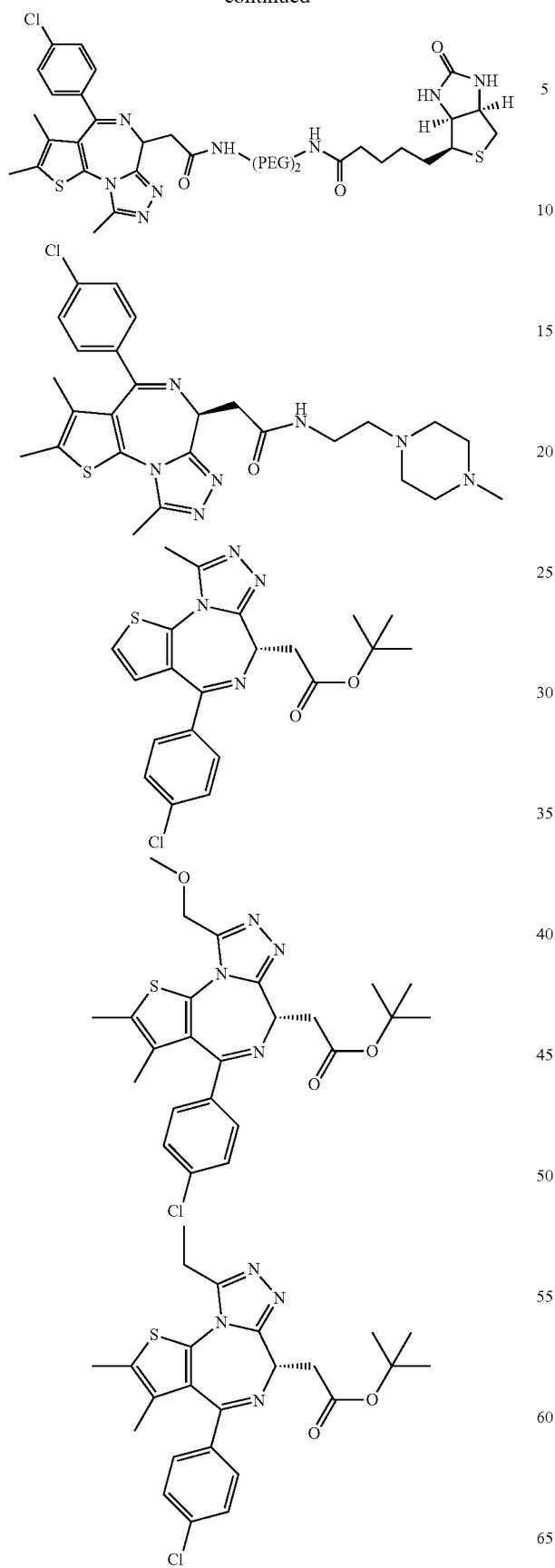
34
-continued
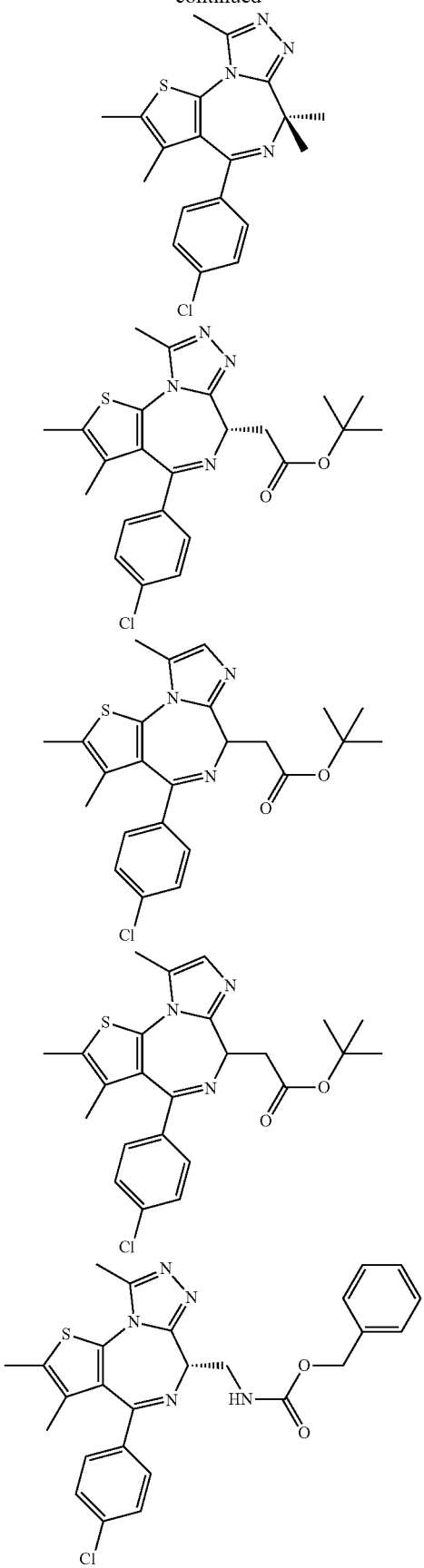

35
-continued
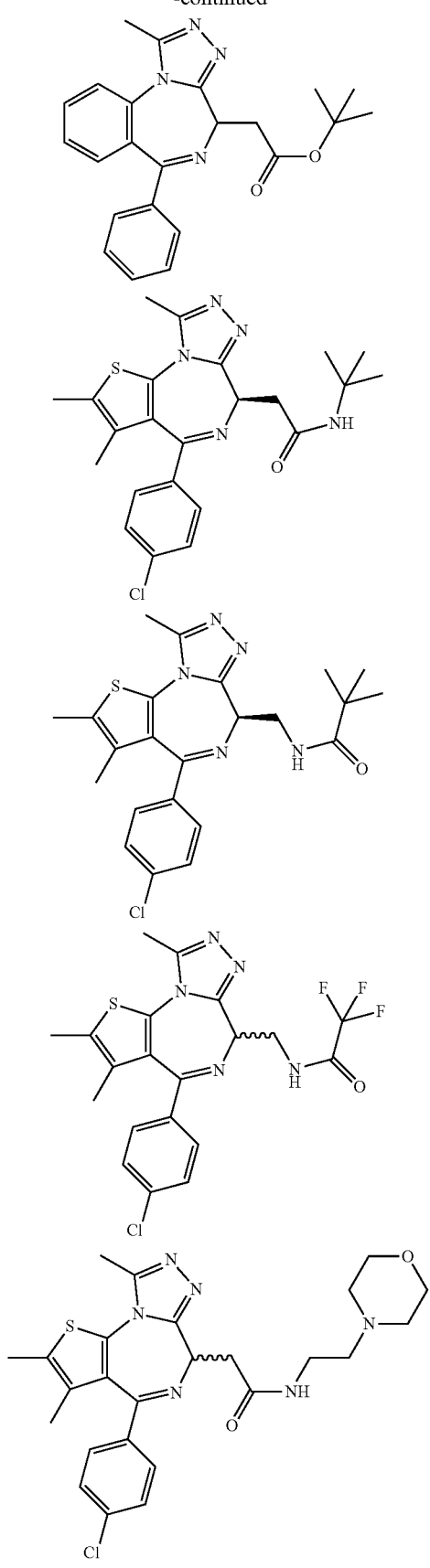
36
-continued
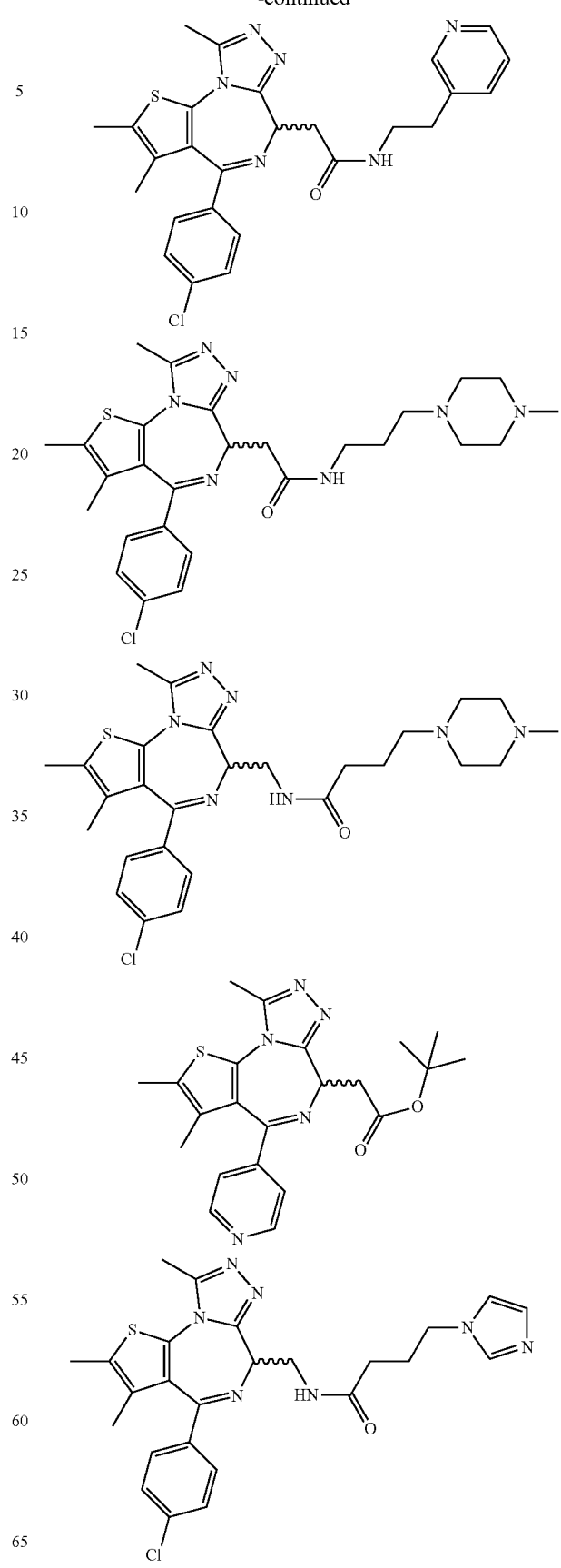

37
-continued
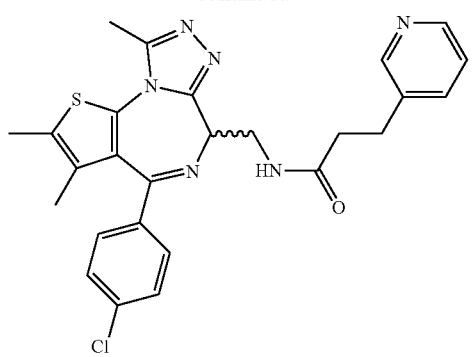
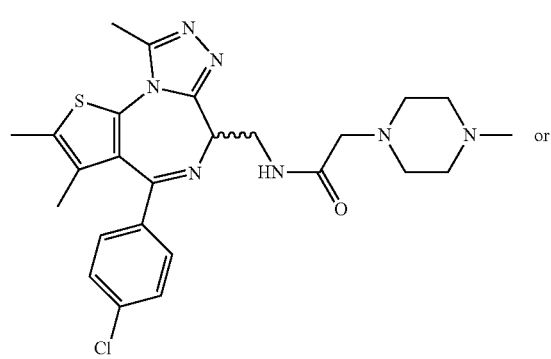
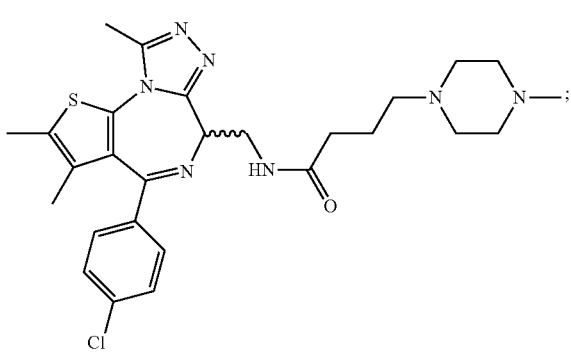 or
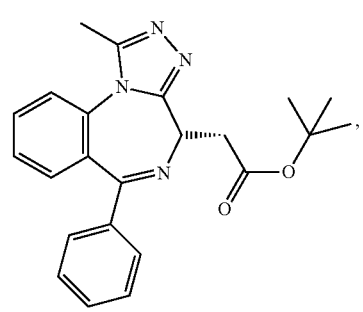
or a salt, solvate or hydrate thereof.
In certain embodiments, a compound of the invention can be represented by one of the following structures:
38
-continued
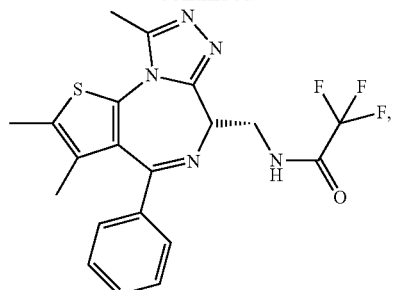
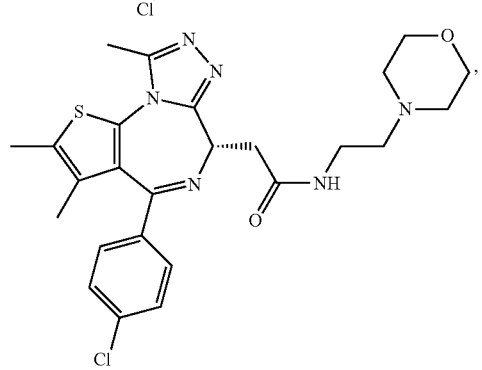
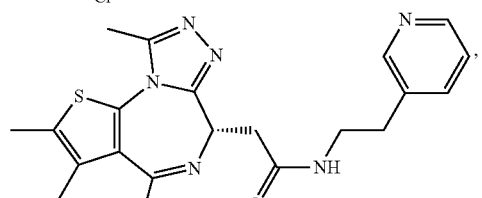
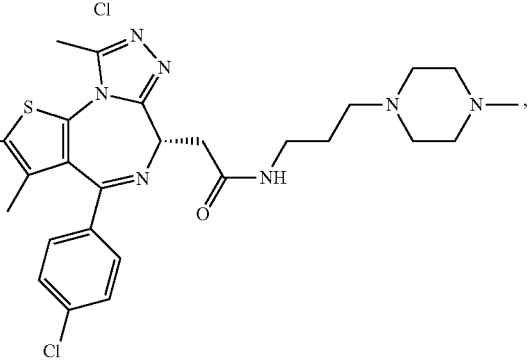
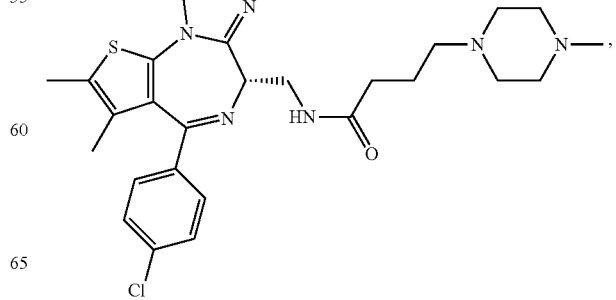

39
-continued
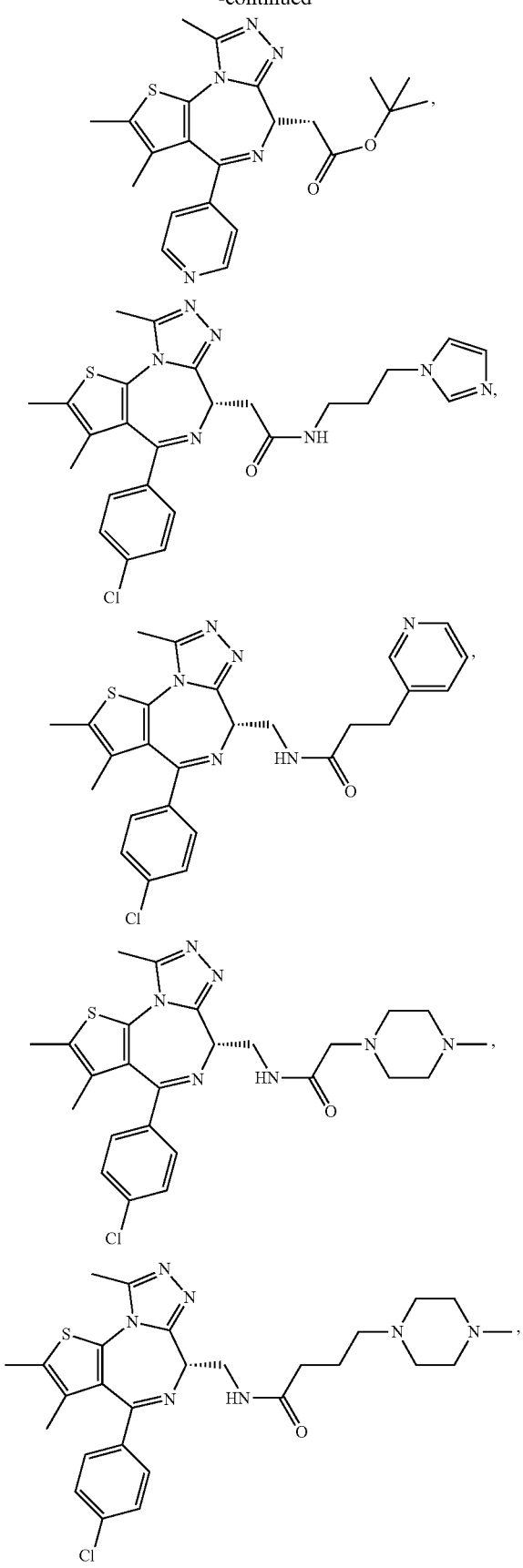
40
-continued
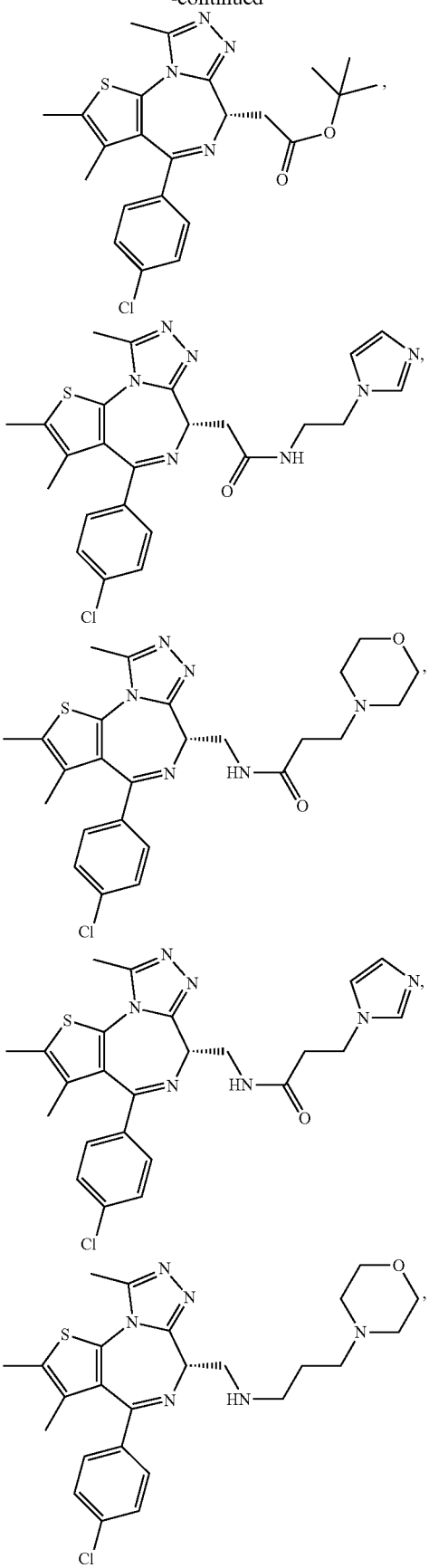

-continued
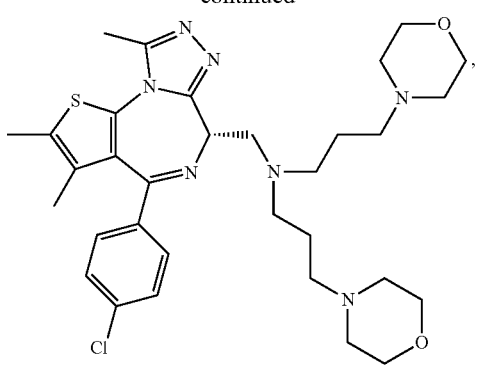
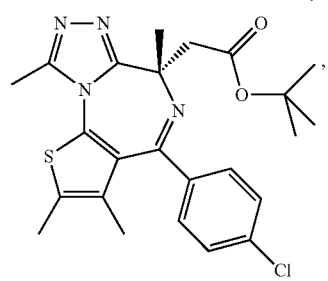
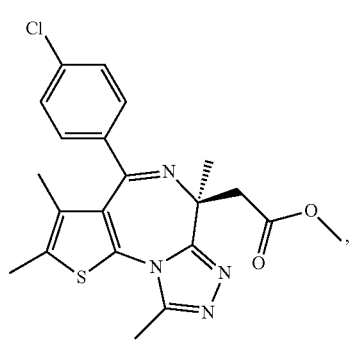
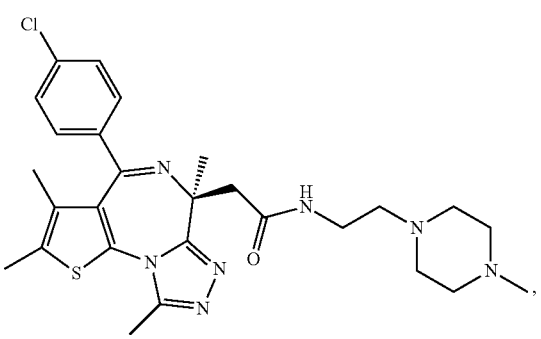
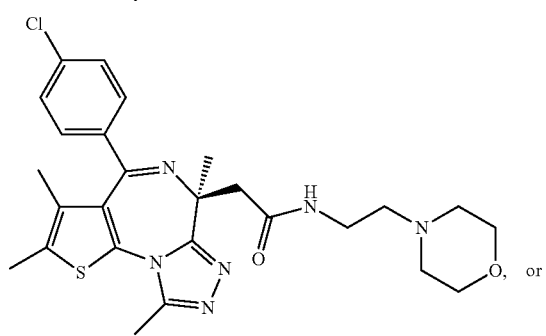, or
-continued
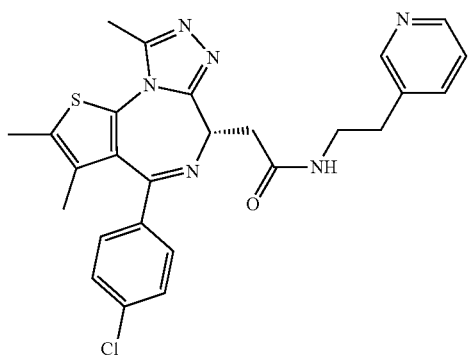 [SMILES: Cc1sc2c(c1C)C(c1ccc(Cl)cc1)=N[C@@H](CC(=O)NCCc1cccnc1)c1nnc(C)n1-2]
or a salt, solvate or hydrate thereof.
In one embodiment, the compound is represented by the structure:
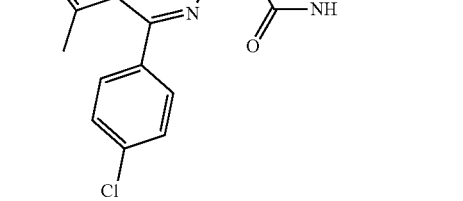
or a salt, solvate or hydrate thereof.
In another embodiment, the compound is represented by the structure:
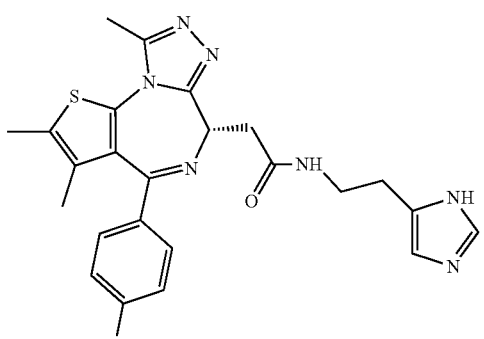
or a salt, solvate or hydrate thereof.
In another embodiment, the compound is represented by the structure:

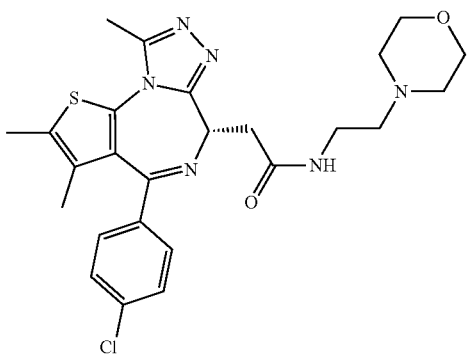

or a salt, solvate or hydrate thereof.

In certain embodiments, a compound of the invention can have the opposite chirality of any compound shown herein.

In certain embodiments, the compound is a compound represented by Formula (V), (VI), or (VII):

in which R, $R_1$, and $R_2$ and $R_B$ have the same meaning as in Formula (I); Y is O, N, S, or $CR_5$, in which $R_5$ has the same meaning as in Formula (I); n is 0 or 1; and the dashed circle in Formula (VII) indicates an aromatic or non-aromatic ring; or a salt, solvate, or hydrate thereof.

In certain embodiments of any of the Formulae I-IV and VI (or any formula herein), $R_6$ represents the non-carbonyl portion of an aldehyde shown in Table A, below (i.e., for an aldehyde of formula $R_6CHO$, $R_6$ is the non-carbonyl portion of the aldehyde). In certain embodiments, $R_4$ and $R_6$ together represent the non-carbonyl portion of a ketone shown in Table A (i.e., for a ketone of formula $R_6C(O)R_4$, $R_4$ and $R_6$ are the non-carbonyl portion of the ketone).

TABLE A

Plate 1

TABLE A-continued
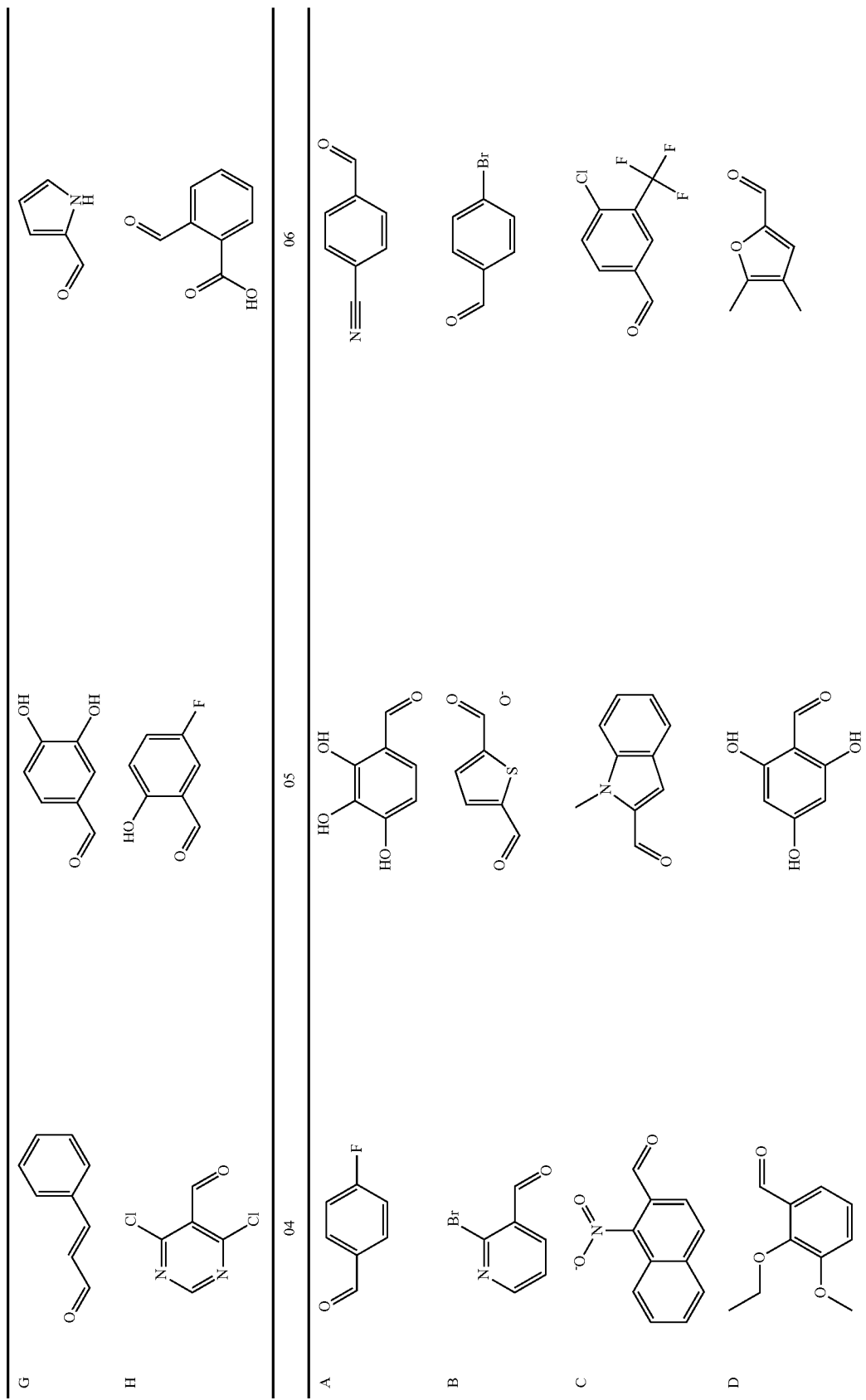

TABLE A-continued
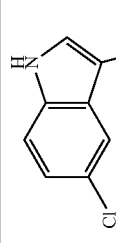

TABLE A-continued
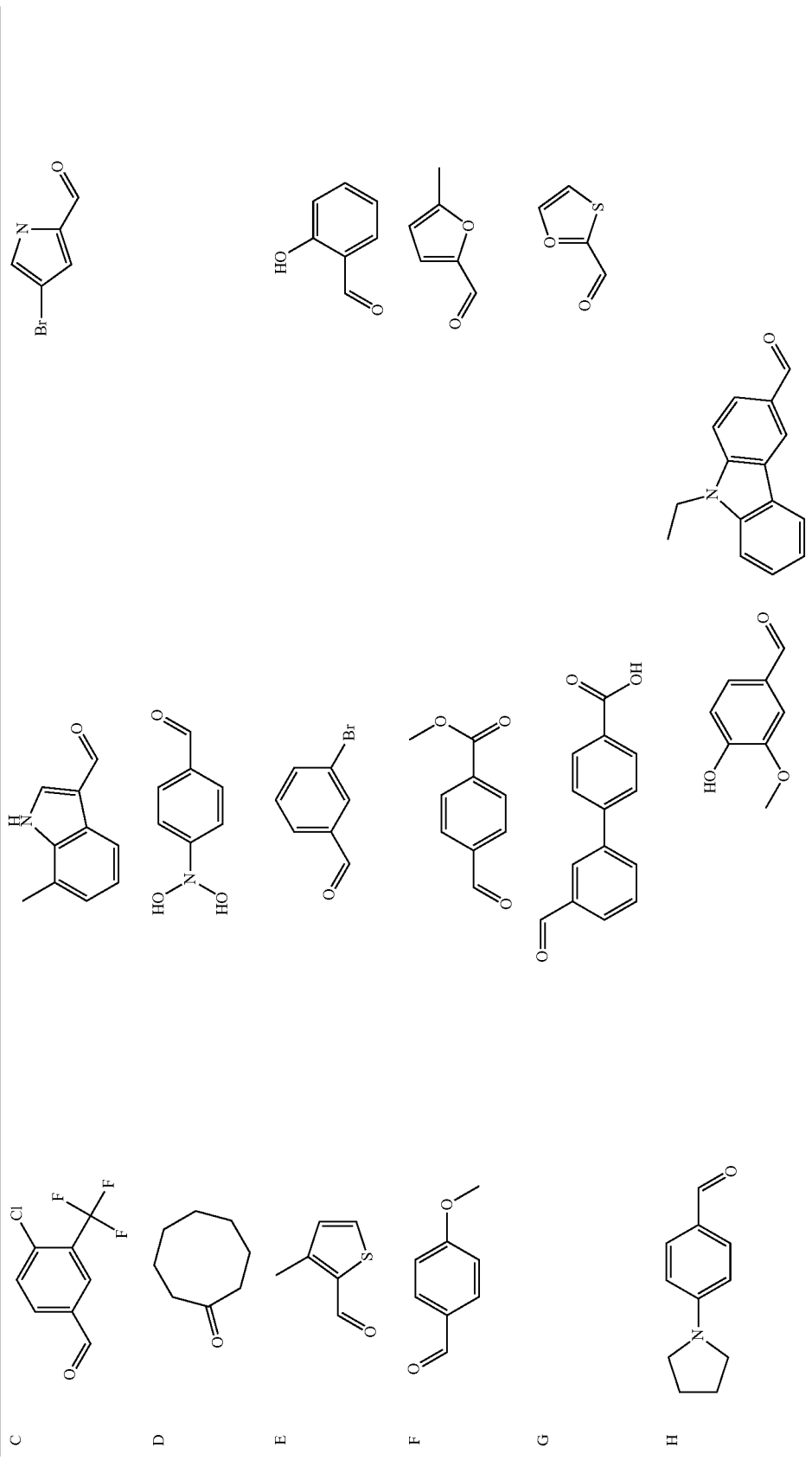

TABLE A-continued
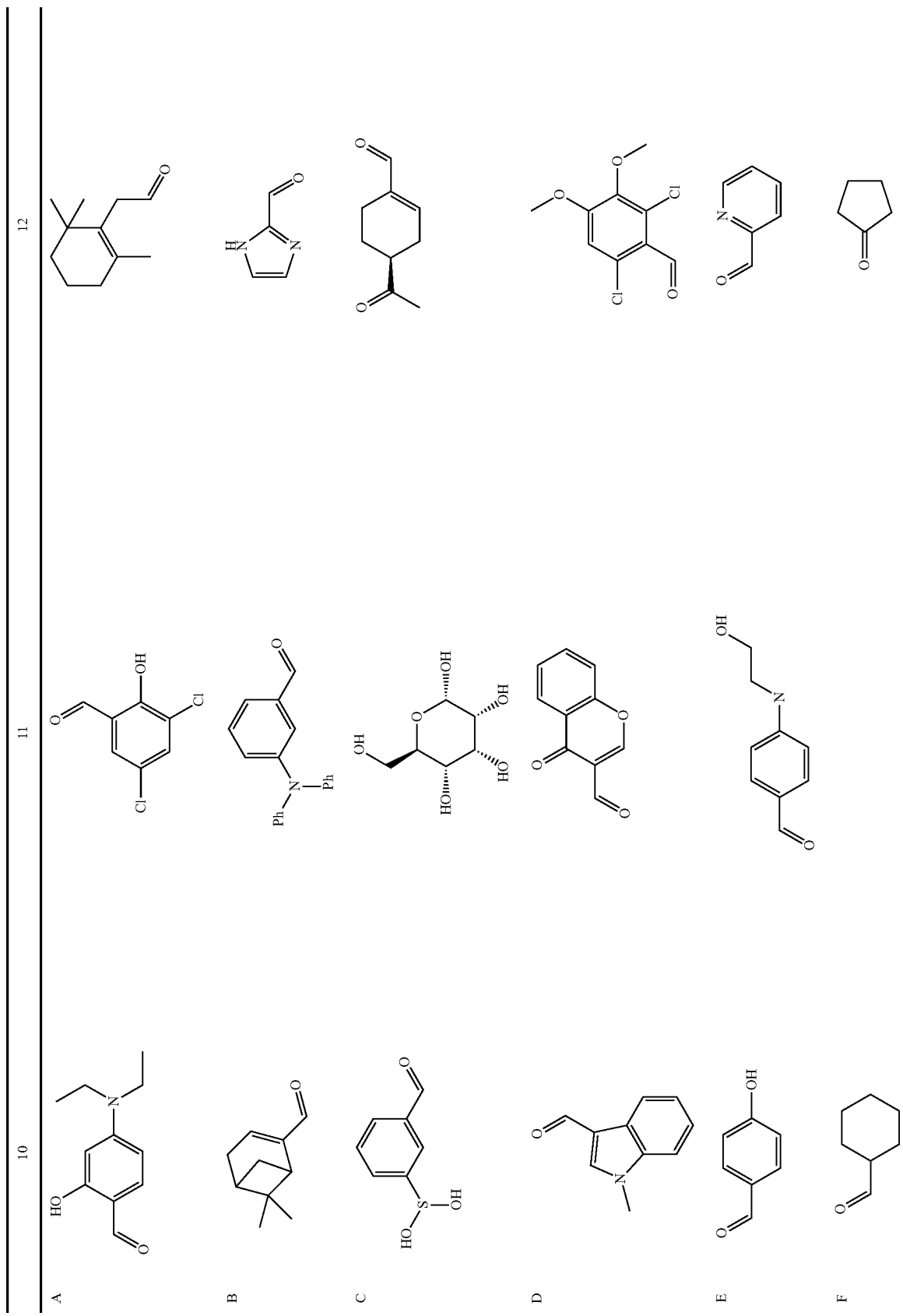

TABLE A-continued
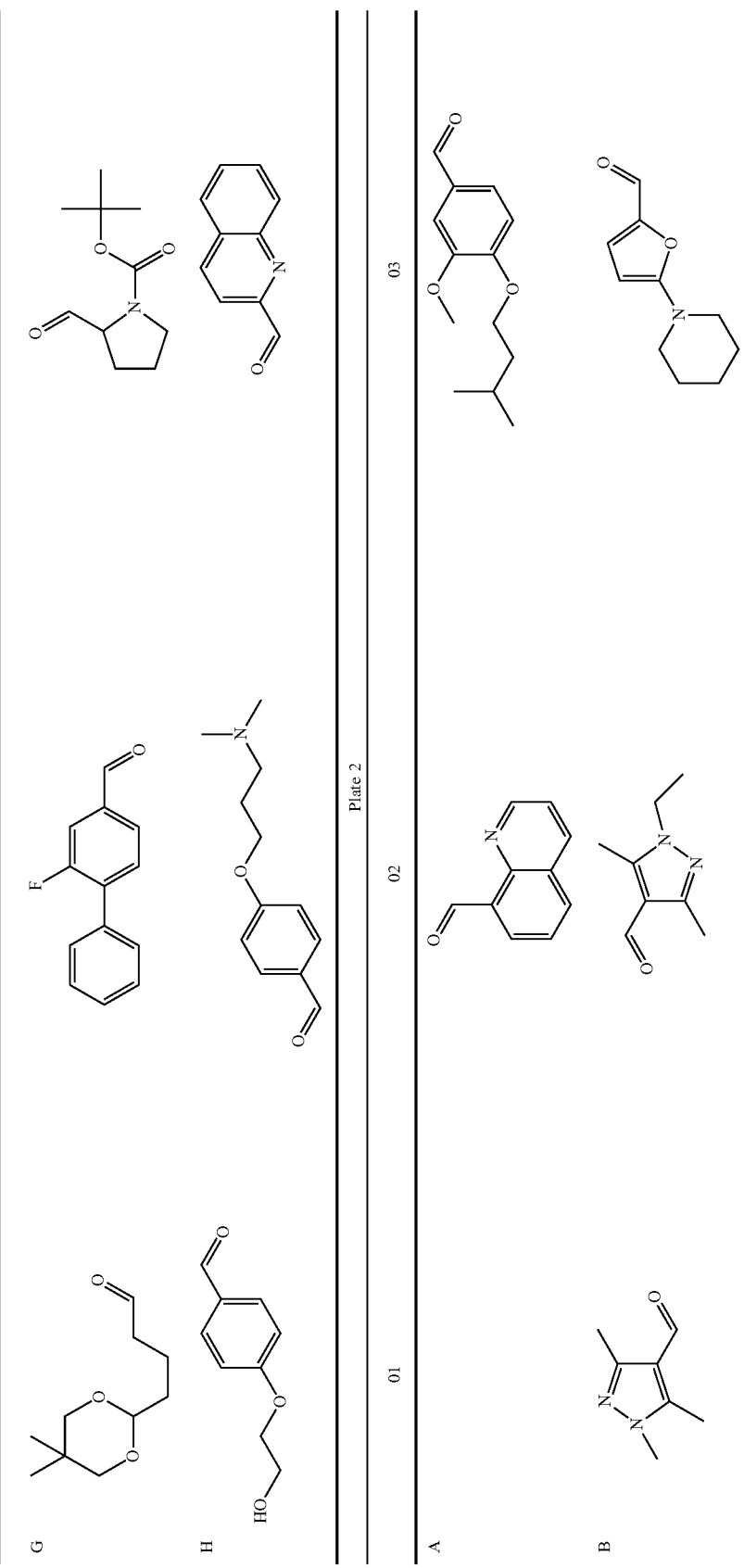

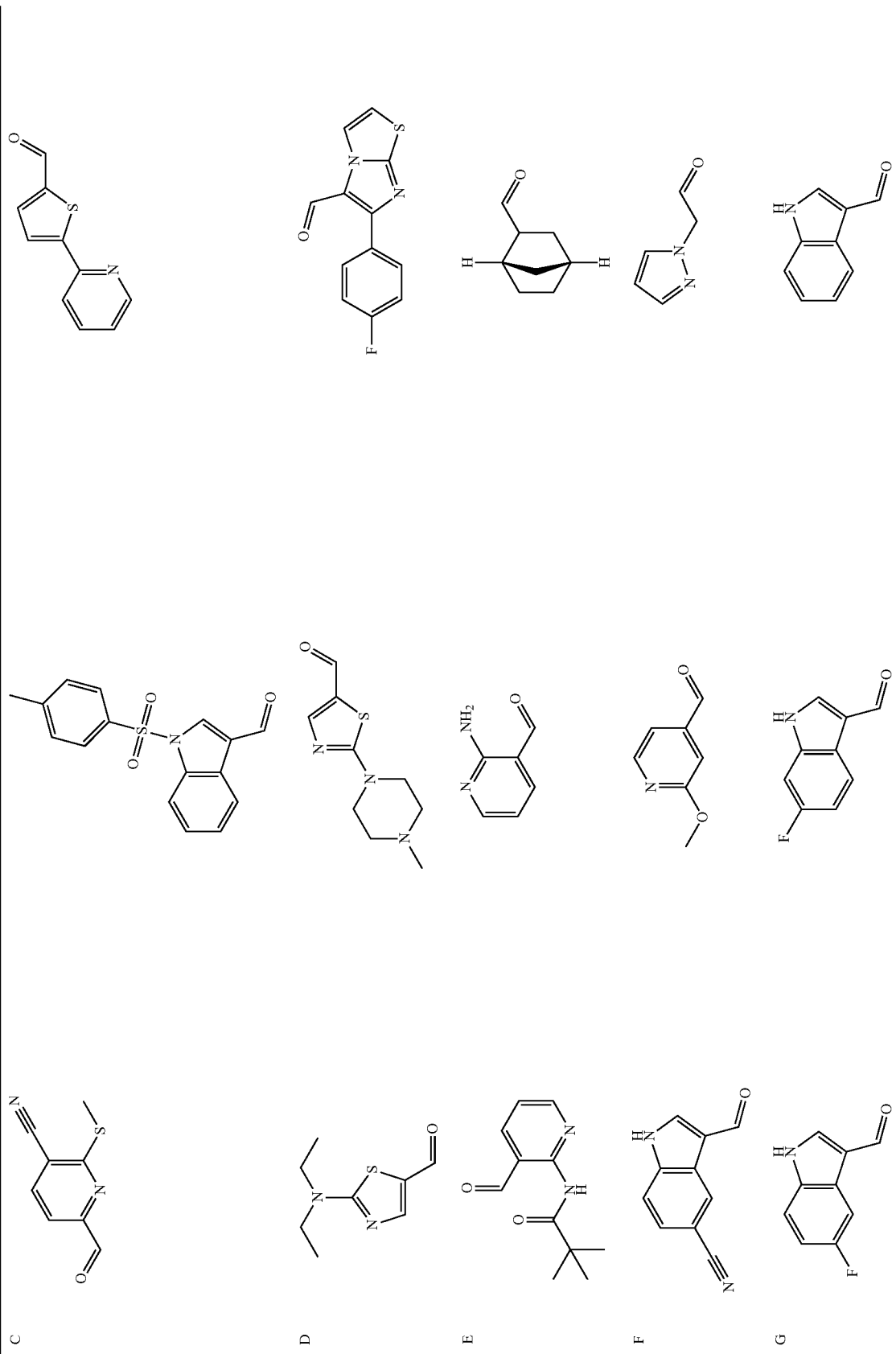

TABLE A-continued

TABLE A-continued
| | | | | | |
|---|---|---|---|---|---|
| F | 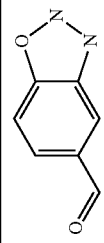 | 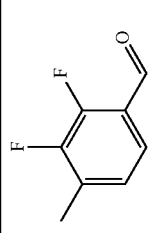 | 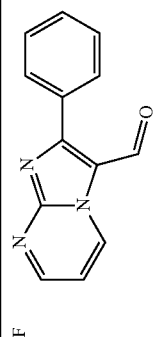 | | |
| G | 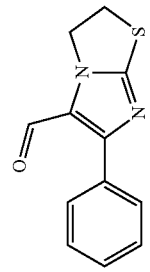 | 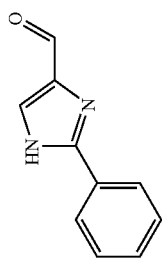 | 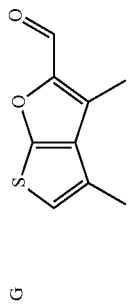 | | |
| H | 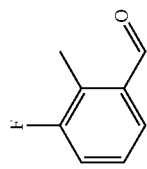 | 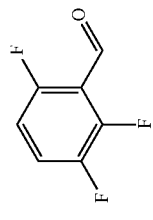 | 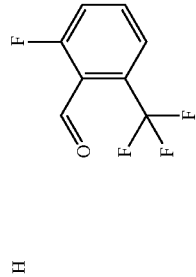 | | |
| | 07 | 08 | 09 | | |
| A | 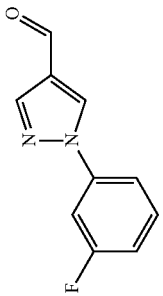 | | 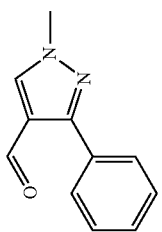 | | 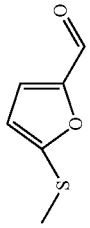 |
| B | 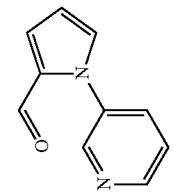 | | 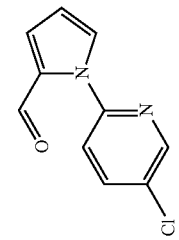 | | 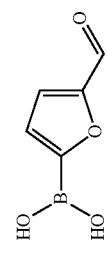 |
| C | 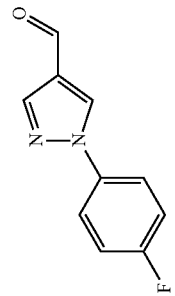 | | 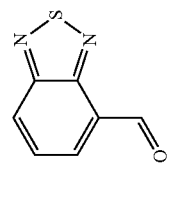 | | 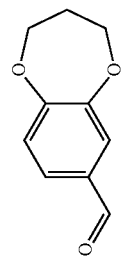 |

TABLE A-continued
| | | | | |
|---|---|---|---|---|
| D | 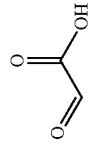 | 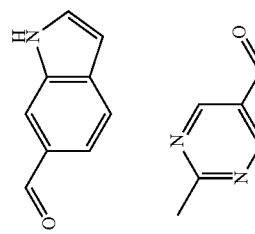 | 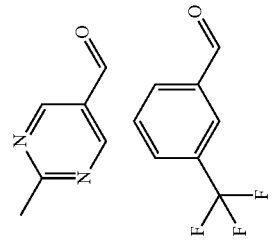 | 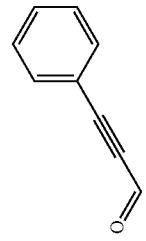 |
| E | | | | |
| F | | | | |
| G | 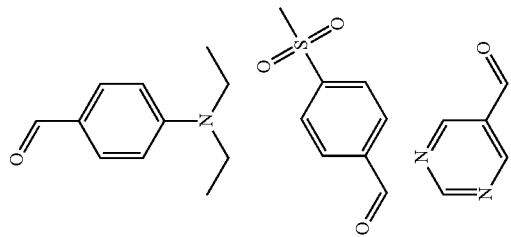 | | | |
| H | 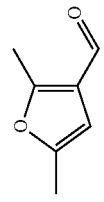 | 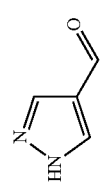 | 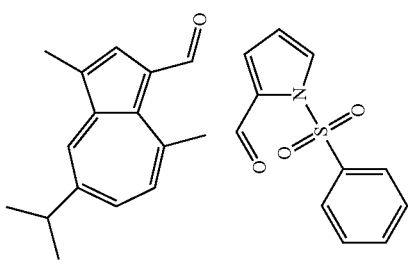 | |

TABLE A-continued
| | 10 | 11 | 12 |
|---|---|---|---|
| A | 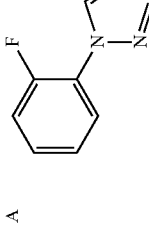 | 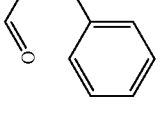 | 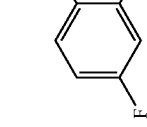 |
| B | 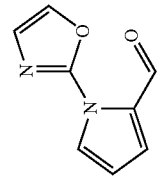 | 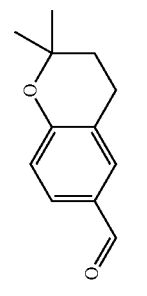 | 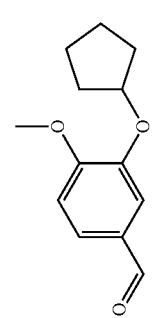 |
| C | 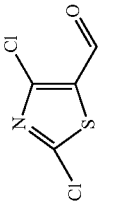 | 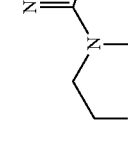 | 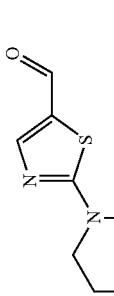 |
| D | 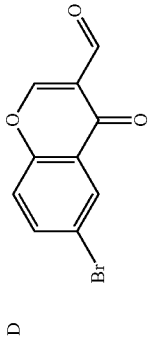 | 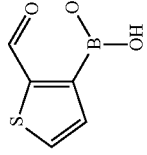 | 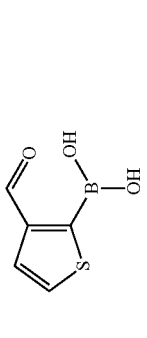 |
| E | 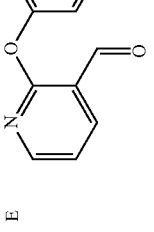 | 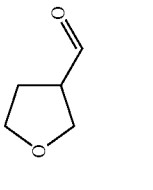 | 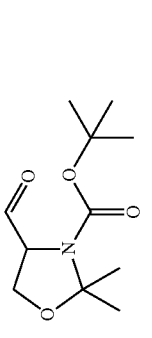 |
| F | 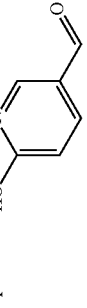 | | 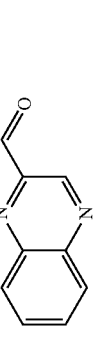 |

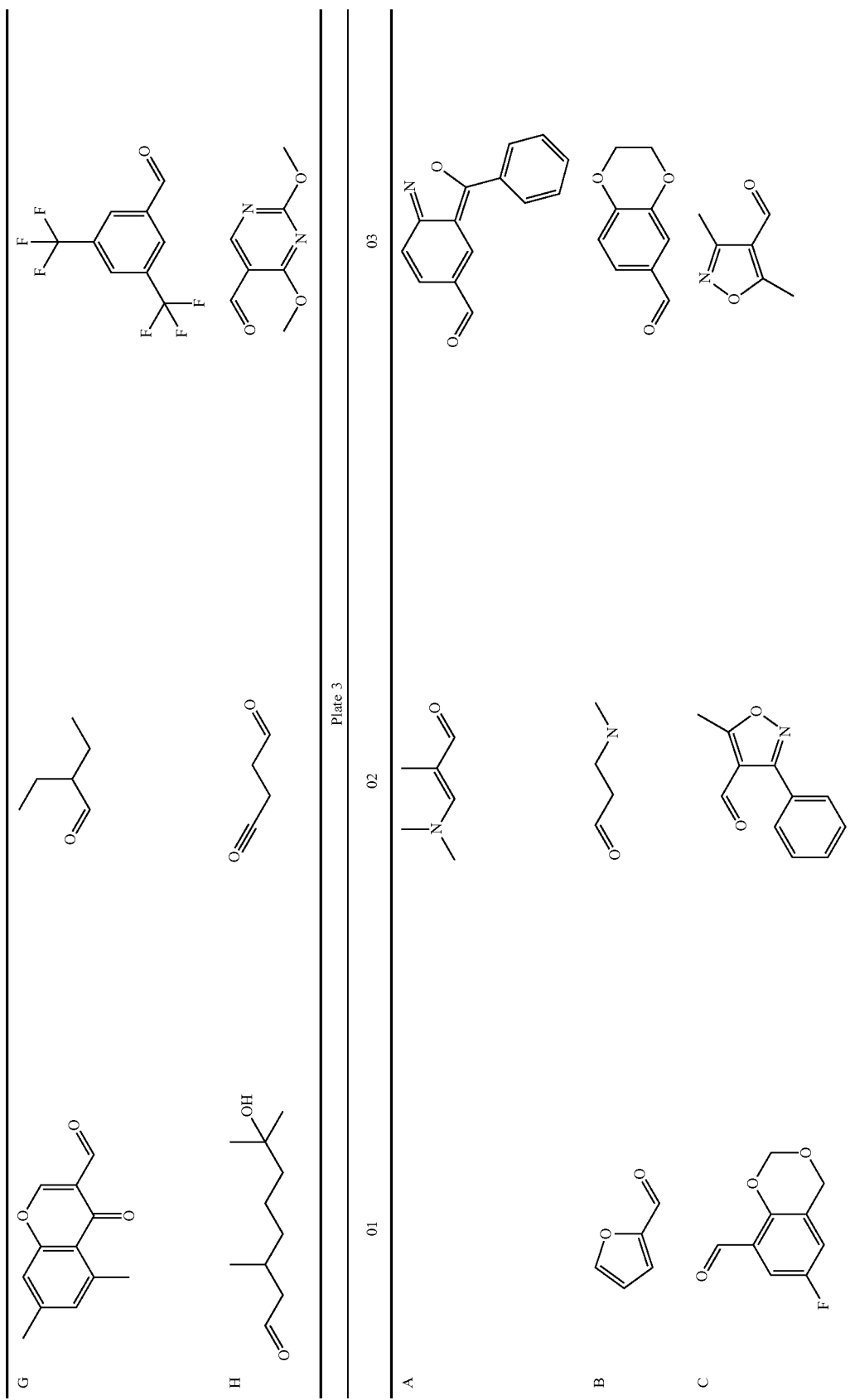

TABLE A-continued

TABLE A-continued
| | | | | | |
|---|---|---|---|---|---|
| B | 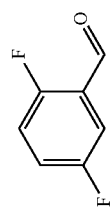 | 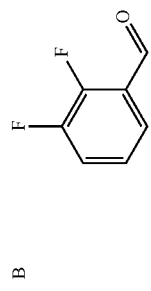 | | | |
| C | 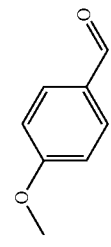 | 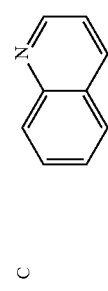 | | | |
| D | 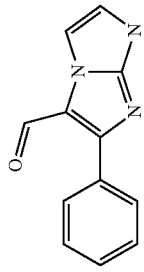 | 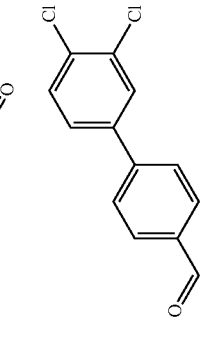 | | | |
| E | 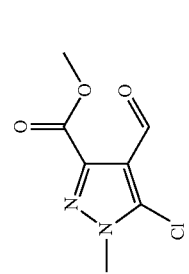 | 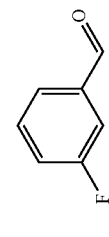 | | | |
| F | 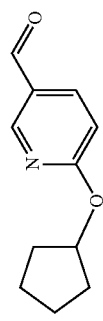 | 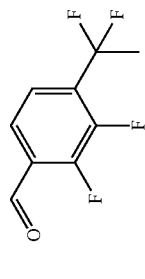 | | | |
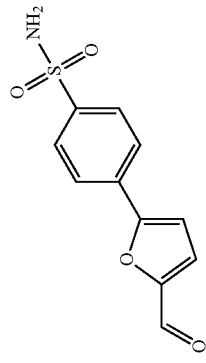
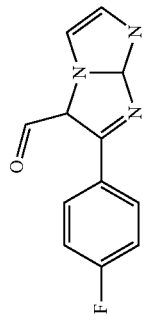
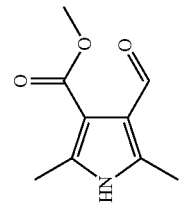
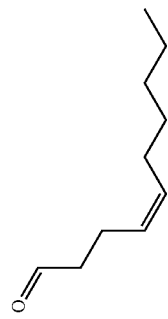

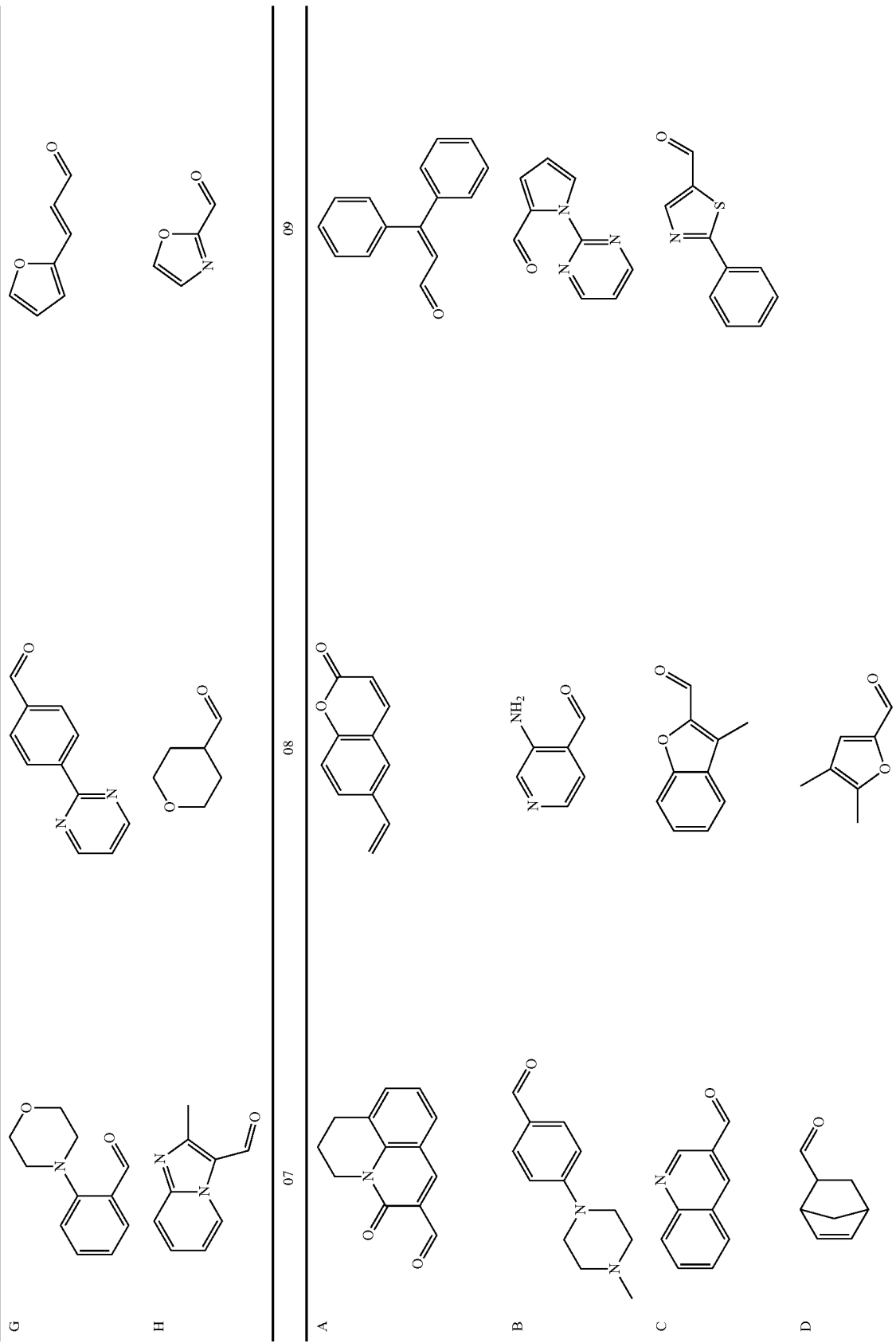

TABLE A-continued
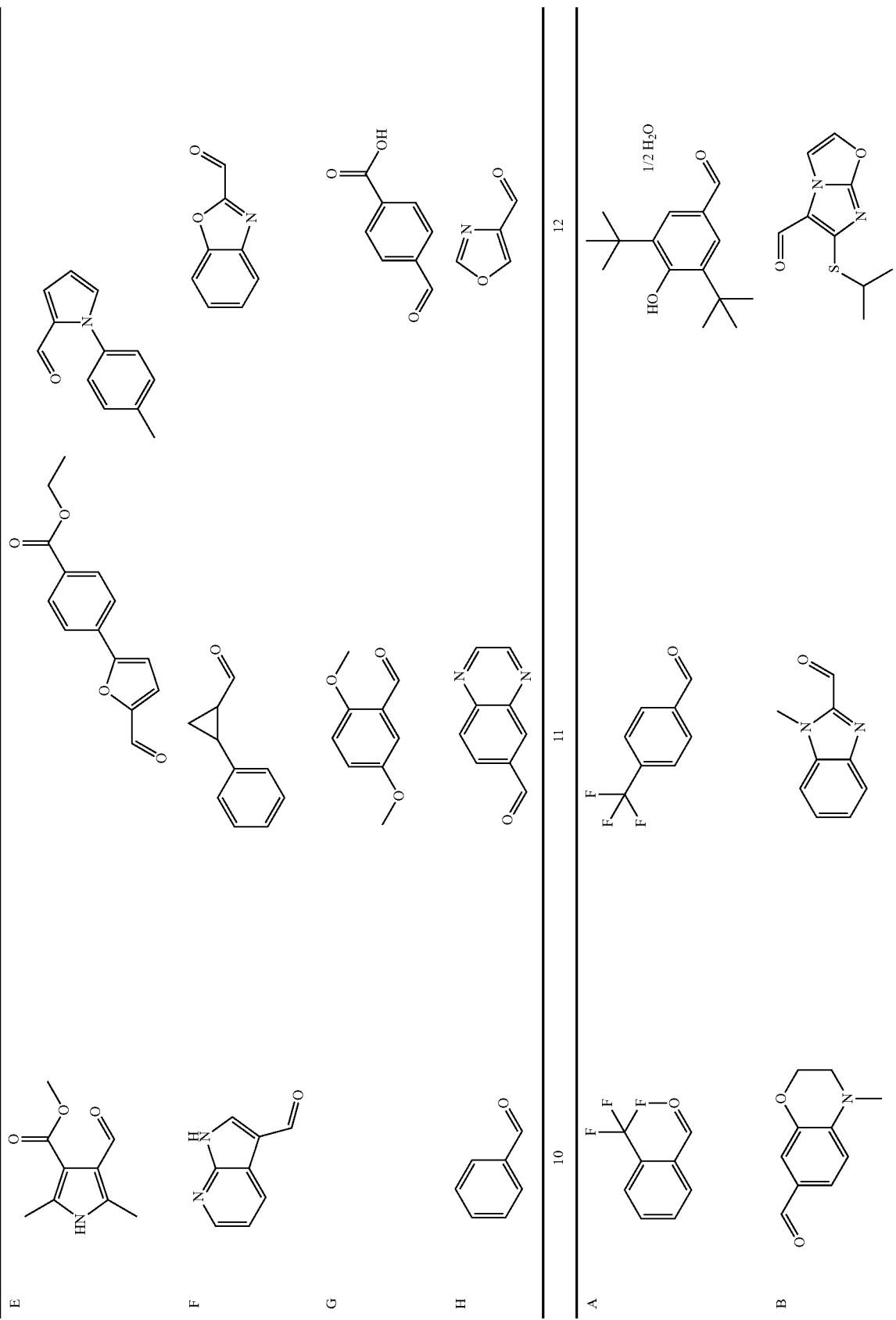

TABLE A-continued
| | | |
|---|---|---|
| C | 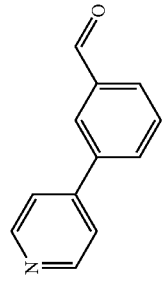 | 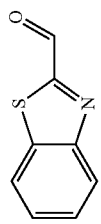 |
| D | | |
| E | | 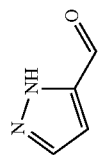 |
| F | | 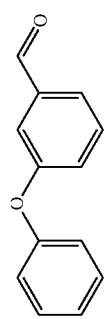 |
| G | | 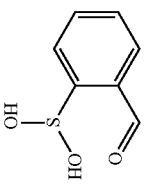 |
| H | | 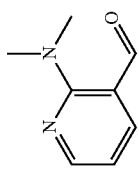 |

TABLE A-continued

Plate 4

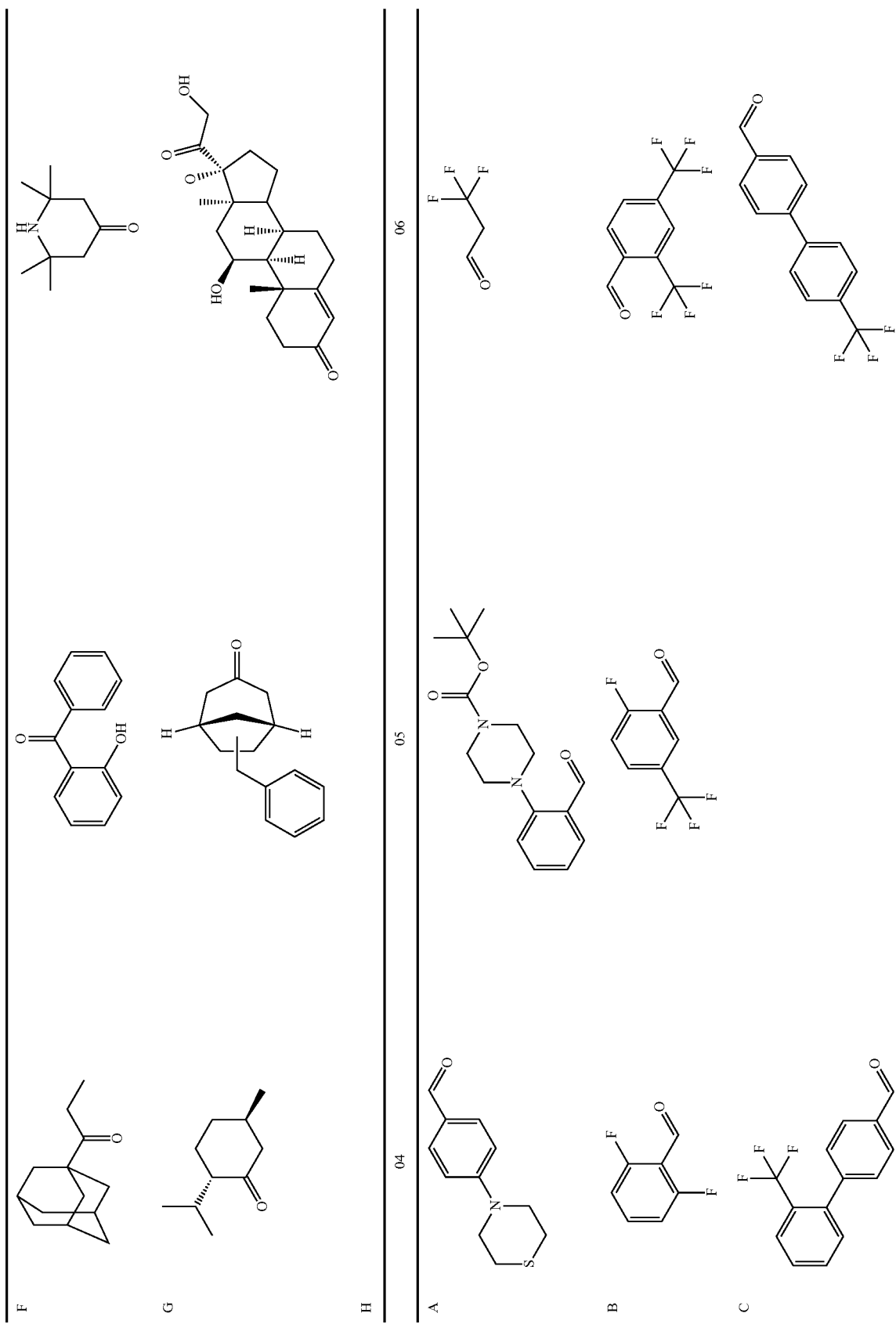

TABLE A-continued
| D | 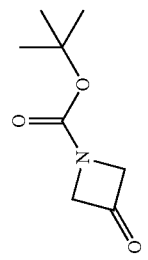 | 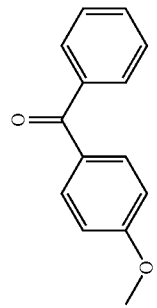 |
| E | 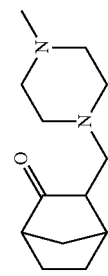 | 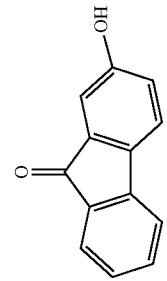 |
| F | 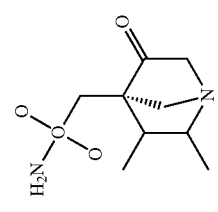 | 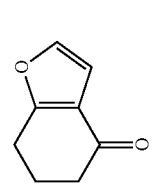 |
| G | 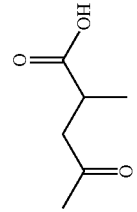 | 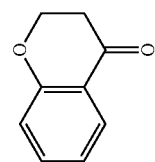 |
| H | | 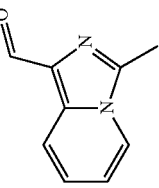 |
| | 07 | 08 | 09 |
|---|---|---|---|
| A | 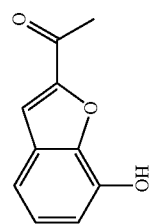 | 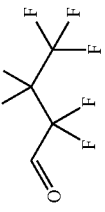 | |

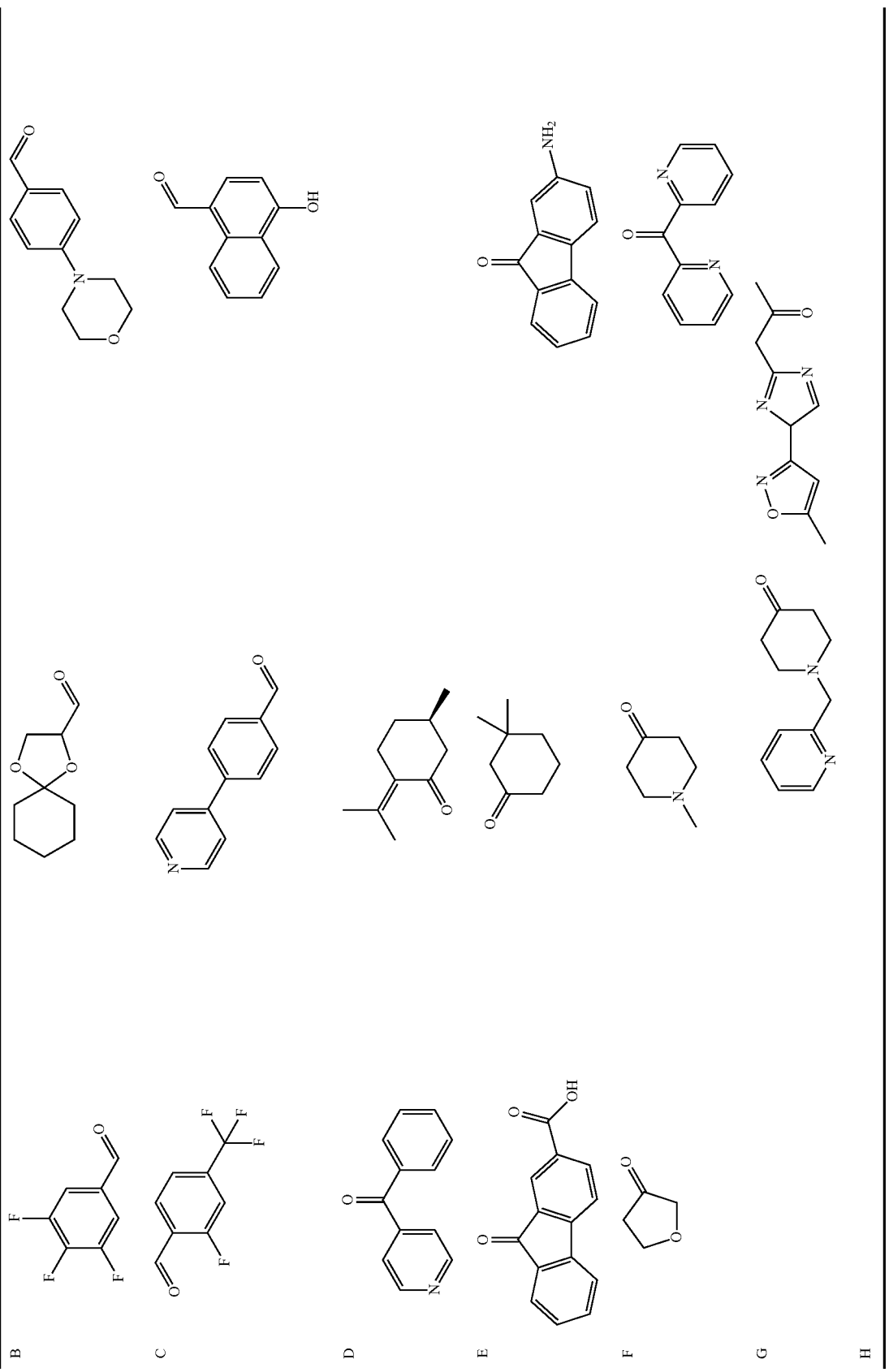

TABLE A-continued
| | 10 | 11 | 12 |
|---|---|---|---|
| A | 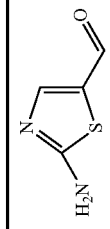 | 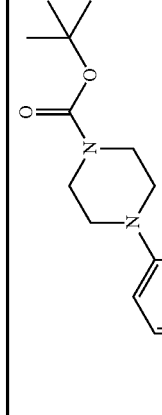 | 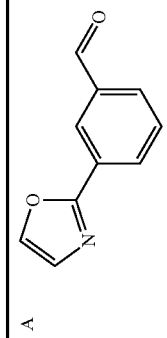 |
| B | 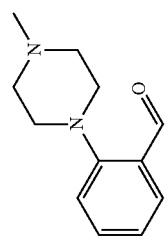 | 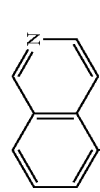 | 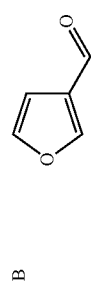 |
| C | 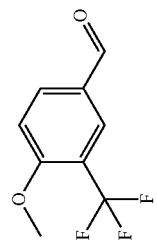 | 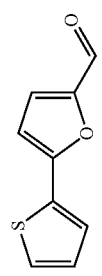 | 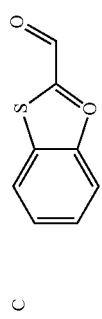 |
| D | 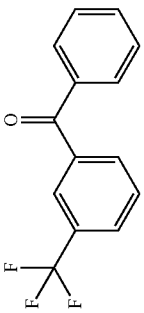 | 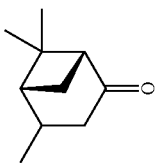 | 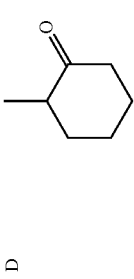 |
| E | 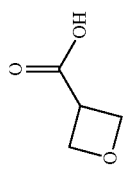 | 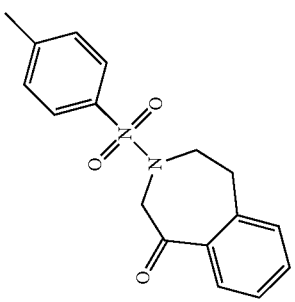 | 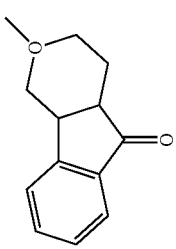 |

TABLE A-continued
| F | 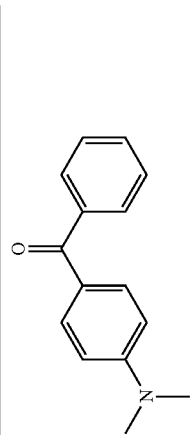 |
| G |  |
| H | 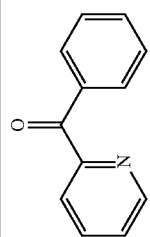 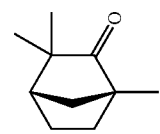 |

In one embodiment, the compound is a compound is represented by the formula:

(VIII)

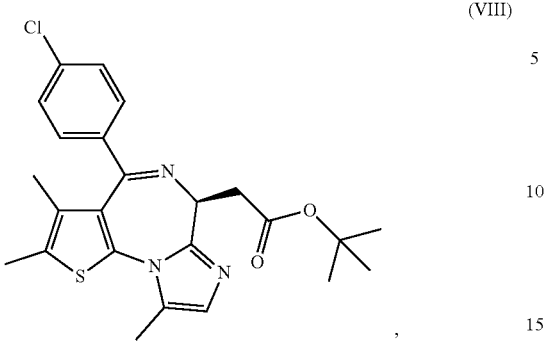

or a salt, solvate, or hydrate thereof.

In certain embodiments, the compound is (racemic) JQ1; in certain embodiments, the compound is (+)-JQ1. In certain embodiments, the compound is a compound selected from the group consisting of:

(3)

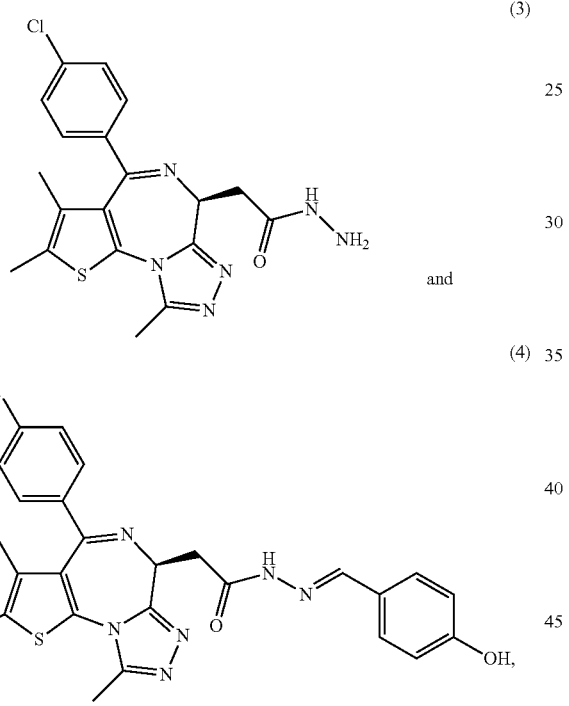

and (4)

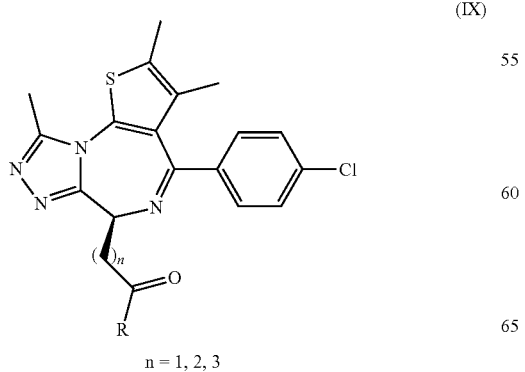

or a salt, solvate, or hydrate thereof.

Additional examples of compounds include compounds according to any of the follow formulae:

(IX)

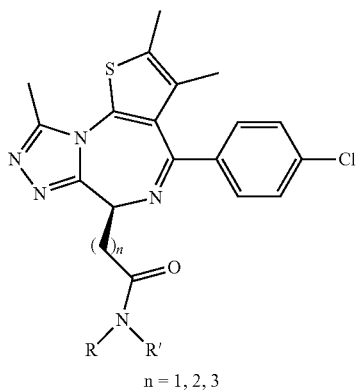

n = 1, 2, 3

(X)

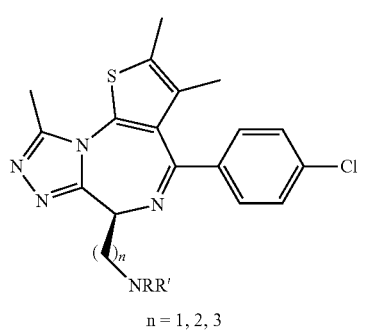

n = 1, 2, 3

(XI)

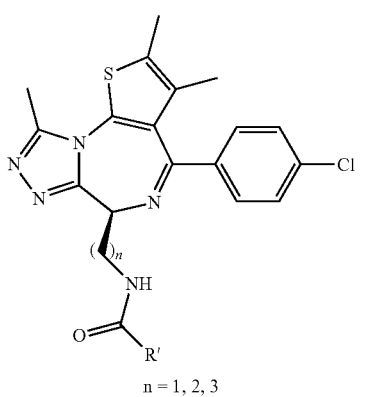

n = 1, 2, 3

(XII)

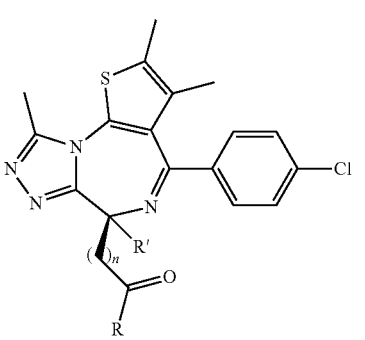

n = 1, 2, 3

(XIII)

n = 1, 2, 3
R' = H, D, Me

-continued (XIV)
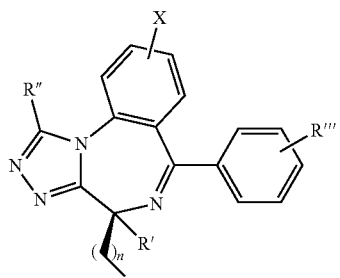
R' = H, D, Me
n = 1, 2, 3

(XV)
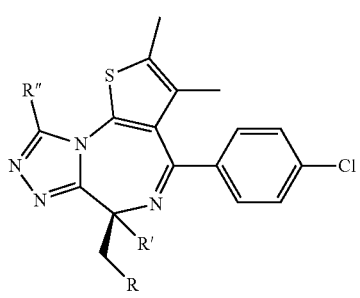
R' = OMe, CH2OH, CH2NH2, CH2OMe (XVI)
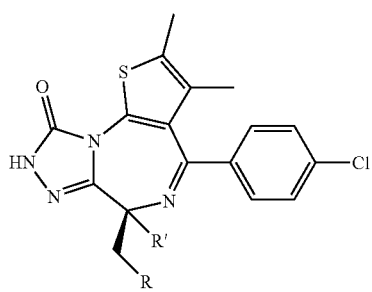

(XVII)
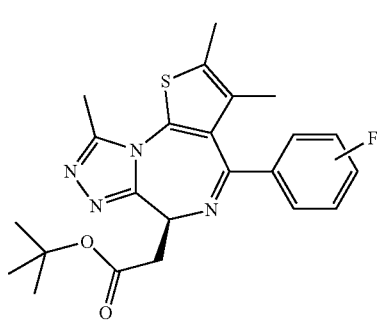

(XVIII)
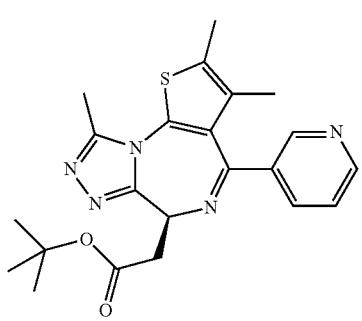
Also 2- and 4-pyridyl

-continued (XIX)
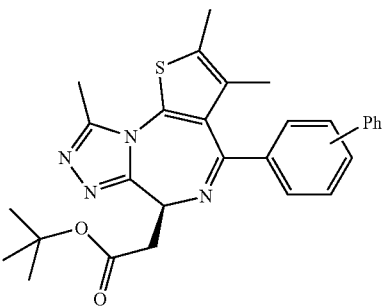

(XX)
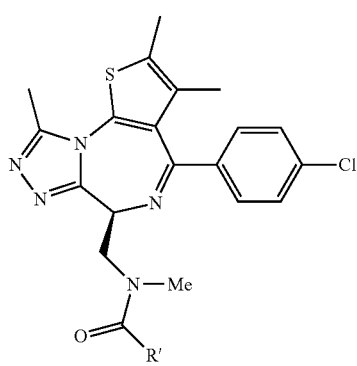

(XXI)
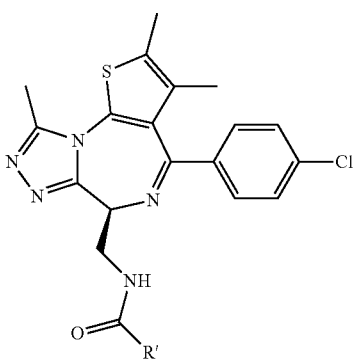

(XXII)
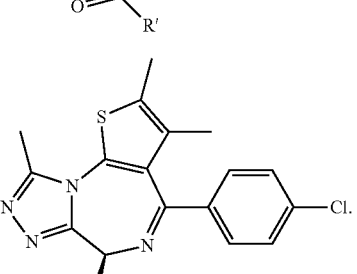
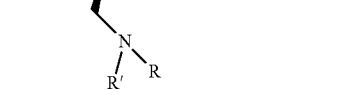

In Formulae IX-XXII, R and R' can be, e.g., H, aryl, substituted aryl, heteroaryl, heteroaryl, heterocycloalkyl, —$C_1$-$C_8$ alkyl, —$C_2$-$C_8$ alkenyl, —$C_2$-$C_8$ alkynyl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted. In Formulae XIV, X can be any substituent for an aryl group as described herein.

Compounds of the invention can be prepared by a variety of methods, some of which are known in the art. For instance, the chemical Examples provided hereinbelow provide synthetic schemes for the preparation of the compound JQ1 (as the racemate) and the enantiomers (+)-JQ1 and (−)-JQ1 (see Schemes S1 and S2). A variety of compounds of Formulae (I)-(VIII) can be prepared by analogous methods with substitution of appropriate starting materials.

For example, starting from JQ1, the analogous amine can be prepared as shown in Scheme 1, below.

Scheme 1

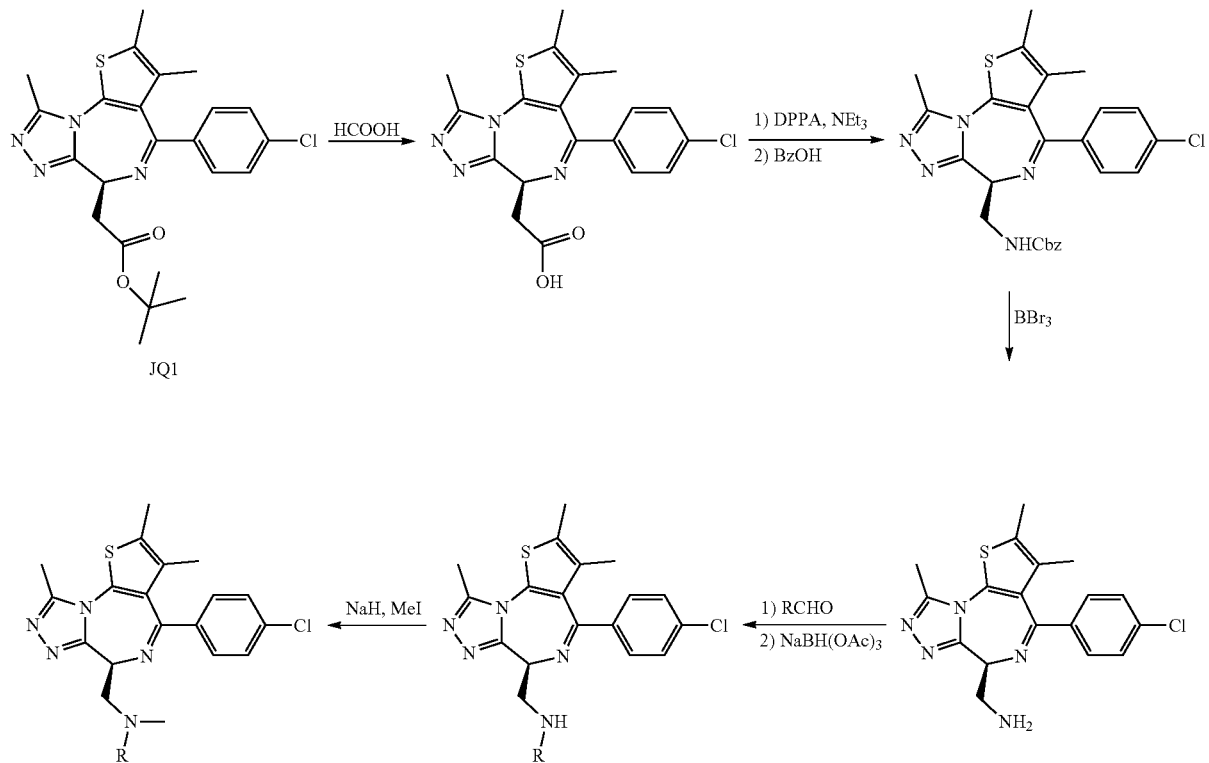

As shown in Scheme 1, hydrolysis of the t-butyl ester of JQ1 affords the carboxylic acid, which is treated with diphenylphosphoryl azide (DPPA) and subjected to Curtius rearrangement conditions to provide the Cbz-protected amine, which is then deprotected to yield the amine. Subsequent elaboration of the amine group, e.g., by reductive amination yields secondary amines, which can be further alkylated to provide tertiary amines.

Scheme 2

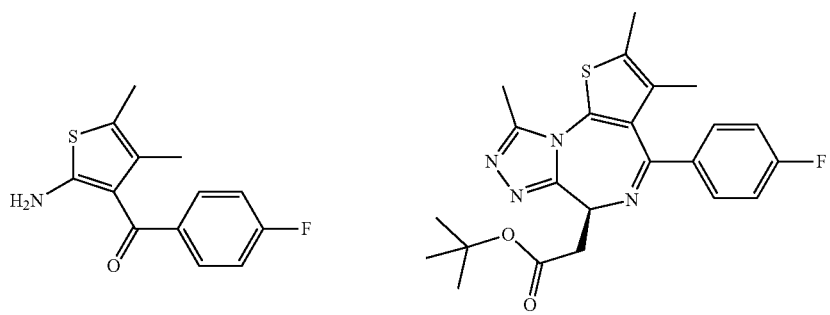

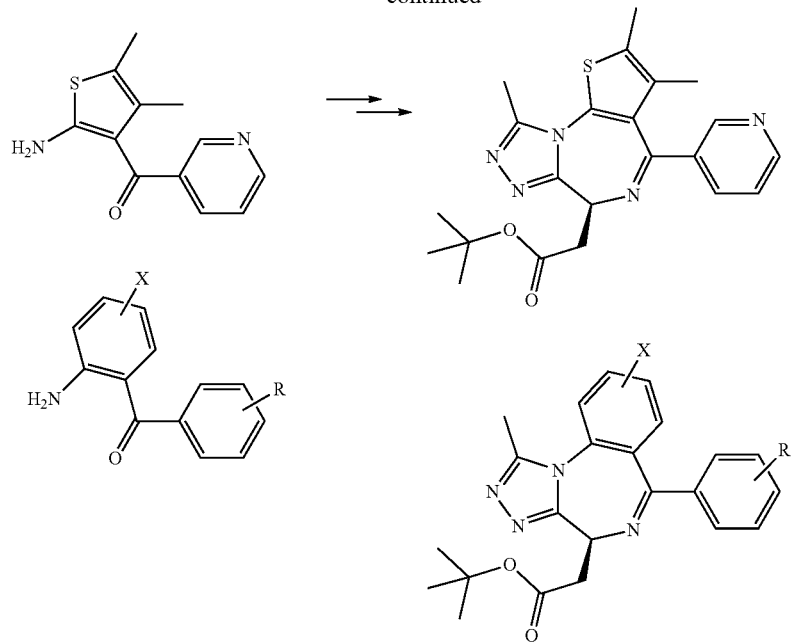

Scheme 2 shows the synthesis of further examples of the compounds of the invention, e.g., of Formula I, in which the fused ring core is modified (e.g., by substitution of a different aromatic ring as Ring A in Formula I). Use of aminodiarylketones having appropriate functionality (e.g., in place of the aminodiarylketone S2 in Scheme S1, infra) provides new compounds having a variety of fused ring cores and/or aryl group appendages (corresponding to group R in Formula I). Such aminodiarylketones are commercially available or can be prepared by a variety of methods, some of which are known in the art.

Scheme 3 provides additional exemplary synthetic schemes for preparing further compounds of the invention.

Scheme 3

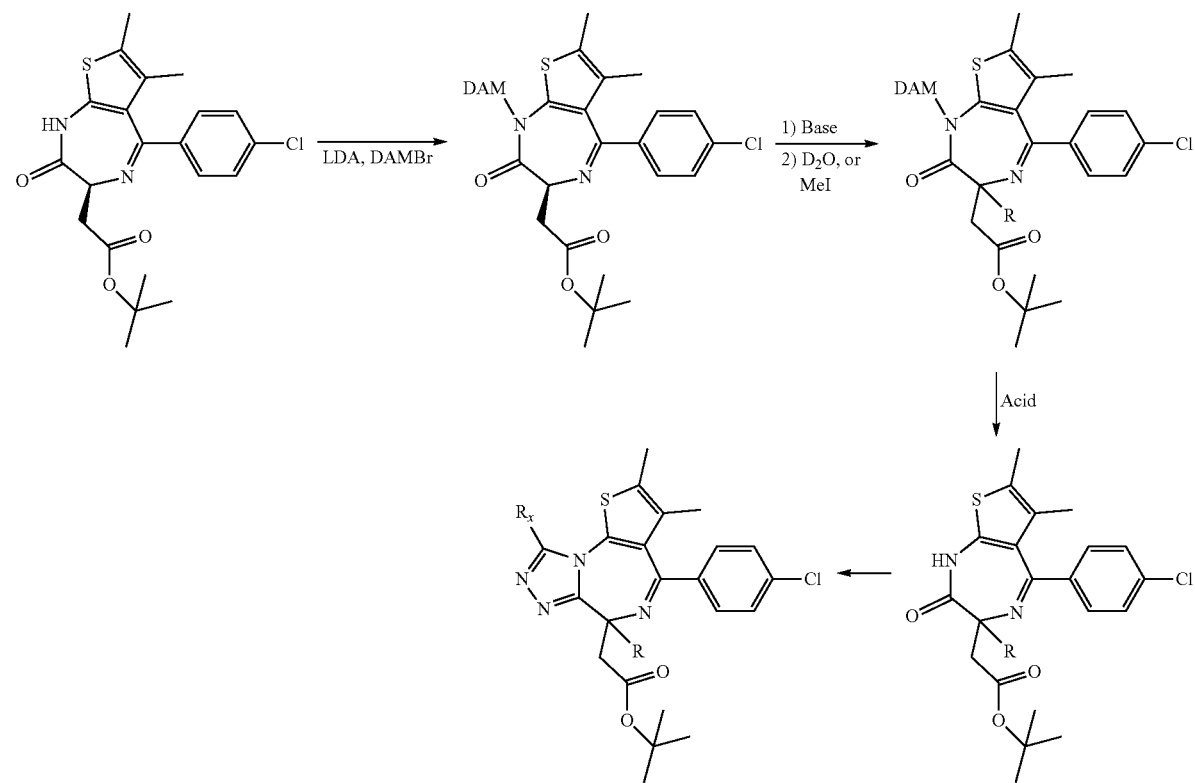

As shown in Scheme 3, a fused bicyclic precursor (see Scheme S1, infra, for synthesis of this compound) is functionalized with a moiety R (DAM=dimethylaminomethylene protecting group) and then elaborated by reaction with a hydrazide to form the tricyclic fused core. Substituent $R_x$ can be varied by selection of a suitable hydrazide.

Additional examples of compounds of the invention (which can be prepared by the methods described herein) include:

Amides:

Amides can be prepared, e.g., by preparation of a corresponding carboxylic acid or ester, followed by amidation with an appropriate amine using standard conditions. In certain embodiments, an amide provides a two-carbon "linker" with a terminal nitrogen-containing ring (e.g., pyridyl, piperidyl, piperazinyl, imidazolyl (including N-methyl-imidazolyl), morpholinyl, and the like. Exemplary amide structures include:

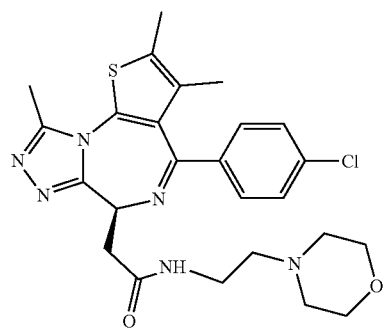

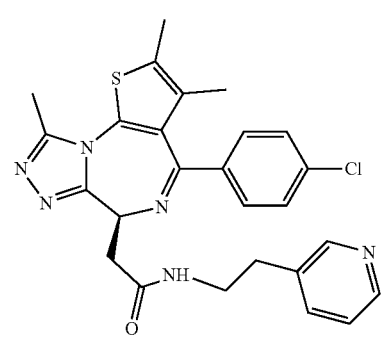

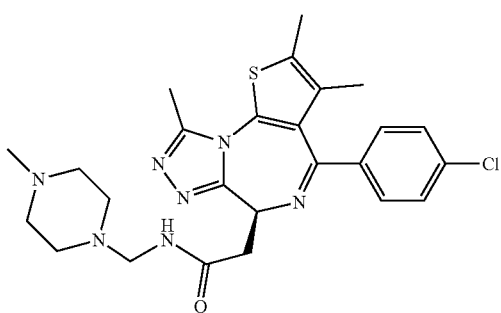

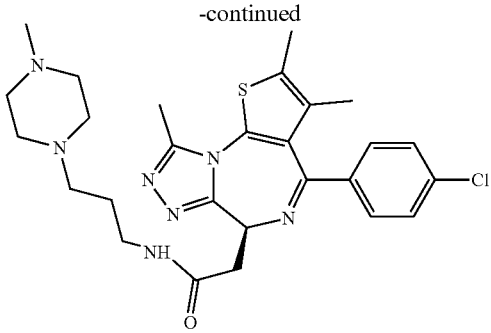

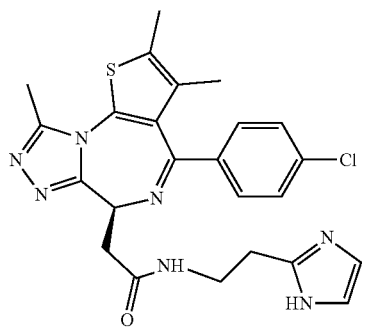

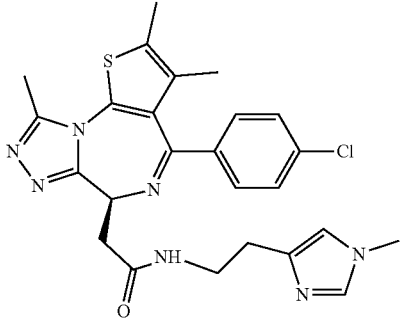

The use of a two-carbon linker between the amide moiety and the terminal nitrogen-containing ring is preferred.

"Reverse Amides":

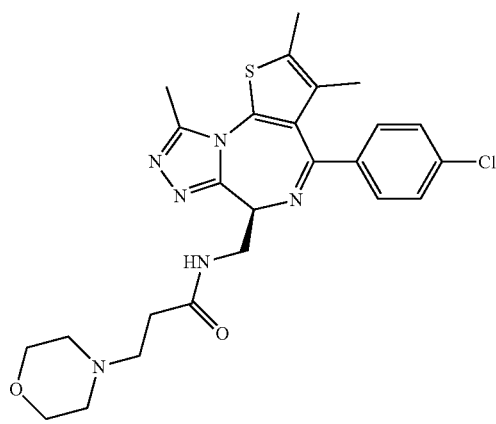

| 101 | 102 |
|---|---|
| -continued | -continued |
| 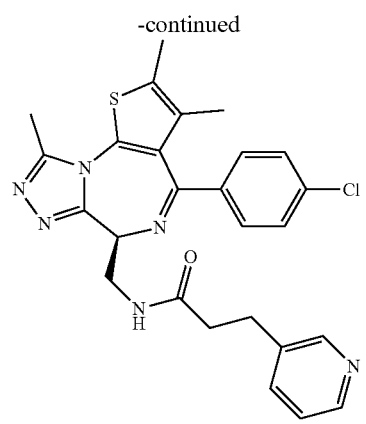 | 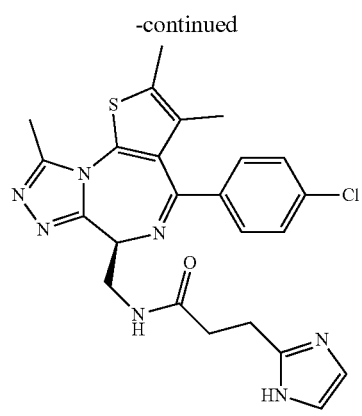 |
| N position can be different | |
| 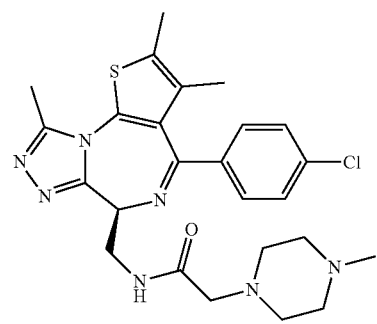 | 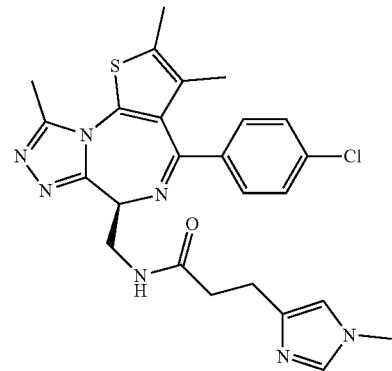 |
| | Secondary Amines: |
| 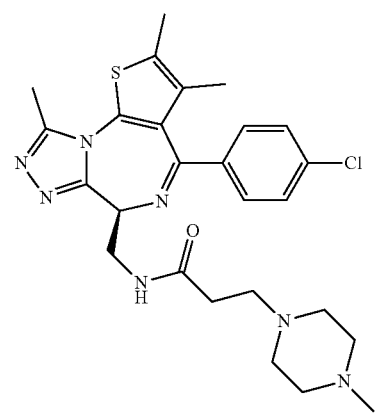 | 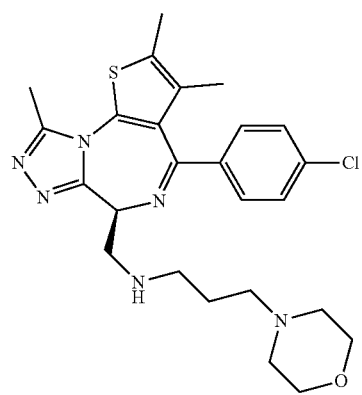 |
| 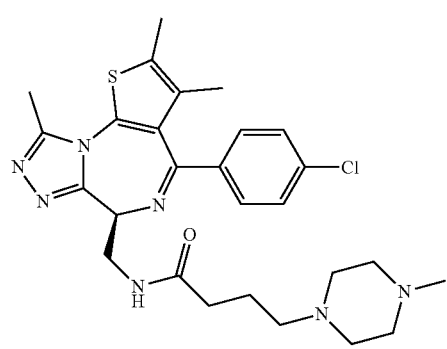 | 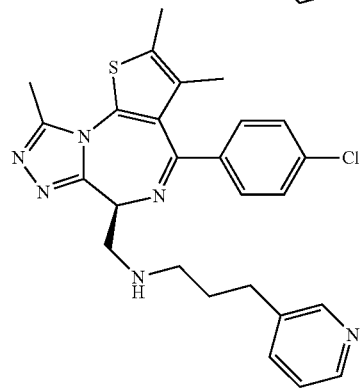 |

-continued

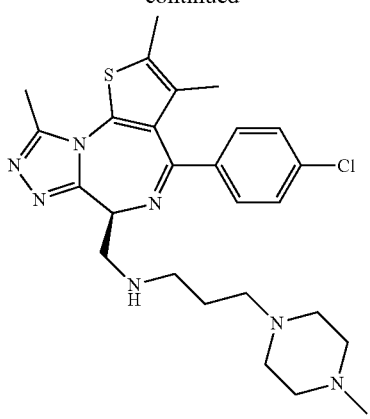

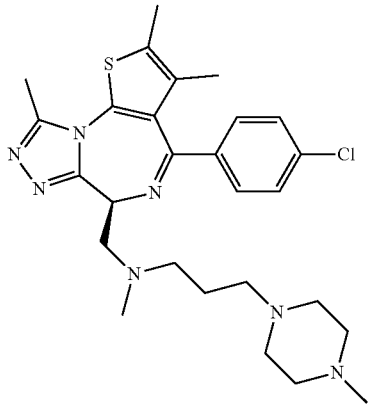

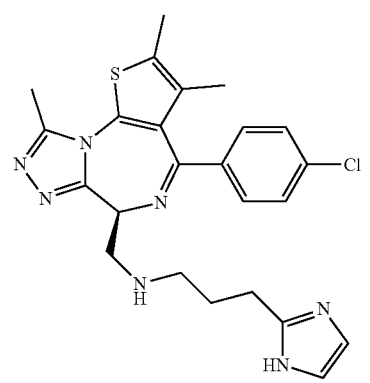 [SMILES: Cc1sc2c(c1C)C(c1ccc(Cl)cc1)=N[C@@H](CNCCCc1ncc[nH]1)c1nnc(C)n1-2]

Boronic Acids:

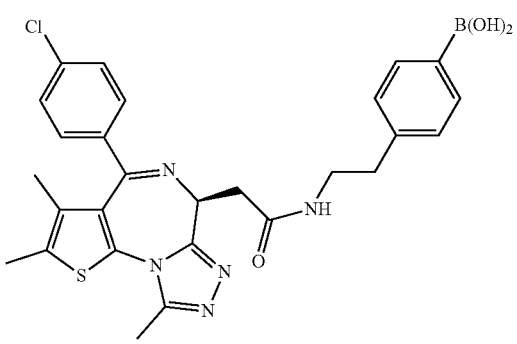

-continued

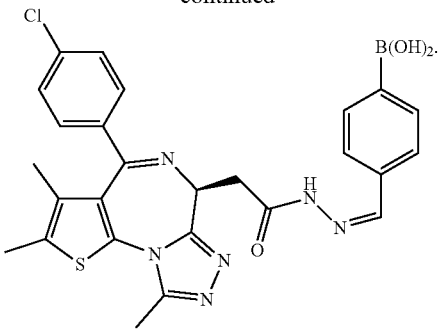

In certain embodiments, a compound having at least one chiral center is present in racemic form. In certain embodiments, a compound having at least one chiral center is enantiomerically enriched, i.e., has an enantiomeric excess (e.e.) of at least about 10%, 20%, 30%, 40%, 50%, 60%, 70%, 80%, 85%, 90%, 90%, 95%, 99%, 99% or 100%. In certain embodiments, a compound has the same absolute configuration as the compound (+)-JQ1 ((S)-tert-Butyl 2-(4-(4-chlorophenyl)-2,3,9-trimethyl-6H-thieno[3,2-f][1,2,4]triazolo[4,3-a][1,4]diazepin-6-yl)acetate) described herein.

In certain embodiments of any of the Formulae disclosed herein, the compound is not represented by the following structure:

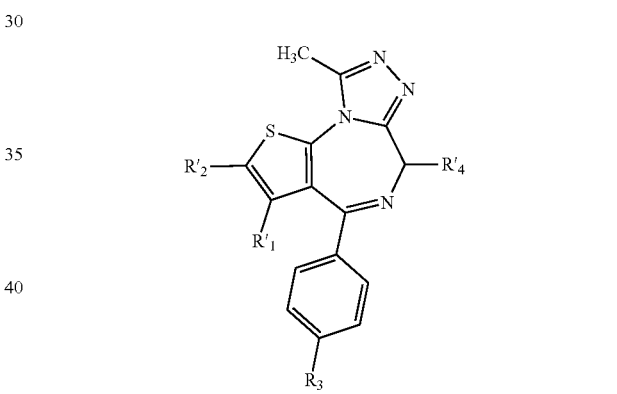

in which:

$R'_1$ is $C_1$-$C_4$ alkyl;

$R'_2$ is hydrogen, halogen, or $C_1$-$C_4$ alkyl optionally substituted with a halogen atom or a hydroxyl group;

$R'_3$ is a halogen atom, phenyl optionally substituted by a halogen atom, $C_1$-$C_4$ alkyl, $C_1$-$C_4$ alkoxy, or cyano; —$NR_5$—$(CH_2)_m$—$R_6$ wherein $R_5$ is a hydrogen atom or $C_1$-$C_4$ alkyl, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or $C_1$-$C_4$ alkyl, n is an integer of 0-2, and $R_8$ is phenyl or pyridyl optionally substituted by a halogen atom; and $R'_4$ is —$(CH_2)_a$—CO—NH—$R_9$ wherein a is an integer of 1-4, and $R_9$ is $C_1$-$C_4$ alkyl; $C_1$-$C_4$ hydroxyalkyl; $C_1$-$C_4$ alkoxy; or phenyl or pyridyl optionally substituted by $C_1$-$C_4$ alkyl, $C_1$-$C_4$ alkoxy, amino or a hydroxyl group or —$(CH_2)_b$—$COOR_{10}$ wherein b is an integer of 1-4, and $R_{10}$ is $C_1$-$C_4$ alkyl.

The term "pharmaceutically acceptable salt" also refers to a salt prepared from a compound disclosed herein (e.g., JQ1, a compound of Formulas I-XXII) or any other compound delineated herein, having an acidic functional group, such as a carboxylic acid functional group, and a pharmaceutically acceptable inorganic, or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, or any other compound delineated herein, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, glucosic acid, glucaronic acid, saccharic acid, formic acid, benzoic acid, glutamic acid, methanesulfonic acid, ethanesulfonic acid, benzenesulfonic acid, and p-toluenesulfonic acid.

Methods of the Invention

The present invention also relates to using the novel compounds described herein, as well as other inhibitors of BRDT as male contraceptives. Such compounds are known in the art and described, for example, in WO2009084693 or corresponding US2010286127.

Thus, in one aspect, the invention provides methods for reducing or inhibiting spermatozoa emission involving administering an effective amount of a BRDT inhibitor to a male subject. In embodiments, the inhibitor is a compound having a formula delineated herein, a derivative thereof, or a pharmaceutically acceptable salt or prodrug thereof.

In embodiments, the methods involve administering the inhibitor in an amount sufficient to suppress spermatogenesis.

In embodiments, the methods involve administering the inhibitor in an amount sufficient to induce azoospermia or oligozoospermia.

In embodiments, the methods involve administering the inhibitor in an amount sufficient to lower the spermatozoa concentration to not more than 3 million/mL, 2 million/mL, 1 million/mL, 0.5 million/mL, 0.25 million/mL, or 0.1 million/mL. In related embodiments, the methods involve administering the inhibitor in an amount sufficient to lower the spermatozoa concentration to not more than 0.1 million/mL.

In embodiments, the inhibitor is administered in combination with a pharmaceutically acceptable carrier, excipient, or diluent.

In embodiments, the inhibitor is administered to the subject orally, transdermally, or by injection. In related embodiments, the inhibitor is administered in the form of a tablet or capsule. In related embodiments, the inhibitor is administered by parenteral injection, intramuscular injection, intravenous injection, subcutaneous implantation, subcutaneous injection, or transdermal preparation.

In embodiments, the inhibitor is used in combination with at least one additional male contraceptive agent or device. In related embodiments, the additional male contraceptive is a condom. In other related embodiments, the additional male contraceptive is a modulator of testosterone production, androgen receptor function or stability.

Pharmaceutical Compositions

The invention features pharmaceutical compositions that contain one or more of the compounds described herein, a derivative thereof, or a pharmaceutically acceptable salt or prodrug thereof as the active ingredient(s). The pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopeia, European Pharmacopeia or other generally recognized pharmacopeia for use in mammals, and more particularly in humans. These compositions can be useful as a male contraceptive.

A thorough discussion of pharmaceutically acceptable carriers, diluents, and other excipients is presented in *Remington's Pharmaceutical Sciences* (17th ed., Mack Publishing Company) and *Remington: The Science and Practice of Pharmacy* (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited, to saline, buffered saline, dextrose, water, glycerol, ethanol, sterile isotonic aqueous buffer, and combinations thereof.

Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In embodiments, the pharmaceutical composition is provided in a solid form, such as a lyophilized powder suitable for reconstitution, a liquid solution, suspension, emulsion, tablet, pill, capsule, sustained release formulation, or powder.

In embodiments, the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container.

Methods for formulating the pharmaceutical compositions of the present invention are conventional and well-known in the art (see Remington and Remington's). One of skill in the art can readily formulate a pharmaceutical composition having the desired characteristics (e.g., route of administration, biosafety, and release profile).

Methods for preparing the pharmaceutical compositions include the step of bringing into association the active ingredient with a pharmaceutically acceptable carrier and, optionally, one or more accessory ingredients. The pharmaceutical compositions can be prepared by uniformly and intimately bringing into association the active ingredient with liquid carriers, or finely divided solid carriers, or both, and then, if necessary, shaping the product. Additional methodology for preparing the pharmaceutical compositions, including the preparation of multilayer dosage forms, are described in *Ansel's Pharmaceutical Dosage Forms and Drug Delivery Systems* (9th ed., Lippincott Williams & Wilkins), which is hereby incorporated by reference.

Methods of Delivery

The pharmaceutical compositions of the present invention can be administered to a subject by oral and non-oral means (e.g., topically, transdermally, or by injection). Such modes of administration and the methods for preparing an appropriate pharmaceutical composition for use therein are described in *Gibaldi's Drug Delivery Systems in Pharmaceutical Care* (1st ed., American Society of Health-System Pharmacists), which is hereby incorporated by reference.

In embodiments, the pharmaceutical compositions are administered orally in a solid form.

Pharmaceutical compositions suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) described herein, a derivative thereof, or a pharmaceutically acceptable salt or prodrug thereof as the active ingredient(s). The active ingredient can also be administered as a bolus, electuary, or paste.

In solid dosage forms for oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well-known in the art.

The pharmaceutical compositions can also be formulated so as to provide slow, extended, or controlled release of the active ingredient therein using, for example, hydroxypropylmethyl cellulose in varying proportions to provide the desired release profile, other polymer matrices, liposomes and/or microspheres. The pharmaceutical compositions can also optionally contain opacifying agents and may be of a composition that releases the active ingredient(s) only, or preferentially, in a certain portion of the gastrointestinal tract, optionally, in a delayed manner. Examples of embedding compositions include polymeric substances and waxes. The active ingredient can also be in micro-encapsulated form, if appropriate, with one or more pharmaceutically acceptable carriers, excipients, or diluents well-known in the art (see, e.g., Remington and Remington's).

The pharmaceutical compositions can be sterilized by, for example, filtration through a bacteria-retaining filter, or by incorporating sterilizing agents in the form of sterile solid compositions which can be dissolved in sterile water, or some other sterile injectable medium immediately before use.

In embodiments, the pharmaceutical compositions are administered orally in a liquid form.

Liquid dosage forms for oral administration of an active ingredient include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. In addition to inert diluents, the liquid pharmaceutical compositions can include adjuvants such as wetting agents; emulsifying and suspending agents, sweetening, flavoring, coloring, perfuming and preservative agents, and the like.

Suspensions, in addition to the active ingredient(s) can contain suspending agents such as, but not limited to, ethoxylated isostearyl alcohols, polyoxyethylene sorbitol and sorbitan esters, microcrystalline cellulose, aluminum metahydroxide, bentonite, agar-agar and tragacanth, and mixtures thereof.

In embodiments, the pharmaceutical compositions are administered by non-oral means such as by topical application, transdermal application, injection, and the like. In related embodiments, the pharmaceutical compositions are administered parenterally by injection, infusion, or implantation (e.g., intravenous, intramuscular, intraarticular, subcutaneous, and the like).

Compositions for parenteral use can be presented in unit dosage forms, e.g. in ampoules or in vials containing several doses, and in which a suitable preservative can be added. Such compositions can be in form of a solution, a suspension, an emulsion, an infusion device, a delivery device for implantation, or it can be presented as a dry powder to be reconstituted with water or another suitable vehicle before use. One or more co-vehicles, such as ethanol, can also be employed. Apart from the active ingredient(s), the compositions can contain suitable parenterally acceptable carriers and/or excipients or the active ingredient(s) can be incorporated into microspheres, microcapsules, nanoparticles, liposomes, or the like for controlled release. Furthermore, the compositions can also contain suspending, solubilising stabilising, pH-adjusting agents, and/or dispersing agents.

The pharmaceutical compositions can be in the form of sterile injections. To prepare such a composition, the active ingredient is dissolved or suspended in a parenterally acceptable liquid vehicle. Exemplary vehicles and solvents include, but are not limited to, water, water adjusted to a suitable by addition of an appropriate amount of hydrochloric acid, sodium hydroxide or a suitable buffer, 1,3-butanediol, Ringer's solution and isotonic sodium chloride solution. The pharmaceutical composition can also contain one or more preservatives, for example, methyl, ethyl or n-propyl p-hydroxybenzoate. To improve solubility, a dissolution enhancing or solubilising agent can be added or the solvent can contain 10-60% w/w of propylene glycol or the like.

The pharmaceutical compositions can contain one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

Examples of suitable aqueous and nonaqueous carriers, which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

In embodiments, the active ingredient(s) are administered by aerosol. This is accomplished by preparing an aqueous aerosol, liposomal preparation, or solid particles containing the compound. A nonaqueous (e.g., fluorocarbon propellant) suspension can be used. The pharmaceutical composition can also be administered using a sonic nebulizer, which would minimize exposing the agent to shear, which can result in degradation of the compound.

Ordinarily, an aqueous aerosol is made by formulating an aqueous solution or suspension of the active ingredient(s) together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Dosage forms for topical or transdermal administration of an active ingredient(s) includes powders, sprays, ointments, pastes, creams, lotions, gels, solutions, patches and inhalants. The active ingredient(s) can be mixed under sterile conditions with a pharmaceutically acceptable carrier, and with any preservatives, buffers, or propellants as appropriate.

Transdermal patches suitable for use in the present invention are disclosed in *Transdermal Drug Delivery: Developmental Issues and Research Initiatives* (Marcel Dekker Inc., 1989) and U.S. Pat. Nos. 4,743,249, 4,906,169, 5,198,223, 4,816,540, 5,422,119, 5,023,084, which are hereby incorporated by reference. The transdermal patch can also be any transdermal patch well-known in the art, including transscrotal patches. Pharmaceutical compositions in such transdermal patches can contain one or more absorption enhancers or skin permeation enhancers well-known in the art (see, e.g., U.S. Pat. Nos. 4,379,454 and 4,973,468, which are hereby incorporated by reference). Transdermal therapeutic systems for use in the present invention can be based on iontophoresis, diffusion, or a combination of these two effects.

Transdermal patches have the added advantage of providing controlled delivery of active ingredient(s) to the body. Such dosage forms can be made by dissolving or dispersing the active ingredient(s) in a proper medium. Absorption enhancers can also be used to increase the flux of the active ingredient across the skin. The rate of such flux can be controlled by either providing a rate controlling membrane or dispersing the active ingredient(s) in a polymer matrix or gel.

Such pharmaceutical compositions can be in the form of creams, ointments, lotions, liniments, gels, hydrogels, solutions, suspensions, sticks, sprays, pastes, plasters and other kinds of transdermal drug delivery systems. The compositions can also include pharmaceutically acceptable carriers or excipients such as emulsifying agents, antioxidants, buffering agents, preservatives, humectants, penetration enhancers, chelating agents, gel-forming agents, ointment bases, perfumes, and skin protective agents.

Examples of emulsifying agents include, but are not limited to, naturally occurring gums, e.g. gum acacia or gum tragacanth, naturally occurring phosphatides, e.g. soybean lecithin and sorbitan monooleate derivatives.

Examples of antioxidants include, but are not limited to, butylated hydroxy anisole (BHA), ascorbic acid and derivatives thereof, tocopherol and derivatives thereof, and cysteine.

Examples of preservatives include, but are not limited to, parabens, such as methyl or propyl p-hydroxybenzoate and benzalkonium chloride.

Examples of humectants include, but are not limited to, glycerin, propylene glycol, sorbitol and urea.

Examples of penetration enhancers include, but are not limited to, propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, Transcutol®, and Azone®.

Examples of chelating agents include, but are not limited to, sodium EDTA, citric acid and phosphoric acid.

Examples of gel forming agents include, but are not limited to, Carbopol, cellulose derivatives, bentonite, alginates, gelatin and polyvinylpyrrolidone.

In addition to the active ingredient(s), the ointments, pastes, creams, and gels of the present invention can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons, and volatile unsubstituted hydrocarbons, such as butane and propane.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Subcutaneous implants are well-known in the art and are suitable for use in the present invention. Subcutaneous implantation methods are preferably non-irritating and mechanically resilient. The implants can be of matrix type, of reservoir type, or hybrids thereof. In matrix type devices, the carrier material can be porous or non-porous, solid or semi-solid, and permeable or impermeable to the active compound or compounds. The carrier material can be biodegradable or may slowly erode after administration. In some instances, the matrix is non-degradable but instead relies on the diffusion of the active compound through the matrix for the carrier material to degrade. Alternative subcutaneous implant methods utilize reservoir devices where the active compound or compounds are surrounded by a rate controlling membrane, e.g., a membrane independent of component concentration (possessing zero-order kinetics). Devices consisting of a matrix surrounded by a rate controlling membrane also suitable for use.

Both reservoir and matrix type devices can contain materials such as polydimethylsiloxane, such as Silastic™, or other silicone rubbers. Matrix materials can be insoluble polypropylene, polyethylene, polyvinyl chloride, ethylvinyl acetate, polystyrene and polymethacrylate, well as glycerol esters of the glycerol palmitostearate, glycerol stearate, and glycerol behenate type. Materials can be hydrophobic or hydrophilic polymers and optionally contain solubilising agents.

Subcutaneous implant devices can be slow-release capsules made with any suitable polymer, e.g., as described in U.S. Pat. Nos. 5,035,891 and 4,210,644, which are hereby incorporated by reference.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition can be obtained by using a suitable mixture of these approaches.

In a membrane-moderated system, the active ingredient is present in a reservoir which is totally encapsulated in a shallow compartment molded from a drug-impermeable laminate, such as a metallic plastic laminate, and a rate-controlling polymeric membrane such as a microporous or a nonporous polymeric membrane, e.g., ethylene-vinyl acetate copolymer. The active ingredient is released through the ratecontrolling polymeric membrane. In the drug reservoir, the active ingredient can either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active ingredient is formed by directly dispersing the active ingredient in an adhesive polymer and then by, e.g., solvent casting, spreading the adhesive containing the active ingredient ance onto a flat sheet of substantially drug-impermeable metallic plastic backing to form a thin drug reservoir layer.

A matrix dispersion-type system is characterized in that a reservoir of the active ingredient is formed by substantially homogeneously dispersing the active ingredient in a hydrophilic or lipophilic polymer matrix. The drug-containing polymer is then molded into disc with a substantially well-defined surface area and controlled thickness. The adhesive polymer is spread along the circumference to form a strip of adhesive around the disc.

A microreservoir system can be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Any of the above-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

Methods of Delivery

When the compound(s) of the invention are administered as pharmaceuticals to humans and animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, compounds or pharmaceutical compositions of the invention are administered in an effective amount or quantity sufficient to reduce or inhibit spermatozoa emission in a male subject. In embodiments, administration of the compound or pharmaceutical composition suppresses spermatogenesis, induces azoospermia, or induces oligozoospermia.

Exemplary dose ranges include 0.01 mg to 250 mg per day, 0.01 mg to 100 mg per day, 1 mg to 100 mg per day, 10 mg to 100 mg per day, 1 mg to 10 mg per day, and 0.01 mg to 10 mg per day. A preferred dose of the compound of the invention is the maximum that a patient can tolerate and not develop serious or unacceptable side effects. In embodiments, the compound(s) of the present invention is administered at a concentration of about 10 micrograms to about 100 mg per kilogram of body weight per day, about 0.1 to about 10 mg/kg per day, or about 1.0 mg to about 10 mg/kg of body weight per day.

In embodiments, the pharmaceutical composition comprises a compound(s) of the invention in an amount ranging between 1 and 10 mg, such as 1, 2, 3, 4, 5, 6, 7, 8, 9, or 10 mg.

In embodiments, the therapeutically effective dosage produces a serum concentration of compound of from about 0.1 ng/ml to about 50-100 µg/ml. The pharmaceutical compositions typically should provide a dosage of from about 0.001 mg to about 2000 mg of compound per kilogram of body weight per day. For example, dosages for systemic administration to a human patient can range from 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

In embodiments, the pharmaceutical composition comprises a compound(s) of the invention in an amount sufficient to lower spermatozoa concentration to not more than 3 million/mL of semen, such as not more than 2 million/mL, 1 million/mL, 0.5 million/mL, 0.25 million/mL, or 0.1 million/mL. In related embodiments, the pharmaceutical composition comprises a compound(s) of the invention in an amount sufficient to lower spermatozoa concentration to not more than 0.1 million/mL.

Determination of an effective amount is well within the capability of those skilled in the art, especially in light of the detailed disclosure provided herein. Generally, an efficacious or effective amount of a compound(s) of the invention is determined by first administering a low dose of the compound(s) and then incrementally increasing the administered dose or dosages until a desired effect (e.g., decreased spermatozoa levels in seminal fluid) is observed in the treated subject, with minimal or acceptable toxic side effects. Applicable methods for determining an appropriate dose and dosing schedule for administration of a pharmaceutical composition of the present invention are described, for example, in *Goodman and Gilman's The Pharmacological Basis of Therapeutics*, Goodman et al., eds., 11th Edition, McGraw-Hill 2005, and *Remington: The Science and Practice of Pharmacy*, 20th and 21st Editions, Gennaro and University of the Sciences in Philadelphia, Eds., Lippencott & Wilkins (2003 and 2005), which are hereby incorporated by reference.

Kits

The invention provides for a kit for effecting male contraception. In embodiments, the kit contains one or more of the compounds or pharmaceutical compositions described herein. In embodiments, the kit provides instructions for use. The instructions for use can pertain to any of the methods described herein. In related embodiments, the instructions pertain to using the compound(s) or pharmaceutical composition(s) for reducing or inhibiting spermatozoa emission. In embodiments, the kit provides a notice in the form prescribed by a governmental agency regulating the manufacture, use, or sale of pharmaceuticals or biological products, which notice reflects approval by the agency of manufacture, use or sale of the kit and the components therein for human administration.

The invention also provides for compound(s) or pharmaceutical composition(s) packaged in a hermetically sealed container (e.g., ampoule or sachette) indicating the quantity of compound. In embodiments, a compound or pharmaceutical composition is supplied as a liquid. In other embodiments, a compound or pharmaceutical composition is supplied as a dry sterilized lyophilized powder or water free concentrate in a hermetically sealed container and can be reconstituted, e.g., with water or saline, to the appropriate concentration for administration to a subject.

The invention also provides for transdermal patches containing the compound(s) or pharmaceutical composition(s).

In embodiments, the kit provides compound(s) or pharmaceutical composition(s) in more than one dosage unit. The kit can contain from 1 to about 120 or more, from 1 to about 60, from 1 to about 30, from 1 to about 10, or from 1 to about 7 dosage units. In cases where the compound(s) or pharmaceutical composition(s) is adapted to release a therapeutically effective amount of the active ingredient over a 24 hour period, the kit conveniently comprises 1, about 5, about 7, about 10, about 14, or about 30 dosage units. In cases where the compound(s) or pharmaceutical composition(s) is adapted to provide a therapeutically effective amount of the active ingredient over a 12 hour period, the kit conveniently comprises 1, 2, about 10, about 14, about 30 or about 60 dosage units. In cases where the compound(s) or pharmaceutical composition(s) is adapted to provide a therapeutically effective amount of the active ingredient over an about 3 to about 10 hour (e.g., about a 6 or 8 hour) period, the kit comprises about 1, about 4, about 40, about 60 or about 120 dosage units. One skilled in the art will recognize that other numbers of dosage units can be included in the kit without departing materially from the present invention.

Screening Methods

As described herein, the invention provides specific examples of chemical compounds, including JQ1, as well as other substituted compounds that bind a bromodomain binding pocket and are useful as a male contraceptive. However, the invention is not so limited. The invention further provides a simple means for identifying agents (including nucleic acids, peptides, small molecule inhibitors, and mimetics) that are capable of inhibiting spermatogenesis. Such compounds are also expected to be useful as male contraceptives.

In particular embodiments, the effect of a compound or other agent of the invention is analyzed by assaying spermatogenesis. Agents and compounds of the invention that reduce spermatogenesis are identified as useful as male contraceptives.

Virtually any agent that specifically binds to a BET family member or that reduces the biological activity of a BET family member may be employed in the methods of the invention. Methods of the invention are useful for the high-throughput low-cost screening of candidate agents that reduce or otherwise inhibit spermatogenesis. A candidate agent that specifically binds to a bromodomain of a BET family member is then isolated and tested for activity in an in vitro assay or in vivo assay for its ability to inhibit spermatogenesis. One skilled in the art appreciates that the effects of a candidate agent on a cell is typically compared to a corresponding control cell not contacted with the candidate agent. Thus, the screening methods include comparing spermatogenesis in a testes contacted by a candidate agent to the spermatogenesis present in an untreated control testes.

Once identified, agents of the invention (e.g., agents that specifically bind to and/or antagonize a bromodomain) may be used as male contraceptives. Potential bromodomain antagonists include organic molecules, peptides, peptide mimetics, polypeptides, nucleic acid ligands, aptamers, and antibodies that bind to a BET family member bromodomain and reduce its activity. Candidate agents may be tested for their ability to reduce spermatogenesis.

Test Compounds and Extracts

In certain embodiments, BET family member antagonists (e.g., agents that specifically bind and reduce the activity of a bromodomain) are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223, 409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have BET family member bromodomain binding activity further fractionation of the positive lead extract is necessary to isolate molecular constituents responsible for the observed effect. Thus, the goal of the extraction, fractionation, and purification process is the careful characterization and identification of a chemical entity within the crude extract that reduces spermatogenesis. Methods of fractionation and purification of such heterogenous extracts are known in the art. If desired, compounds shown to be useful as therapeutics are chemically modified according to methods known in the art.

EXAMPLES

It should be appreciated that the invention should not be construed to be limited to the examples that are now described; rather, the invention should be construed to include any and all applications provided herein and all equivalent variations within the skill of the ordinary artisan.

I. Chemical Examples

Synthesis and Methods of Preparation

Compounds of the invention can be synthesized by methods described herein, and/or according to methods known to one of ordinary skill in the art in view of the description herein.

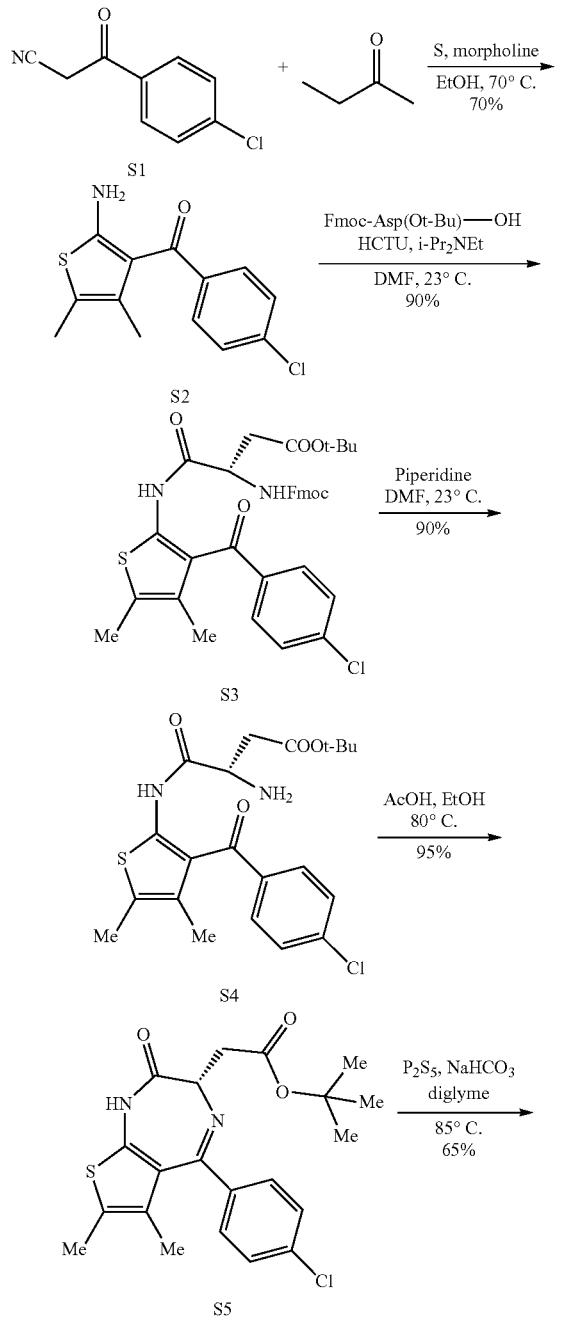

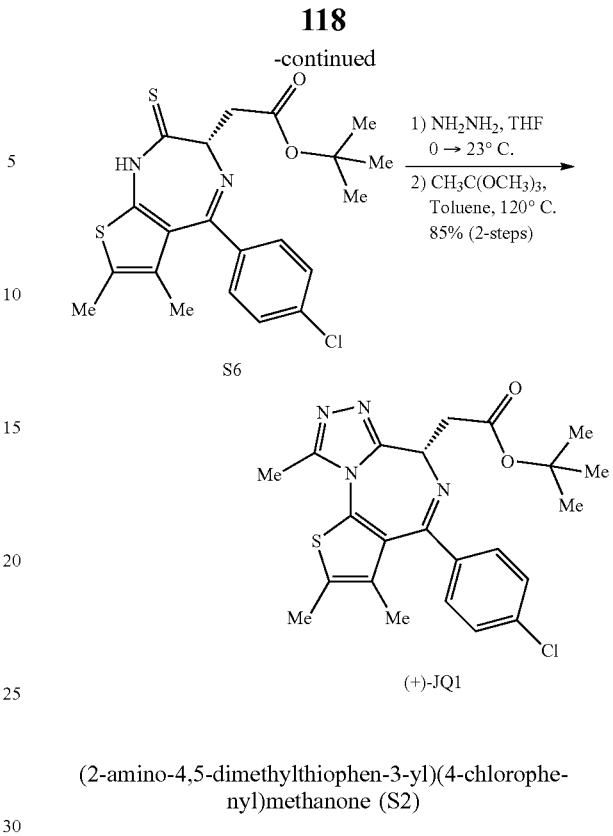

(2-amino-4,5-dimethylthiophen-3-yl)(4-chlorophenyl)methanone (S2)

The compound JQ1 was prepared according to the scheme shown above.

Sulfur (220 mg, 6.9 mmol, 1.00 equiv) was added as a solid to a solution of 4-chlorobenzoyl acetonitrile S1 (1.24 g, 6.9 mmol, 1 equiv), 2-butanone (0.62 ml, 6.9 mmol, 1.00 equiv), and morpholine (0.60 ml, 6.9 mmol, 1.00 equiv) in ethanol (20 ml, 0.35 M) at 23° C.[21]. The mixture was then heated to 70° C. After 12 hours, the reaction mixture was cooled to 23° C. and poured into brine (100 ml). The aqueous layer was extracted with ethyl acetate (3×50 ml). The combined organic layers were washed with brine (50 ml), were dried over anhydrous sodium sulphate, were filtered, and were concentrated under reduced pressure. The residue was purified by flash column chromatography (Combiflash RF system, 40 gram silica gel, gradient 0 to 100% ethyl acetate-hexanes) to afford S2 (1.28 g, 70%) as a yellow solid.

(S)-tert-Butyl-3-({[(9H-fluoren-9-yl)methoxy]carbonyl}amino)-4-{[3-(4-chorobenzoyl)-4,5-dimethylthiophen-2-yl]amino}-4-oxobutanoate (S3)

(2-(6-Chloro-1H-benzotriazole-1-yl)-1,1,3,3-tetramethylaminium hexafluorophosphate (HCTU) (827 mg, 2.0 mmol, 2.00 equiv), and N,N-diisopropylethylamine (0.72 ml, 4.0 mmol, 4.00 equiv) were added sequentially to a solution of 9-fluorenylmethoxycarbonyl-aspartic acid β-tert-butyl ester [Fmoc-Asp(Ot-Bu)-OH] (864 mg, 2.1 mmol, 2.10 equiv) in N,N-dimethylformamide (1.5 ml, 1.0 M). The mixture was then stirred at 23° C. for 5 min. S2 (266 mg, 1.0 mmol, 1 equiv) was then added as a solid. The reaction mixture was stirred at 23° C. After 16 hours, ethyl acetate (20 ml) and brine (20 ml) were added. The two layers were separated, and the aqueous layer was extracted with ethyl acetate (2×20 ml). The combined organic layers were washed with brine (30 ml), were dried over with anhydrous sodium sulphate, were filtered, and were concentrated under reduced pressure.

The residue was purified by flash column chromatography (Combiflash RF, 40 gram silica gel, gradient 0 to 100% ethyl acetate-hexanes) to afford S3 (625 mg, 90%) as brown oil.

(S)-tert-butyl 3-amino-4-((3-(4-chlorobenzoyl)-4,5-dimethylthiophen-2-yl)amino)-4-oxobutanoate (S4)

Compound S3 (560 mg, 0.85 mmol, 1 equiv) was dissolved into 20% piperidine in DMF solution (4.0 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexanes) to afford free amine S4 (370 mg, 90%) as yellow solid. The enantiomeric purity dropped to 75% (determined with Berger Supercritical Fluid Chromatography (SFC) using AS-H column).

(S)-tert-Butyl 2-(5-(4-chlorophenyl)-6,7-dimethyl-2-oxo-2,3-dihydro-1H-thieno[2,3-e][1,4]diazepin-3-yl)acetate (S5)

Amino ketone (S4) (280 mg, 0.63 mmol) was dissolved in 10% acetic acid ethanol solution (21 ml, 0.03 M). The reaction mixture was heated to 85° C. After 30 minutes, all solvents were removed under reduced pressure. The residue was purified by flash column chromatography (Combiflash RF system, 12 gram silica gel, gradient 0 to 100% ethyl acetate-hexanes) to afford compound S5 (241 mg, 95%) as white solid. Enantiomeric purity of S5 was 67% (determined with Berger Supercritical Fluid Chromatography (SFC) using an AS-H column).

tert-Butyl 2-(5-(4-chlorophenyl)-6,7-dimethyl-2-thioxo-2,3-dihydro-1H-thieno[2,3-e][1,4]diazepin-3-yl)acetate (S6)

Phosphorus pentasulfide (222 mg, 1.0 mmol, 2.00 equiv), sodium bicarbonate (168 mg, 2.0 mmol, 4.00 equiv) were added sequentially to a solution of S5 (210 mg, 0.5 mmol, 1 equiv) diglyme (1.25 ml, 0.4M). The reaction mixture was heated to 90° C. After 16 h, brine (20 ml) and ethyl acetate (35 ml) were added. The two layers were separated, and the aqueous layer was extracted with ethyl acetate (3×30 ml). The combined organic layers were washed with brine (2×15 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexanes) to afford S6 (141 mg, 65%) as brown solid with recovered S5 (73 mg, 34%).

tert-Butyl 2-(4-(4-chlorophenyl)-2,3,9-trimethyl-6H-thieno[3,2-f][1,2,4]triazolo[4,3-a][1,4]diazepin-6-yl)acetate [(±)JQ1]

Hydrazine (0.015 ml, 0.45 mmol, 1.25 equiv) was added to a solution of S6 (158 mg, 0.36 mmol, 1 equiv) in THF (2.6 ml, 0.14 M) at 0° C. The reaction mixture was warmed to 23° C., and stirred at 23° C. for 1 h. All solvents were removed under reduced pressure. The resulting hydrazine was used directly without purification. The hydrazine was then dissolved in a 2:3 mixture of trimethyl orthoacetate and toluene (6 ml, 0.06 M). The reaction mixture was heated to 120° C. After 2 h, all the solvents were removed under reduced pressure. The residue was purified by flash column chromatography (Combiflash system, 4 g silica gel, gradient 0 to 100% ethyl acetate-hexanes) to afford JQ1 (140 mg, 85% in 2 steps) as white solid. The reaction conditions further epimerized the stereogenic center, resulting in the racemate, JQ1 (determined with Berger Supercritical Fluid Chromatography (SFC) with an AS-H column).

Scheme S2. Synthesis of enantiomerically enriched (+)-JQ1.

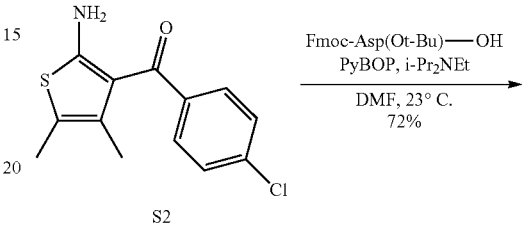

S2

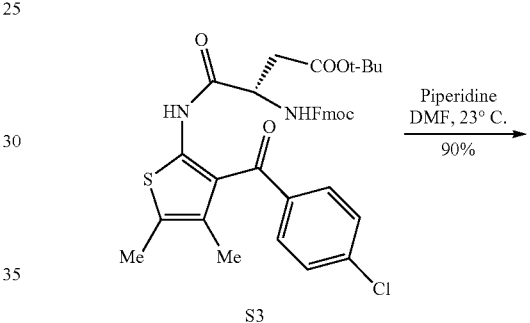

S3

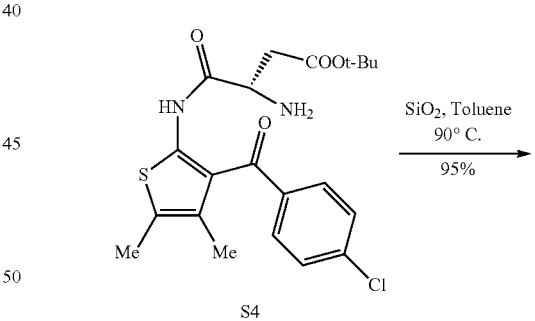

S4

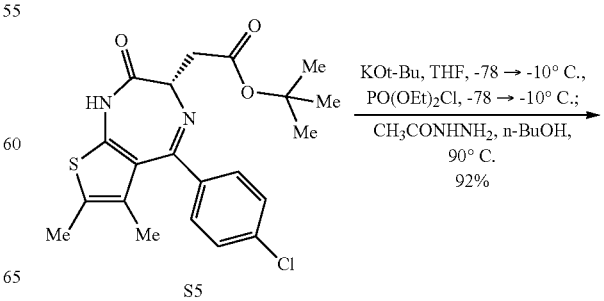

S5

-continued

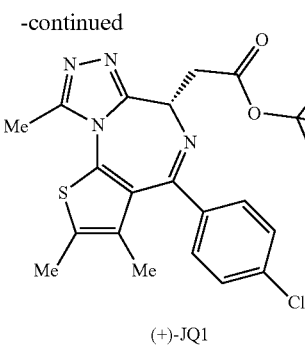

(+)-JQ1

(S)-tert-Butyl-3-({[(9H-fluoren-9-yl)methoxy]carbonyl}amino)-4-{[3-(4-chlorobenzoyl)-4,5-dimethylthiophen-2-yl]amino}-4-oxobutanoate (S3)

(Benzotriazol-1-yloxyl)tripyrrolidinophosphonium (PyBOP) (494 mg, 0.95 mmol, 0.95 equiv), N,N-diisopropylethylamine (0.50 ml, 2.8 mmol, 2.75 equiv) were added sequentially to a solution of 9-fluorenylmethoxycarbonyl-aspartic acid p-tert-butyl ester [Fmoc-Asp(Ot-Bu)-OH] (411 mg, 1.00 mmol, 1.0 equiv) in N,N-dimethylformamide (1.0 ml, 1.0 M). The mixture was then stirred at 23° C. for 5 min. S2 (266 mg, 1.0 mmol, 1 equiv) was then added as solid. The reaction mixture was stirred at 23° C. After 4 h, ethyl acetate (20 ml) and brine (20 ml) were added. The two layers were separated, and the aqueous layer was extracted with ethyl acetate (2×20 ml). The combined organic layers were washed with brine, were dried over with anhydrous sodium sulphate, were filtered, and were concentrated under reduced pressure. The residue was purified by flash column chromatography (Combiflash RF system, 40 gram silica gel, gradient 0 to 100% ethyl acetate-hexanes) to afford S3 (152 mg, 72%) as brown oil.

(S)-tert-butyl 3-amino-4-((3-(4-chlorobenzoyl)-4,5-dimethylthiophen-2-yl)amino)-4-oxobutanoate (S4)

Compound S3 (310 mg, 0.47 mmol, 1 equiv) was dissolved into 20% piperidine in DMF solution (2.2 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexane) to afford free amine S4 (184 mg, 90%) as yellow solid. The enantiomeric purity was 91% (checked with Berger Supercritical Fluid Chromatography (SFC) using an AS-H column).

(S)-tert-Butyl 2-(5-(4-chlorophenyl)-6,7-dimethyl-2-oxo-2,3-dihydro-1H-thieno[2,3-e][1,4]diazepin-3-yl)acetate (S5)

Amino ketone (S4) (184 mg, 0.42 mmol) was dissolved in toluene (10 ml, 0.04 M). Silica gel (300 mg) was added, and the reaction mixture was heated to 90° C. After 3 h, the reaction mixture was cooled to 23° C. The silica gel was filtered, and washed with ethyl acetate. The combined filtrates were concentrated. The residue was purified by flash column chromatography (Combiflash RF system, 12 gram silica gel, gradient 0 to 100% ethyl acetate-hexanes) to afford compound S5 (168 mg, 95%) as white solid. Enantiomeric purity of S5 was 90% (determined with Berger Supercritical Fluid Chromatography (SFC) using an AS-H column).

(S)-tert-Butyl 2-(4-(4-chlorophenyl)-2,3,9-trimethyl-6H-thieno[3,2-f][1,2,4]triazolo[4,3-a][1,4]diazepin-6-yl)acetate [(+)JQ1]

Potassium tert-butoxide (1.0 M solution in THF, 0.3 ml, 0.30 mmol, 1.10 equiv) was added to a solution of S5 (114 mg, 0.27 mmol, 1 equiv) in THF (1.8 ml, 0.15 M) at −78° C. The reaction mixture was warmed to −10° C., and stirred at 23° C. for 30 min. The reaction mixture was cooled to −78° C. Diethyl chlorophosphate (0.047 ml, 0.32 mmol, 1.20 equiv) was added to reaction mixture[22]. The resulting mixture was warmed to −10° C. over 45 min. Acetic hydrazide (30 mg, 0.40 mmol, 1.50 equiv) was added to reaction mixture. The reaction mixture was stirred at 23° C. After 1 h, 1-butanol (2.25 ml) was added to reaction mixture, which was heated to 90° C. After 1 h, all solvents were removed under reduce pressure. The residue was purified with flash column chromatography (Combiflash system, 4 g silica gel, gradient 0 to 100% ethyl acetate-hexanes) to afford (+)-JQ1 (114 mg, 92%) as white solid with 90% enantiomeric purity (determined with Berger Supercritical Fluid Chromatography (SFC) using AS-H column, 85% hexanes-methanol, 210 nm, $t_R$ (R-enantiomer)=1.59 min, $t_R$ (S-enantiomer)=3.67 min). The product was further purified by chiral preparative HPLC (Agilent High Pressure Liquid Chromatography using an OD-H column) to provide the S-enantiomer in greater than 99% ee.

$^1$H NMR (600 MHz, CDCl$_3$, 25° C.) δ 7.39 (d, J=8.4 Hz, 2H), 7.31 (d, J=8.4 Hz, 2H), 4.54 (t, J=6.6 MHz, 1H), 3.54-3.52 (m, 2H), 2.66 (s, 3H), 2.39 (s, 3H), 1.67 (s, 3H), 1.48 (s, 9H).

$^{13}$C NMR (150 MHz, CDCl$_3$, 25° C.) δ 171.0, 163.8, 155.7, 150.0, 136.9, 131.1, 130.9, 130.6, 130.3, 128.9, 81.2, 54.1, 38.1, 28.4, 14.6, 13.5, 12.1.

HRMS(ESI) calc'd for $C_{21}H_{24}ClN_2O_3S$ [M+H]$^+$: 457.1460, found 457.1451 m/z.

TLC (EtOAc), Rf: 0.32 (UV)

$[α]^{22}_D$=+75 (c 0.5, CHCl$_3$)

(−)-JQ1 was synthesized in a similar manner, employing Fmoc-D-Asp(Ot-Bu)-OH as a starting material, and was further purified by chiral preparative HPLC (Agilent High Pressure Liquid Chromatography using an OD-H column) to afford the R-enantiomer in greater than 99% ee. $[α]^{22}_D$=−72 (c 0.5, CHCl$_3$)

Synthesis of Additional Compounds

Additional compounds of the invention were prepared as illustrated in Scheme S3.

Scheme 3. Synthesis of hydrazine derivatives.

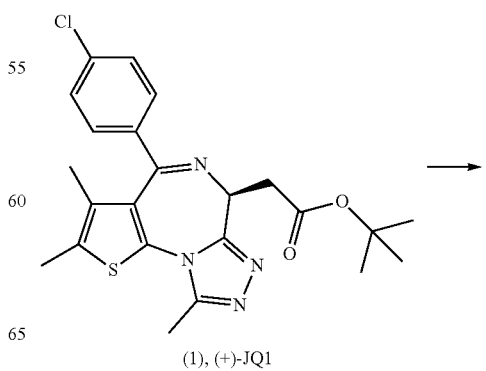

(1), (+)-JQ1

123
-continued

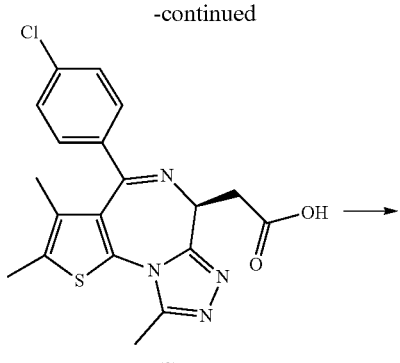
(2)

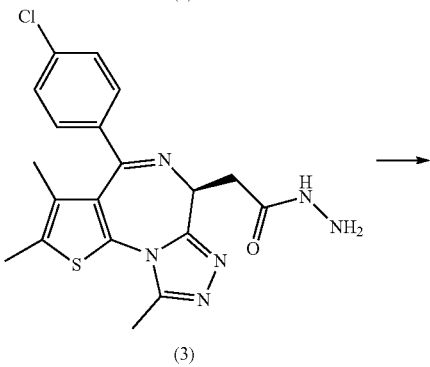
(3)

124
-continued

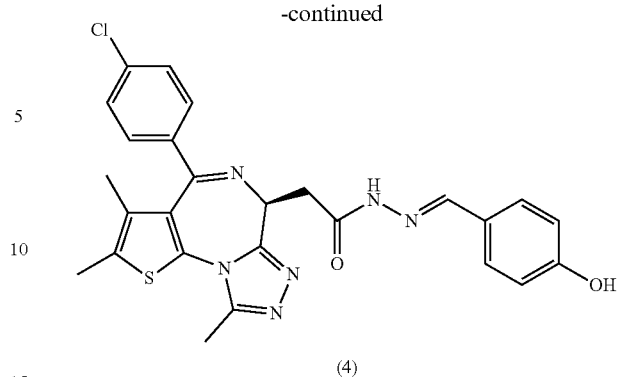
(4)

As shown in Scheme S3, the t-butyl ester of (+)-JQ1 (1) was cleaved to yield the free acid (2), which was coupled with hydrazine to yield the hydrazide (3). Reaction with 4-hydroxybenzaldehyde yielded the hydrazone (4).

Both hydrazide (3) and hydrazone (4) showed activity in at least one biological assay.

A library of compounds was prepared by reaction of the hydrazide (3) with a variety of carbonyl-containing compounds (see Table A, above).

Additional compounds were prepared for use, e.g., as probes for assay development. An exemplary synthesis is shown in Scheme S4, below.

Scheme S4. Synthesis of derivatives useful as probes.

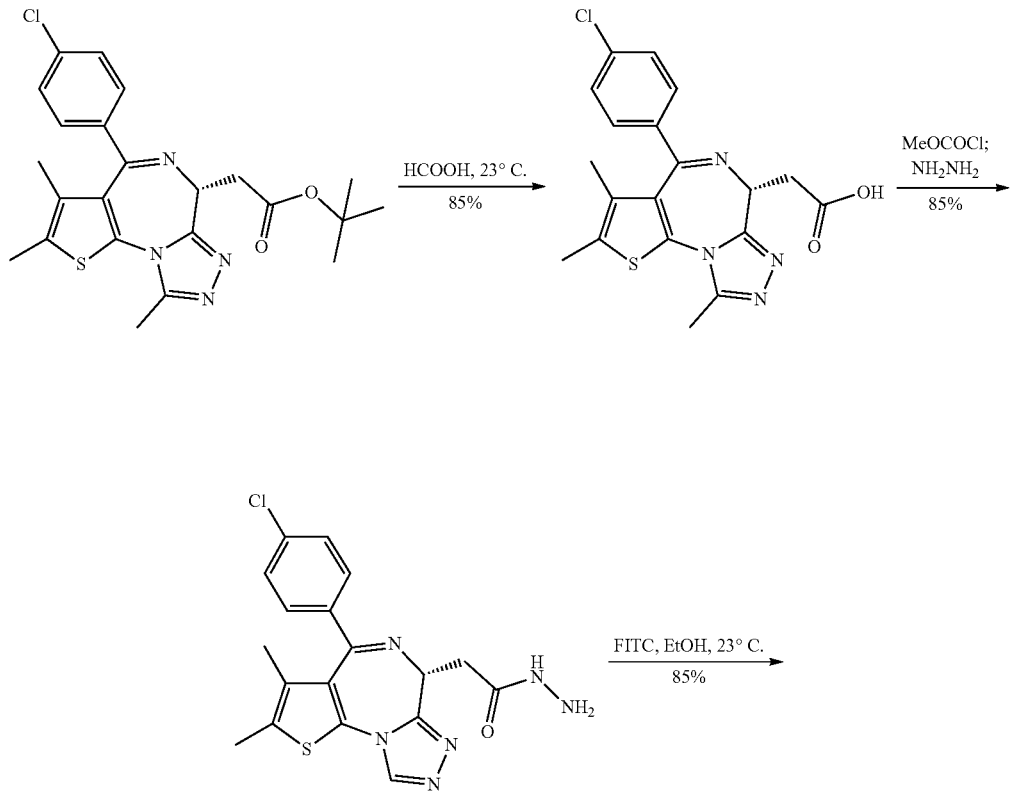

-continued
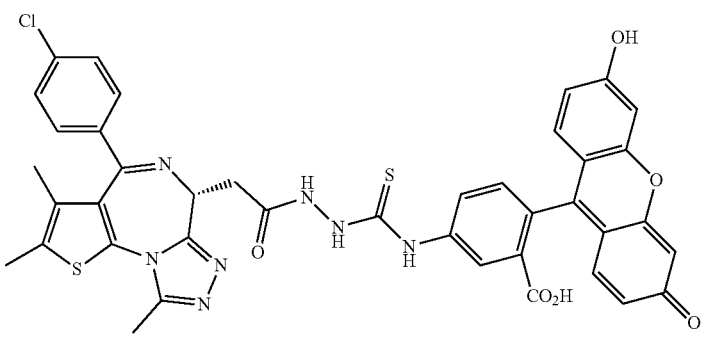
For FITC assay
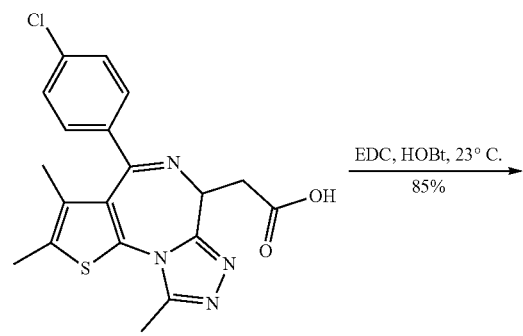
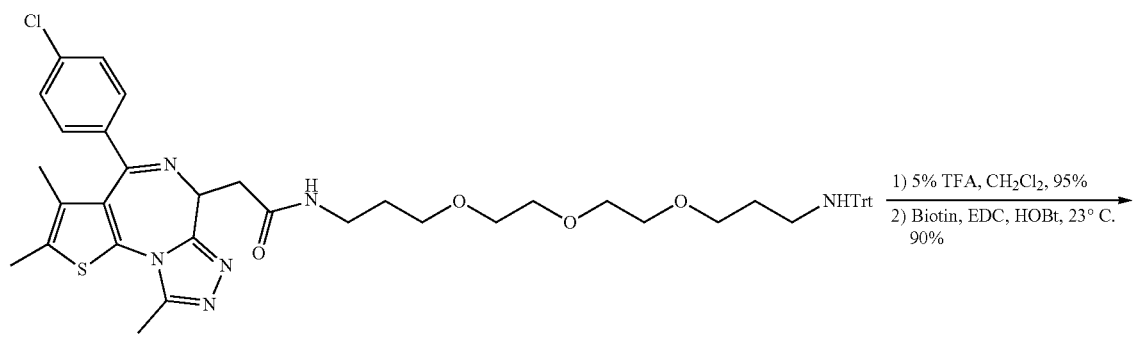
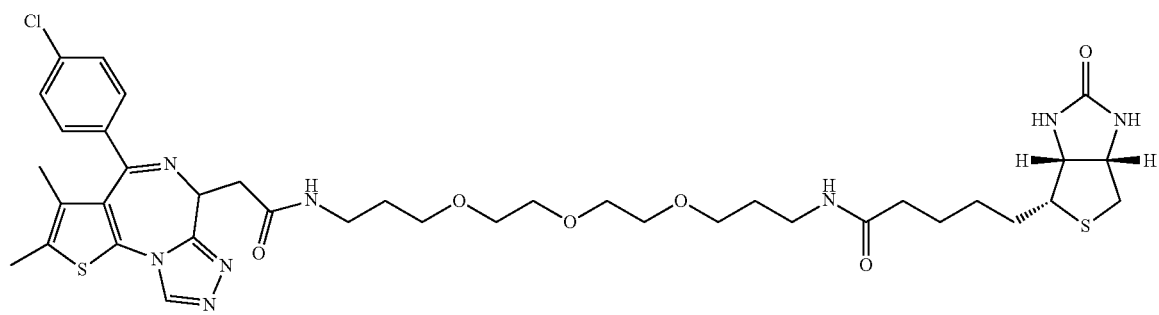
For Alpha assay Additional compounds were prepared as shown in the table below:

| Compound Name | Structure | MS [M + H]+ m/z (Observed) |
|---|---|---|
| (S)-JQ1 | 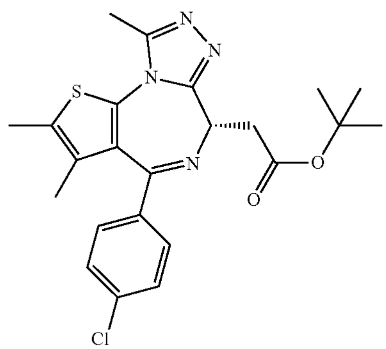 [SMILES: Cc1sc2c(c1C)C(c1ccc(Cl)cc1)=N[C@@H](CC(=O)OC(C)(C)C)c1nnc(C)n1-2] | 457.1 |
| (R)-JQ1 | 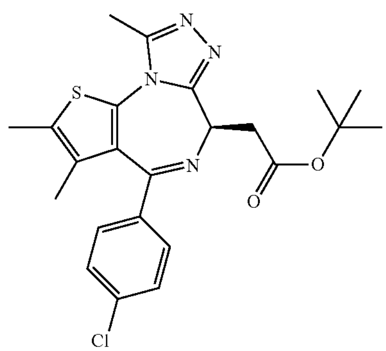 [SMILES: Cc1sc2c(c1C)C(c1ccc(Cl)cc1)=N[C@H](CC(=O)OC(C)(C)C)c1nnc(C)n1-2] | 457.1 |
| JQ3 | 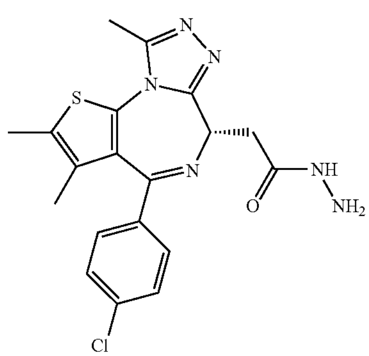 [SMILES: Cc1sc2c(c1C)C(c1ccc(Cl)cc1)=N[C@@H](CC(=O)NN)c1nnc(C)n1-2] | 415.1 |
| JQ4 | 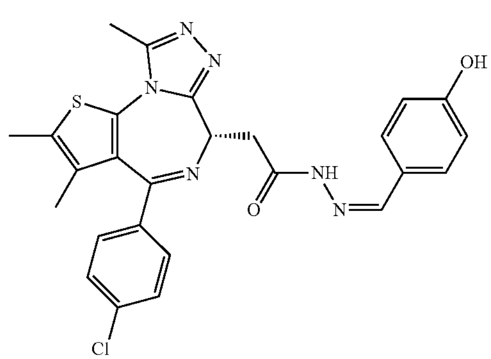 [SMILES: Cc1sc2c(c1C)C(c1ccc(Cl)cc1)=N[C@@H](CC(=O)N/N=C\c1ccc(O)cc1)c1nnc(C)n1-2] | 519.1 |

-continued
| Compound Name | Structure | MS [M + H]+ m/z (Observed) |
|---|---|---|
| JQ6 | 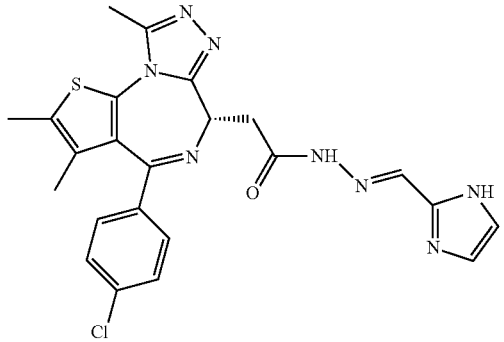 [SMILES: Cc1sc2c(c1C)C(c1ccc(Cl)cc1)=N[C@@H](CC(=O)N/N=C/c1ncc[nH]1)c1nnc(C)n1-2] | 493.1 |
| JQ7 | 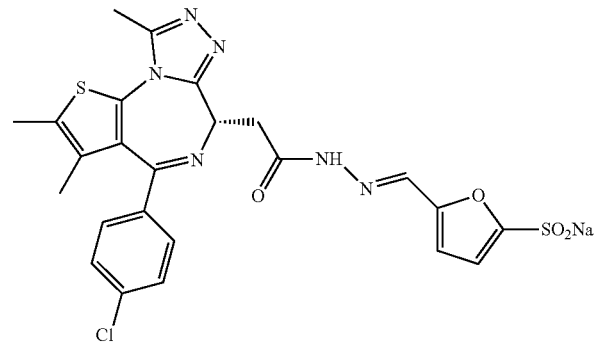 | 579.0 |
| JQ8 | 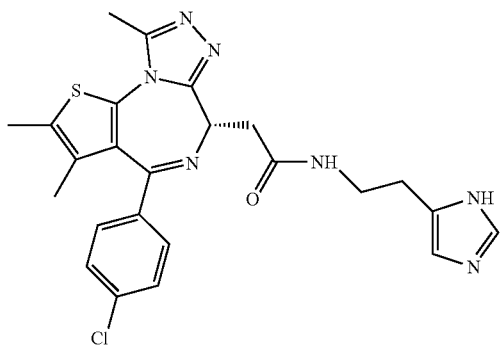 [SMILES: Cc1sc2c(c1C)C(c1ccc(Cl)cc1)=N[C@@H](CC(=O)NCCc1cnc[nH]1)c1nnc(C)n1-2] | 494.1 |
| JQ10 | 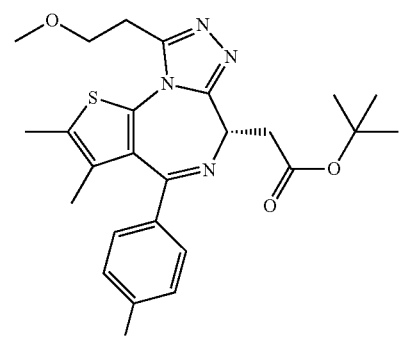 | 501.1 |

-continued
| Compound Name | Structure | MS [M + H]+ m/z (Observed) |
|---|---|---|
| JQ11 | 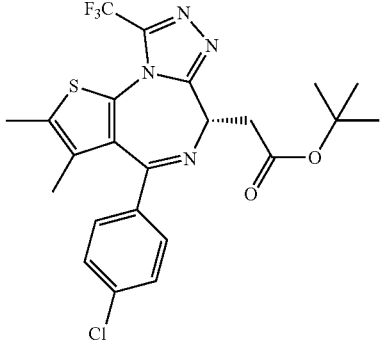 [SMILES: Cc1sc2c(c1C)C(c1ccc(Cl)cc1)=N[C@@H](CC(=O)OC(C)(C)C)c1nnc(C(F)(F)F)n1-2] | 511.1 |
| JQ1-FITC | 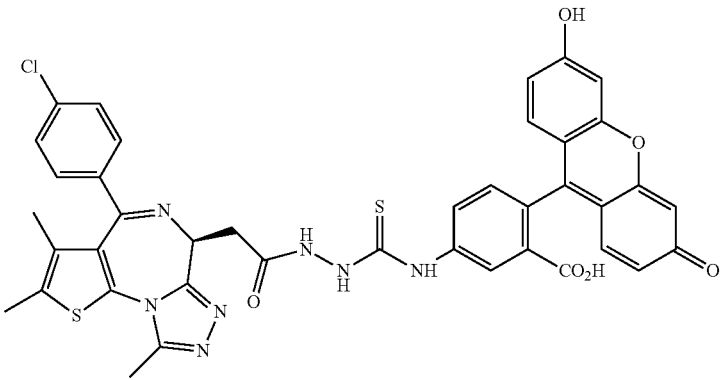 [SMILES: Cc1sc2c(c1C)C(c1ccc(Cl)cc1)=N[C@@H](CC(=O)NNC(=S)Nc1ccc(-c3c4ccc(=O)cc-4oc4cc(O)ccc34)c(C(=O)O)c1)c1nnc(C)n1-2] | 804.1 |
| JQ1-Biotin | 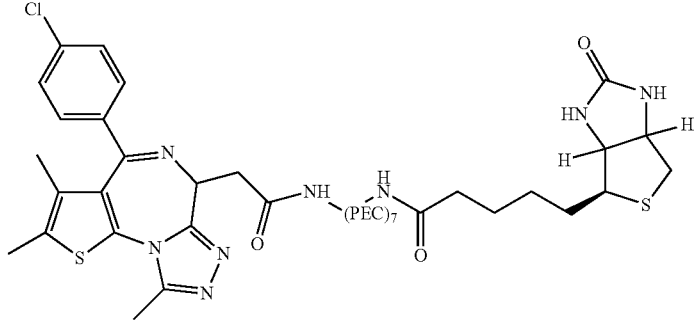 | 829.3 |
| JQ13 | 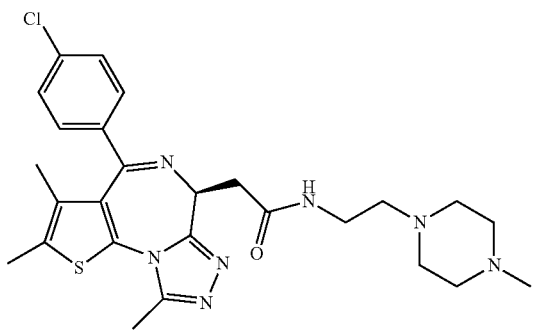 | 526.2 |

| Compound Name | Structure | MS [M + H]+ m/z (Observed) |
|---|---|---|
| KS1 | 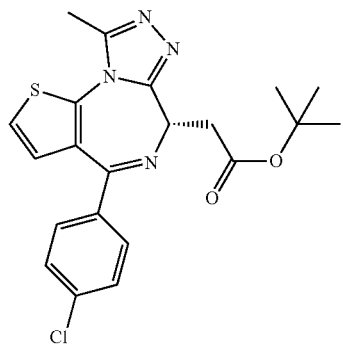 [SMILES: Cc1nnc2n1-c1sccc1C(c1ccc(Cl)cc1)=N[C@H]2CC(=O)OC(C)(C)C] | 429.1 |
| JQ18 | 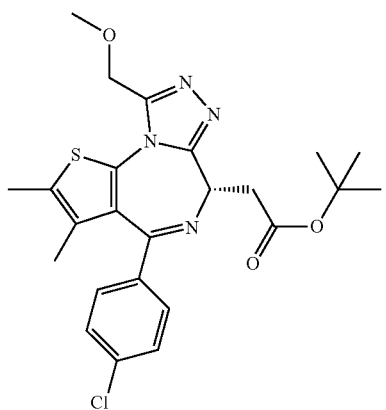  Chemical Formula: $C_{24}H_{27}ClN_4O_3S$  Exact Mass: 486.14924  Molecular Weight: 487.01418 | 487.1 |
| JQ19 | 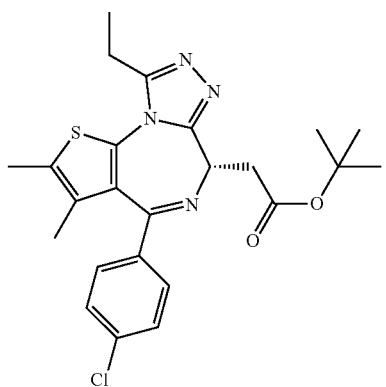  Chemical Formula: $C_{24}H_{27}ClN_4O_2S$  Exact Mass: 470.15432  Molecular Weight: 471.01478 | 471.1 |

| Compound Name | Structure | MS [M + H]+ m/z (Observed) |
|---|---|---|
| JQ20 | 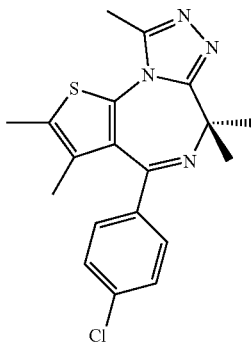<br>Chemical formula: C$_{19}$H$_{19}$ClN$_4$S<br>Exact Mass: 370.10190<br>Molecular Weight: 370.89896<br>JQI-iI-023 | 370.1 |
| JQ21 | 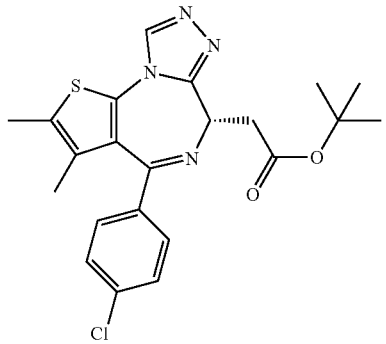<br>JQI-II-024<br>Chemical Formula: C$_{22}$H$_{23}$ClN$_4$O$_2$S<br>Exact Mass: 442.12303<br>Molecular Weight: 442.96162 | 443.1 |
| JQ24A | 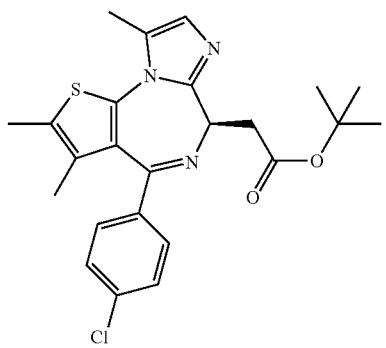<br>Chemical Formula: C$_{24}$H$_{26}$ClN$_3$O$_2$S<br>Exact Mass: 455.1434<br>Molecular Weight: 458.001 | 456.1 |

| Compound Name | Structure | MS [M + H]+ m/z (Observed) |
|---|---|---|
| JQ24B | 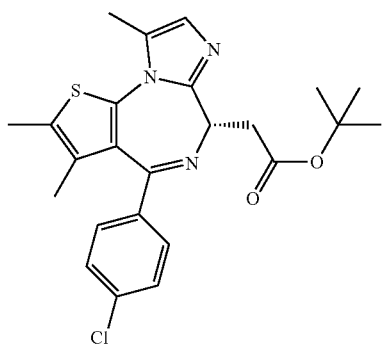<br>Chemical Formula: C_24H_26ClN_3O_2S<br>Exact Mass: 455.1434<br>Molecular Weight: 458.001 | 456.1 |
| JQ25 | 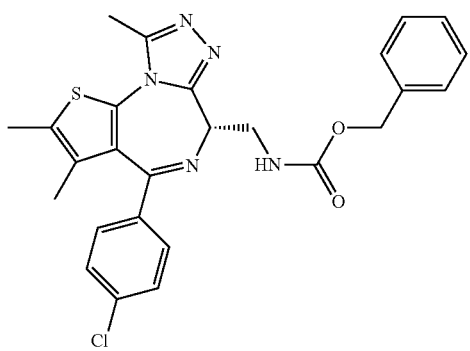<br>Chemical Formula: C_26H_24ClN_5O_2S<br>Exact Mass: 505.1339<br>Molecular Weight: 506.0191 | 506.1 |
| JQB | 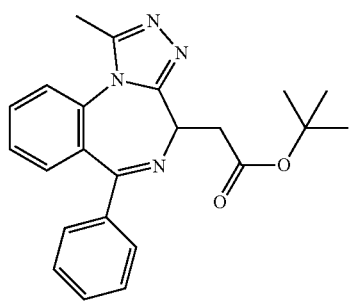<br>Chemical Formula: C_23H_24N_4O_2<br>Exact Mass: 388.1899<br>Molecular Weight: 388.4623 | 389.2 |

| Compound Name | Structure | MS [M + H]+ m/z (Observed) |
|---|---|---|
| JQ30 | 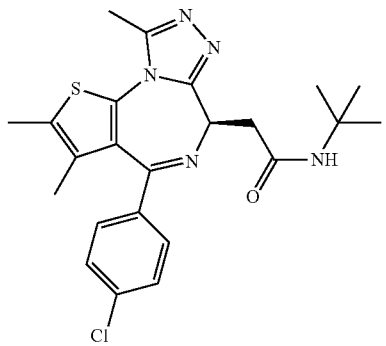\nChemical Formula: C_{23}H_{26}ClN_{5}OS\nExact Mass: 455.1547\nMolecular Weight: 456.0034 | 456.2 |
| JQ31 | 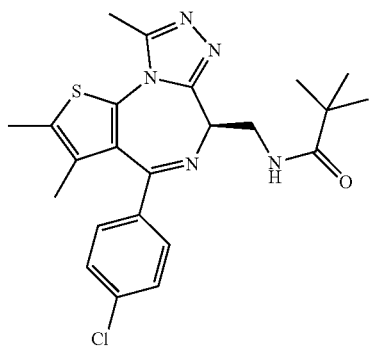\nChemical Formula: C_{23}H_{26}ClN_{5}OS\nExact Mass: 455.1547\nMolecular Weight: 456.0034 | 456.2 |
| JQ32 | 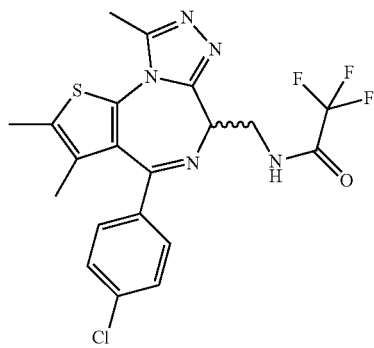\nChemical Formula: C_{20}H_{17}ClF_{3}N_{6}OS\nExact Mass: 467.0794\nMolecular Weight: 467.8951 | 468.1 |

-continued

| Compound Name | Structure | MS [M + H]+ m/z (Observed) |
|---|---|---|
| JQ33 | Chemical Formula: C25H29ClN8O2S<br>Exact Mass: 512.1761<br>Molecular Weight: 513.0548 | 512.2 |
| JQ34 | Chemical Formula: C26H25ClN6OS<br>Exact Mass: 504.1499<br>Molecular Weight: 505.0343 | 505.1 |
| JQ35 | Chemical Formula: C27H34ClN7OS<br>Exact Mass: 539.2234<br>Molecular Weight: 540.1232 | 540.2 |

| Compound Name | Structure | MS [M + H]+ m/z (Observed) |
|---|---|---|
| JQ36 | 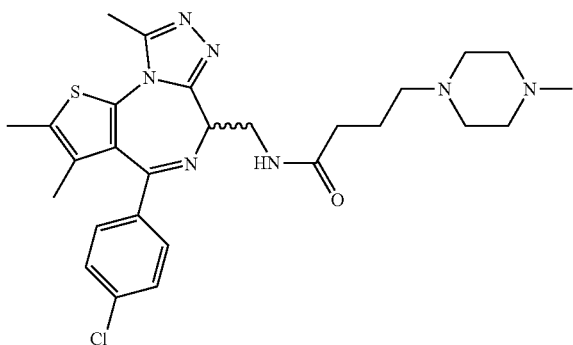<br>Chemical Formula: C$_{27}$H$_{34}$ClN$_7$OS<br>Exact Mass: 539.2234<br>Molecular Weight: 540.1232 | 540.2 |
| JQ37 | 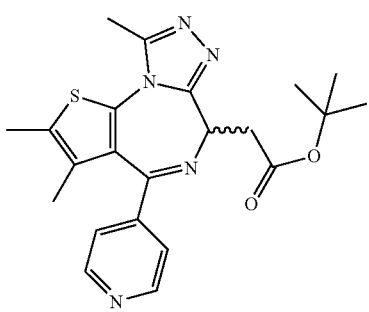<br>Chemical Formula: C$_{22}$H$_{26}$N$_5$O$_2$S<br>Exact Mass: 423.1729<br>Molecular Weight: 423.5312 | 424.2 |
| JQ38 | 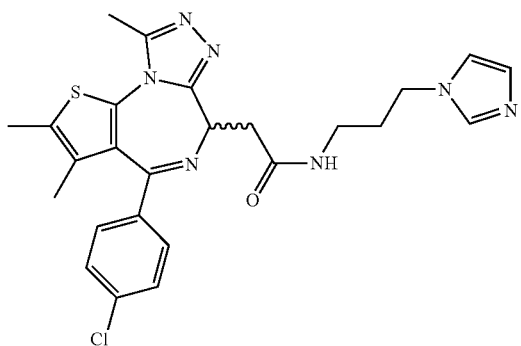<br>Chemical Formula: C$_{25}$H$_{25}$ClN$_7$OS<br>Exact Mass: 507.1608<br>Molecular Weight: 508.0362 | 508.2 |

| Compound Name | Structure | MS [M + H]+ m/z (Observed) |
|---|---|---|
| JQ39 | 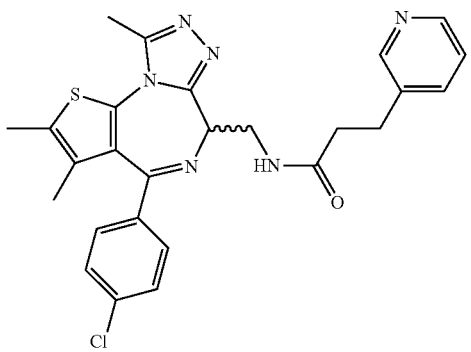<br>Chemical Formula: C$_{26}$H$_{25}$ClN$_6$OS<br>Exact Mass: 504.1499<br>Molecular Weight: 505.0343 | 505.1 |
| JQ40 | 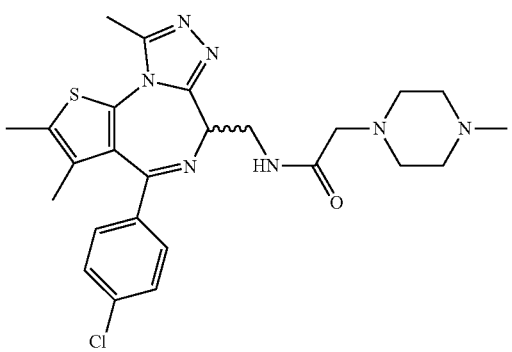<br>Chemical Formula: C$_{25}$H$_{30}$ClN$_7$OS<br>Exact Mass: 511.1921<br>Molecular Weight: 512.0700 | 512.2 |
| JQ41 | 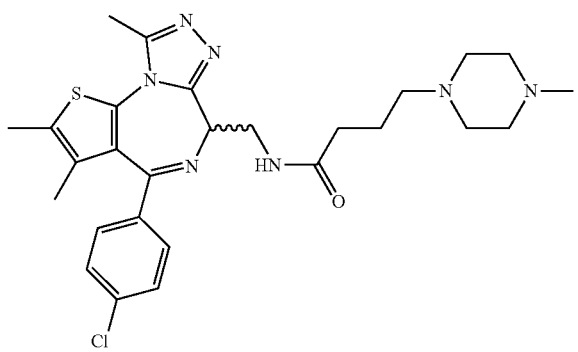<br>Chemical Formula: C$_{27}$H$_{34}$ClN$_7$OS<br>Exact Mass: 539.2234<br>Molecular Weight: 540.1232 | 540.2 |

-continued
| Compound Name | Structure | MS [M + H]+ m/z (Observed) |
|---|---|---|
| JQ42 | 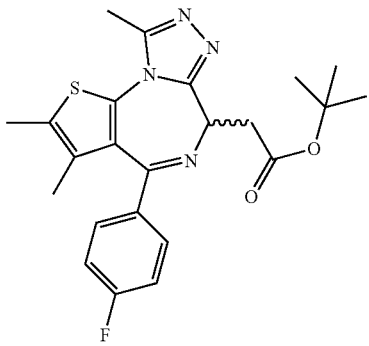  Chemical Formula: C23H25FN4O2S  Exact Mass: 440.1682  Molecular Weight: 440.5336 | 441.2 |
| JQ43 | 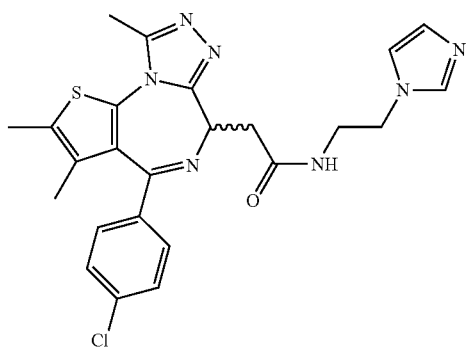  Chemical Formula: C24H24ClN7OS  Exact Mass: 493.1452  Molecular Weight: 494.0117 | 494.1 |
| JQ44 | 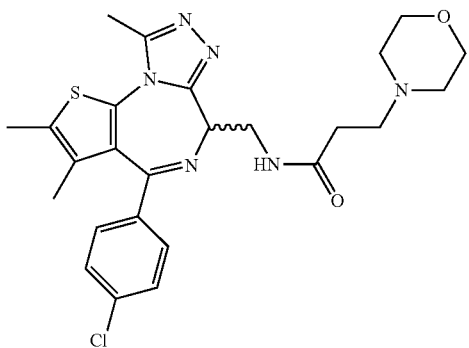  Chemical Formula: C25H29ClN6O2S  Exact Mass: 512.1761  Molecular Weight: 513.0548 | 513.2 |

| Compound Name | Structure | MS [M + H]+ m/z (Observed) |
|---|---|---|
| JQ45 | 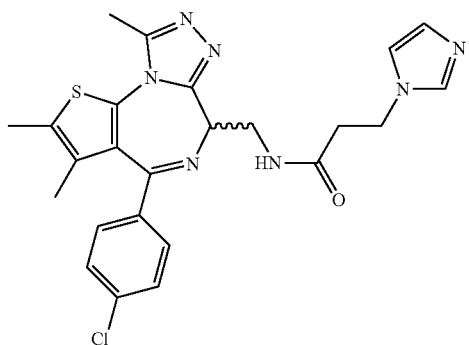<br>Chemical Formula: C$_{24}$H$_{24}$ClN$_7$OS<br>Exact Mass: 493.1452<br>Molecular Weight: 494.0117 | 494.1 |
| JQ46 | 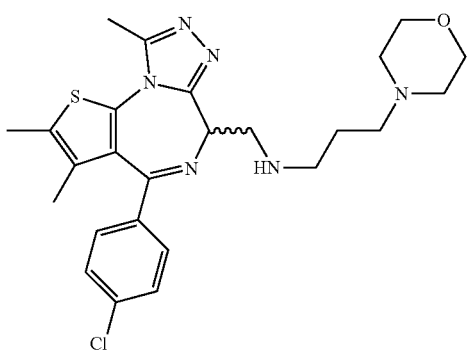<br>Chemical Formula: C$_{25}$H$_{31}$ClN$_6$OS<br>Exact Mass: 498.1969<br>Molecular Weight: 499.0712 | 499.2 |
| JQ47 | 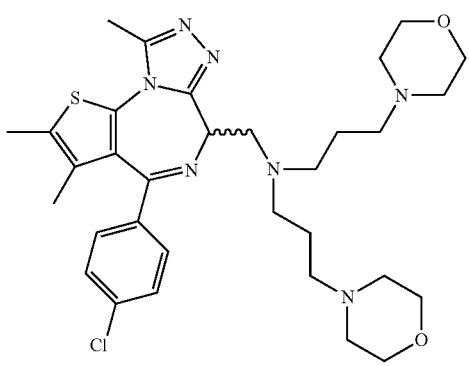<br>Chemical Formula: C$_{32}$H$_{44}$ClN$_7$O$_2$S<br>Exact Mass: 625.2966<br>Molecular Weight: 626.2555 | 626.3 |

-continued
| Compound Name | Structure | MS [M + H]+ m/z (Observed) |
|---|---|---|
| JQ48 | 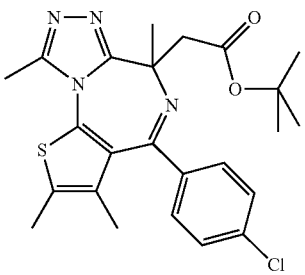<br>Exact Mass: 470.1543<br>Molecular Weight: 471.0146 | 471.2 |
| JQ49 | 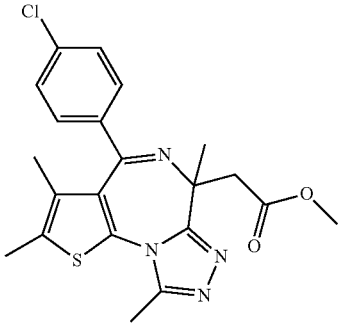<br>Exact Mass: 428.1074<br>Molecular Weight: 428.9350 | 429.1 |
| JQ50 | 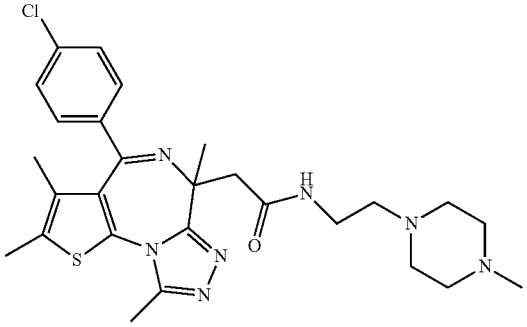<br>Exact Mass: 539.2234<br>Molecular Weight: 540.1232 | 540.2 |
| JQ51 | 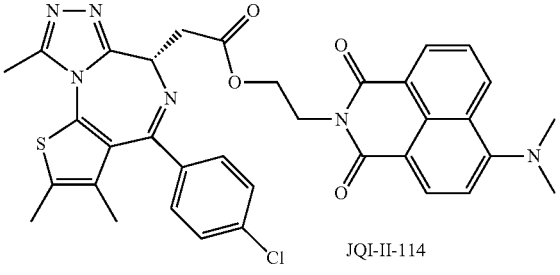<br>JQI-II-114<br>Exact Mass: 666.1816<br>Molecular Weight: 666.1764 | 667.2 |

-continued

| Compound Name | Structure | MS [M + H]+ m/z (Observed) |
|---|---|---|
| JQ52 | 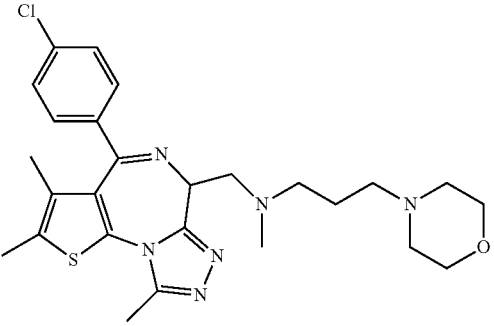<br>Exact Mass: 512.2126<br>Molecular Weight: 513.0978 | 513.2 |
| JQ53 | 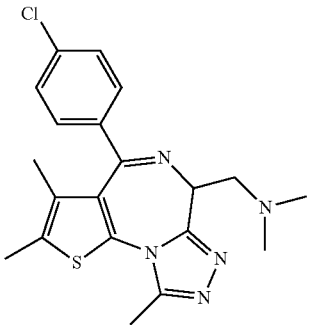<br>Exact Mass: 399.1284<br>Molecular Weight: 399.9402 | 400.1 |

Spectral data for each compound were consistent with the assigned structure.

II. Biological Activity and Methods of Treatment

Example 1

JQ1 is an Inhibitor of BRDT

Figure 2A:
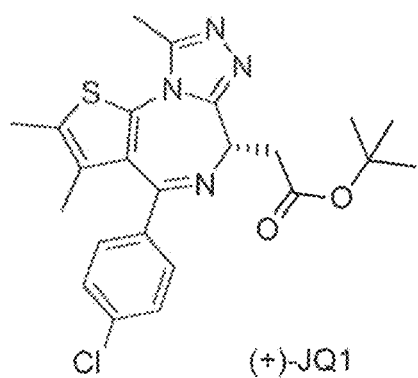
FIGS. 2A-2C show BRDT inhibition by (+)-JQ1.

The feasibility of targeting human bromodomains with acetyl-lysine competitive small molecules was recently established (Filippakopoulos et al., *Nature* 468:1067 (2010)). The index study identified a potent thienodiazepine inhibitor ((+)-JQ1; FIG. 2A; $K_d$=90 nM) of the BET family co-activator protein BRD4 (Filippakopoulos et al.), which is implicated in the pathogenesis of cancer. Protein sequence alignment of human BRD4(1) to human BRDT(1) reveals 81% identity and 89% similarity, including all surface residues predicted to contact (+)-JQ1 (FIGS. 1 and 3). Based on these insights and preliminary evidence of binding to BRDT(1) established by differential scanning fluorimetry (Filippakopoulos et al.), the biochemical and functional effects of (+)-JQ1 on BRDT(1) were evaluated.

Figure 2B:
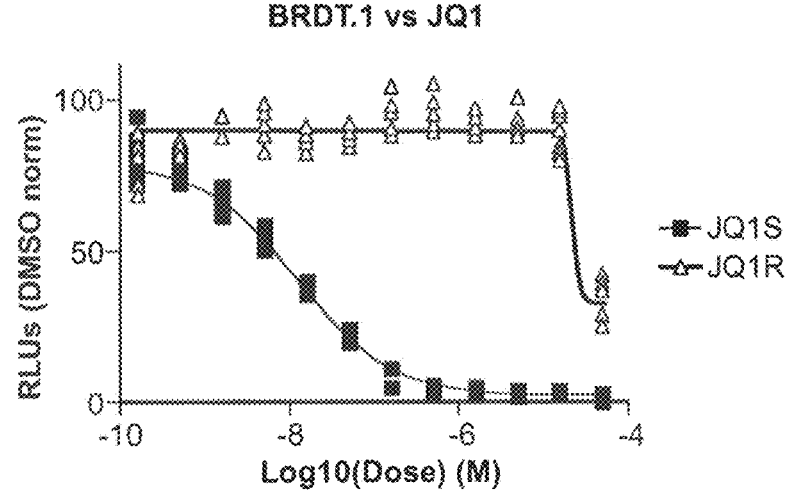
Figure 2C:
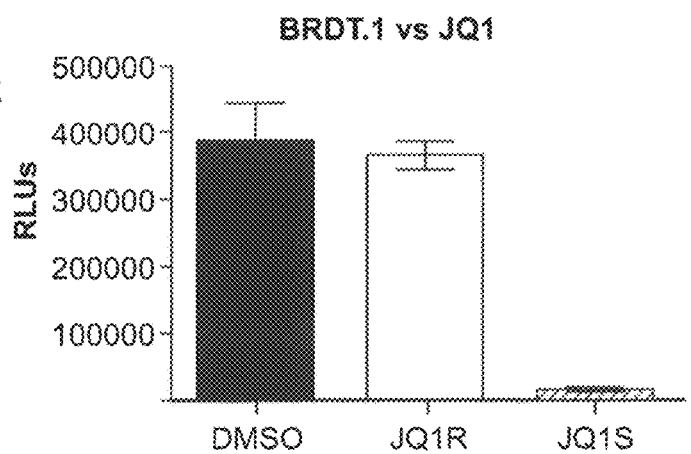

To assess competitive binding to BRDT(1), a homogeneous, luminescence proximity assay (alpha-screen), capable of quantifying binding of a synthetic, biotinylated tetra-acetylated histone 4 peptide (H4Kac4, residues 1-20) to recombinant epitope-tagged BRDT(1) was employed. Dose-ranging studies of (+)-JQ1 demonstrated potent inhibition of H4Kac4 binding, with a half-maximum inhibitory concentration ($IC_{50}$) value of 11 nM (FIG. 2B). In contrast, the (−)-JQ1 stereoisomer was inactive for BRDT(1), establishing a stereospecific, ligand-competitive binding event.

Example 2

JQ1 Inhibits BRDT Activity During Spermatogenesis

Figure 5A:
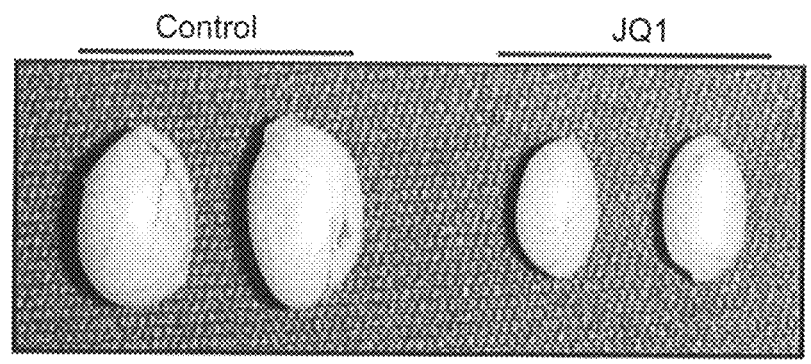
FIGS. 5A-5H show gross and histological analysis of testes from mice treated with JQ1 or vehicle control.
Figure 5B:
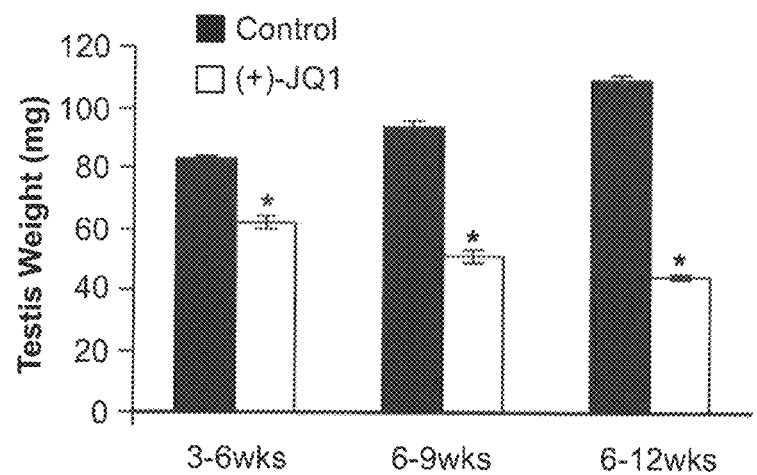
Figure 5C:
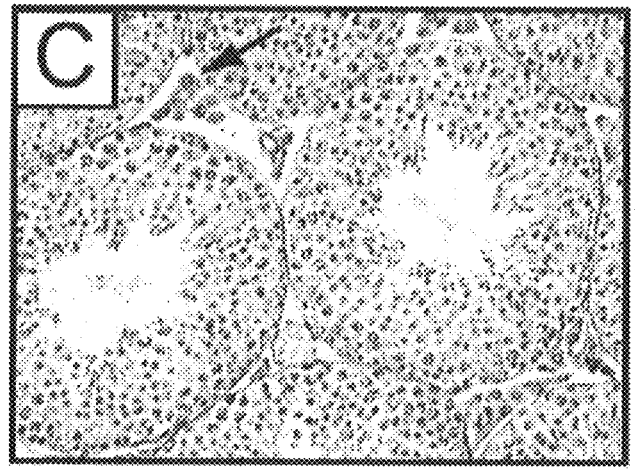

To determine the possible consequences of blocking BRDT function in vivo, the spermatogenic effects of JQ1 administered to male mice were evaluated. Murine BRDT (1) exhibits 90% amino acid sequence identity and 95% similarity to human BRDT(1), including all surface residues influencing molecular recognition (FIG. 4), supporting the validity of using JQ1 in murine model systems. Juvenile or adult C57BL6/J/129S5 hybrid male mice were administered daily intraperitoneal injections of JQ1 (50 mg/kg/day) or vehicle control over a 3- or 6-week period. After 3 weeks of treatment, mice were either sacrificed or mated to females while continuing to receive JQ1. The JQ1-treated males universally were observed to have grossly smaller testes compared to the control males (FIG. 5A). At each time point, males treated with JQ1 experienced a marked and significant reduction in testes volumes (FIG. 5B). Males treated from 3-6 weeks of age showed a reduction to 75.4% of control, males treated from 6-9 weeks of age showed a reduction to 54.7% of controls, and males treated for 6 weeks with JQ1

Figure 5D:
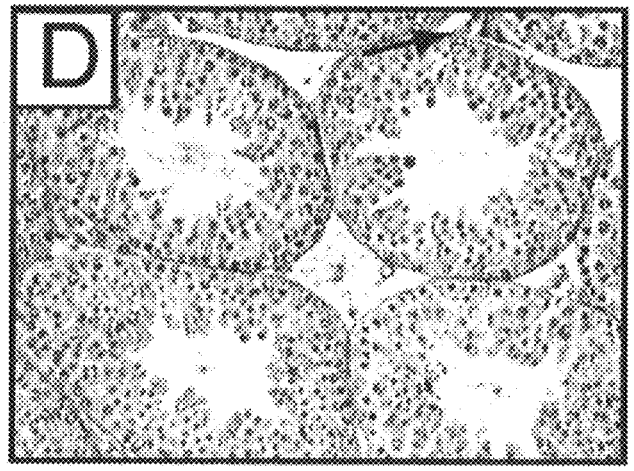
Figure 5E:
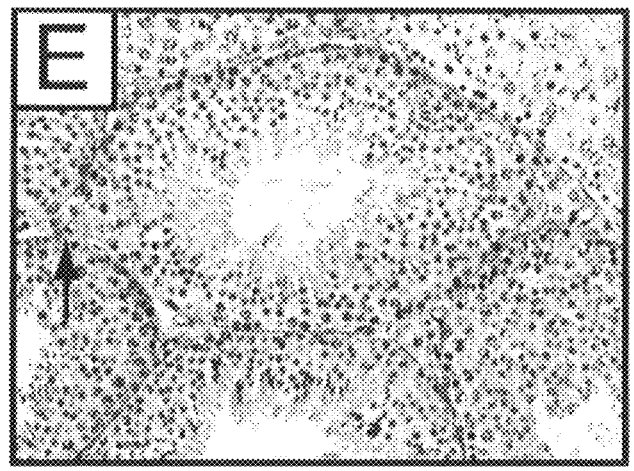
Figure 5F:
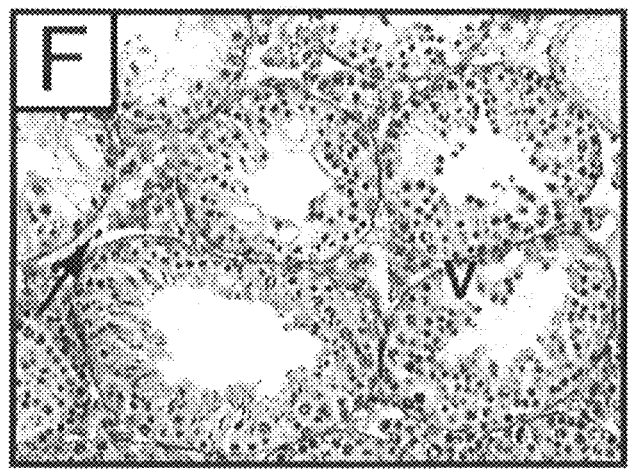
Figure 5G:
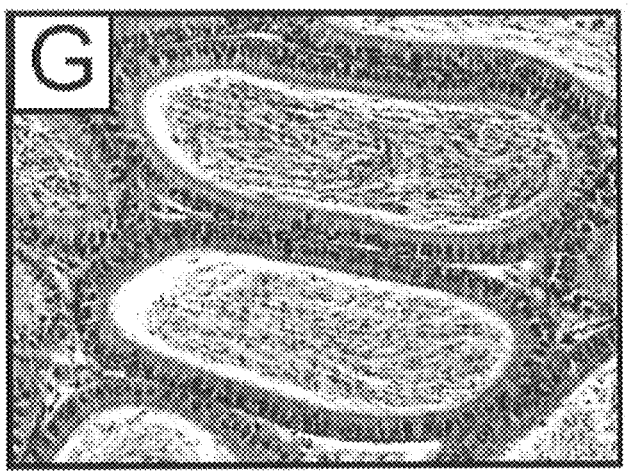
Figure 5H:
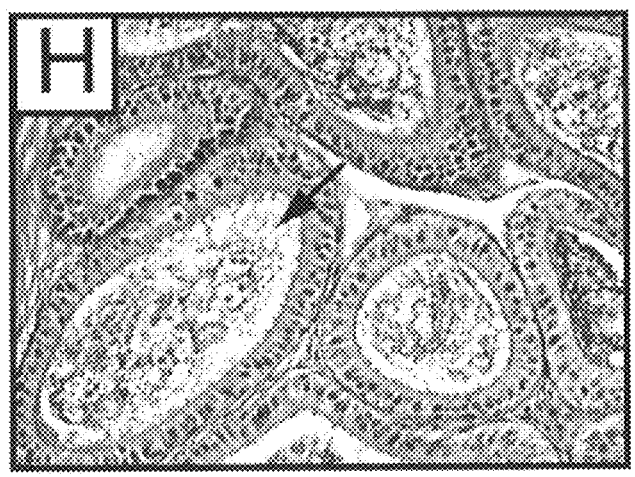
Figure 8A:
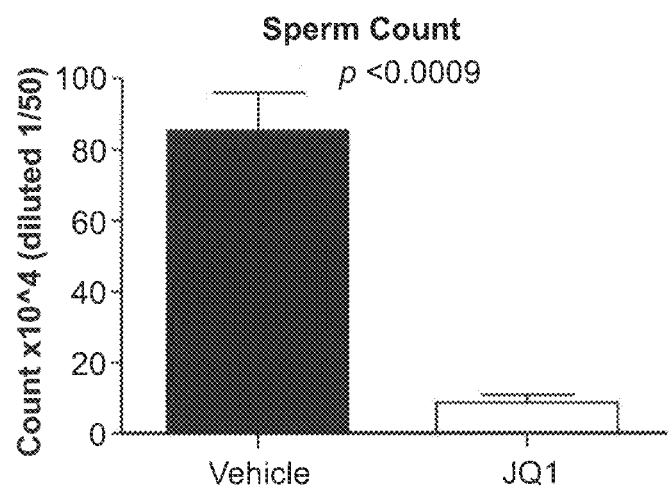
Figure 8B:
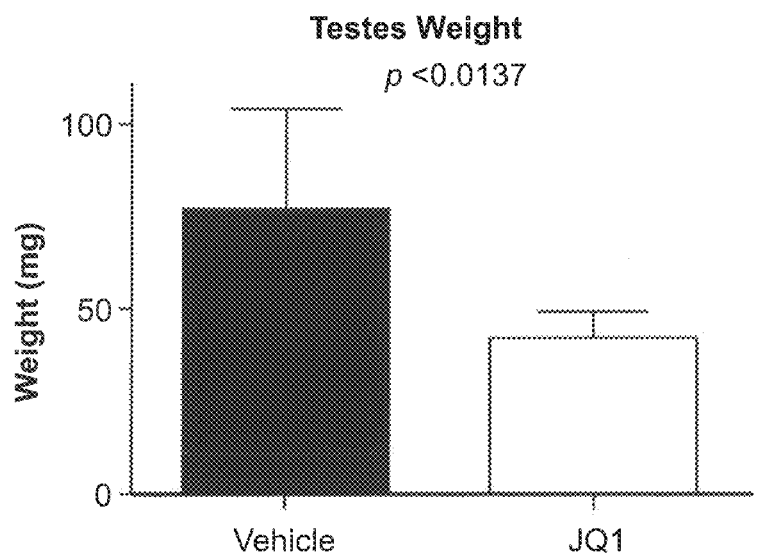

(6-12 weeks of age) showed the most dramatic reduction to 40.6% of the controls (FIG. 5B). Consistent with the reduction in testes volumes, the tubules of JQ1 treated males were narrower with a decrease in the amount and number of tubules that had obvious and abundant spermatozoa in their lumen (FIGS. 5C-5F). Whereas an abundance of seminiferous tubules from the control mice were observed to be full of spermatozoa (FIGS. 5C and 5E), the number of tubules with spermatozoa and the amount of spermatozoa in these tubules were reduced in the JQ1-treated males (FIGS. 5D and 5F). Consistent with the reduction in testes weights (FIG. 5), the most dramatic findings in the JQ1-treated males (6 weeks treatment) were seminiferous tubule degeneration where few tubules contained significant numbers of mature spermatozoa (FIGS. 5E and 5G). Histological analysis of the epididymides of JQ1-treated males also showed a similar finding in which fewer sperm were observed in the epididymal lumen compared to the abundance observed in the control (FIGS. 5G and 5H). These results are consistent with the findings from a repeat study in which C57B6 mice were treated with JQ1 (FIGS. 8A-8C)

Figure 6A:
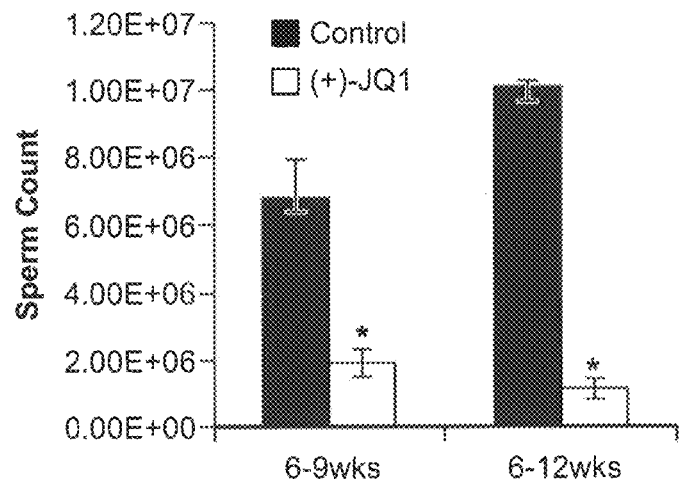
FIGS. 6A and 6B show epididymal sperm counts and fertilization potential.

To further characterize these defects, spermatozoa number was determined after 3 weeks of treatment (3-6 weeks of age). It was found that epididymal sperm number were reduced to 27.8% of the control while after 6 weeks of treatment, the sperm in the cauda epididymis of the JQ1-treated mice were 10.9% of the control (FIG. 6A). Furthermore, whereas 85% of the sperm from the cauda epididymis of the control showed progressive motility, JQ1 treatment resulted in only 5% of the spermatozoa with progressive motility. Thus, JQ1 treatment quantitatively reduced sperm number and qualitatively reduced sperm motility. These findings phenocopy those observed in mice deficient in BRDT(1) (Shang et al., Development 134:3507 (2007)). Furthermore, the testosterone producing intertubular Leydig cells of the testes of JQ1-treated males appeared to be histologically normal (FIG. 6), and there appeared to be no defects in androgen actions in these mice since the testosterone-responsive seminal vesicles of JQ1-treated males were grossly normal. Lastly, since JQ1 had a significant effect on the seminiferous tubule compartment, it must be capable of effectively crossing the blood:testis boundary to alter spermatogenesis.

Example 3

JQ1 is a Reversible Inhibitor of BRDT Activity

Figure 6B:
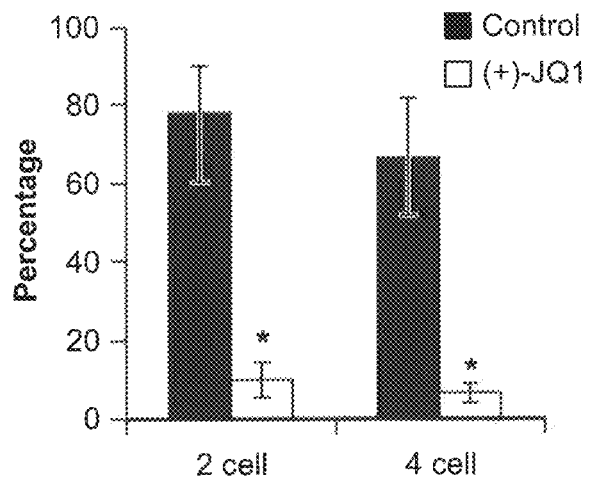
Figure 9A:
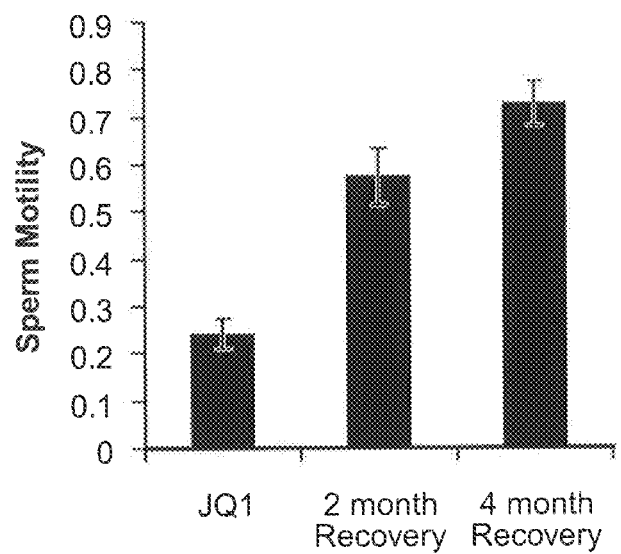
Figure 9B:
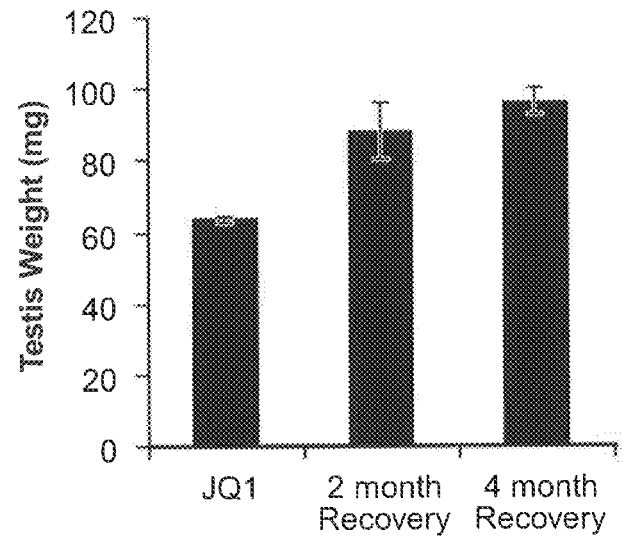

To further evaluate the consequences of JQ1 on male fertility and fertilization potential, control (n=2) and JQ1-treated (n=3) males treated for 3 weeks were housed with 2 females each and subjected to treatments for an additional 3 weeks. Whereas the control males impregnated all 4 females, JQ1 had a contraceptive effect on the males (one failed to impregnate the two females, whereas only 1 of 2 females in each of the other two cages became pregnant). When these same males were test bred to superovulated females (2 females per cage), after 5 weeks of treatment, all females demonstrated copulation plugs indicating that JQ1 did not alter mating behavior, consistent with normal testosterone-responsive tissues in these males. Oocytes from these females were collected from their oviductal ampulla and cultured for 2 days to determine their developmental potential post-mating (FIG. 6B). Whereas the majority of the oocytes from females mated to controls developed into 2 cell (72.8%) and 4 cell (70.1%) embryos, few of the oocytes from the females mated to JQ1 males developed into 2 cell (10.1%) or 4 cell (6.6%) embryos, consistent with their lower sperm counts, decreased motility, and fertility defects. Importantly, the effects of JQ1 on male fertility were found to be reversible. Following cessation of JQ1, 6 of 6 JQ1-treated adult male mice sired two litters of offspring (7.25+/−0.58 pups per litter) within the first ensuing month. These results are consistent with the findings that the sperm motility, testes weight, and sperm count in male mice returned towards normal levels after cessation of JQ1 treatment (FIGS. 9A-9C).

Example 4

Molecular Analysis of JQ1 Mediated BRDT Inhibition

Figure 7A:
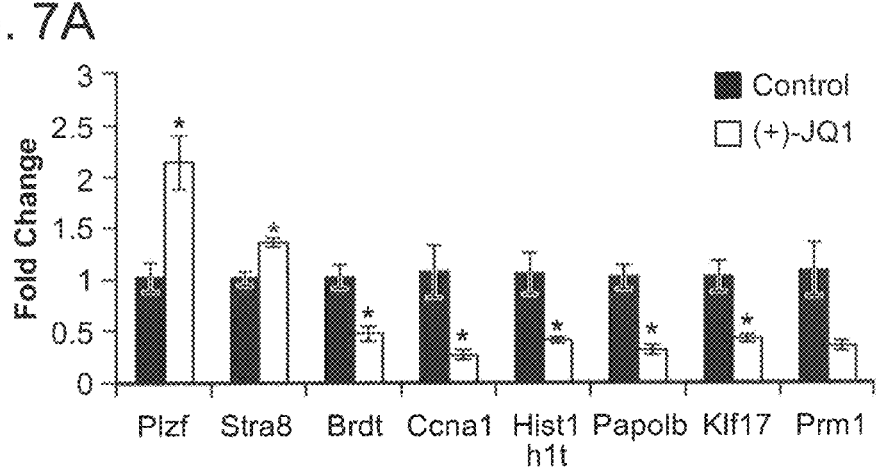
FIGS. 7A-7C show the molecular analysis of the testes of mice treated with JQ1 or control.
Figure 7B:
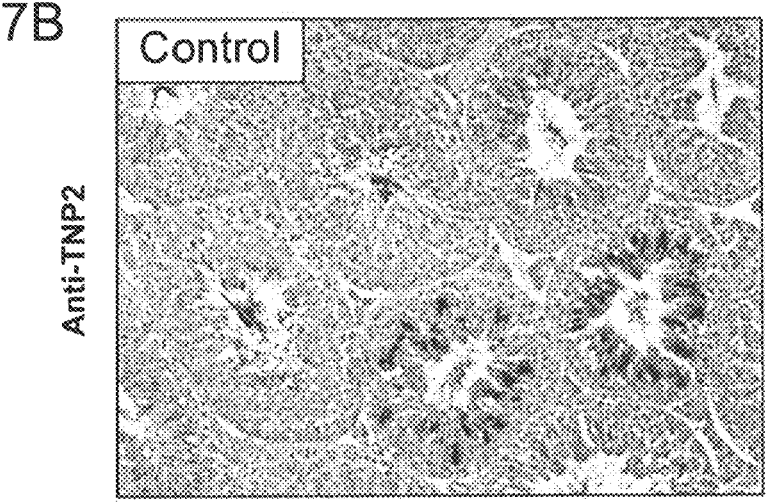
Figure 7C:
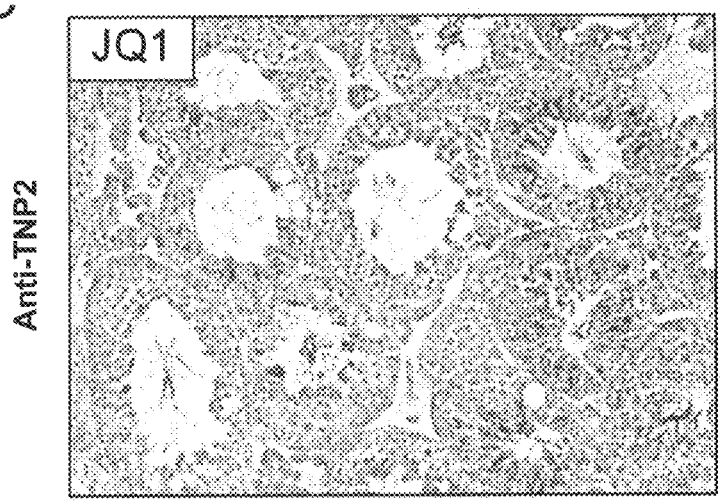

To molecularly define the stages of spermatogenesis at which JQ1 functions, quantitative RT-PCR was performed on testes isolated from JQ1-treated mice and controls (FIG. 7A). Genes expressed early in spermatogenesis such as Plzf, which is a marker for spermatogonial stem cells and early dividing spermatogonia (Buaas et al. Nat. Genet. 36:647 (2004); and Costoya et al., Nat. Genet. 36:653 (2004)), and Stra8, which is expressed mainly in differentiating spermatogonia and preleptotene spermatocytes (Zhou et al., Biol. Reprod. 79:35 (2008)), are 2.0-fold and 1.3-fold enriched, respectively, in the testes of JQ1-treated mice compared to control males. However, genes expressed during meiosis or spermiogenesis including Brdt (expressed in mid- to late-spermatocytes) (Shang et al., Gene Expr. Patterns 4:513 (2004)), Ccna1 (expressed in pachytene spermatocytes) (Sweeney et al., Development 122:53 (1996)), Papolb (expressed in step 1-7 round spermatids) (Kashiwabara et al., Dev. Biol. 228:106 (2000)), Klf17 (expressed in step 4-7 spermatids) (Van et al., Mech. Dev. 118:233 (2002)), and Prm1 (expressed in step 7-16 spermatids) (Kleene et al., Dev. Biol. 105:71 (1984)) are 2.1-fold to 4.0-fold lower in the testes of mice treated with JQ1 versus control. Unlike the Brdt knockout studies (Shang et al., Development 134:3507 (2007)) in which the pachytene spermatocyte-expressed gene, Hist1h1t, is upregulated, JQ1 treatment leads to a 2.6-fold downregulation of this gene in line with the suppression of Ccna1. Consistent with these mRNA findings and the histological analysis described above, JQ1 treatment reduced the number of spermatids positive for transition protein 1 (TNP1) (FIGS. 7B and 7C), which is expressed in the nuclei of step 10-15 spermatids (Zhao et al., Biol. Reprod. 71:1016 (2004)).

A pharmacologic approach to male contraception remains a longstanding challenge in medicine. The results described herein provide pharmacologic validation of the amino-terminal bromodomain of BRDT as a target for male contraception, using a highly potent and selective chemical probe. JQ1 emerges as a lead compound for a new class of drugs that can cross the blood:testis boundary, inhibit bromodomain activity during spermatogenesis, impair sperm generation and motility, reduce the number of oocytes fertilized, and produce a reversible contraceptive effect in mammals. As human and mouse BRDT proteins are highly conserved and have nearly identical bromodomain pockets based on our structural predictions, these discoveries can be completely translated to men, and provide a novel and efficacious strategy for a male contraceptive.

The results reported herein were obtained using the following methods and materials.

(+)-JQ1

The direct-acting, small-molecule bromodomain inhibitor was prepared as previously described (Filippakopoulos et al., *Nature* 468:1067 (2010)).

Protein Cloning, Expression and Purification

The N-terminal domain of human BRDT was cloned, expressed in *E-Coli* and purified as previously described (Filippakopoulos et al.).

BRDT Proximity Assay

Assays were performed with minor modifications from the manufacturer's protocol (PerkinElmer, USA). All reagents were diluted in 50 mM HEPES, 150 mM NaCl, 0.1% w/v BSA, 0.01% w/v Tween20, pH 7.5 and allowed to equilibrate to room temperature prior to addition to plates. After addition of Alpha beads to master solutions all subsequent steps were performed in low light conditions. A 2× solution of components with final concentrations of BRDT at 80 nM, Ni-coated Acceptor Bead at 25 µg/ml, and 80 nM biotinylated H4-tetra acetyl was added in 10 µL to 384-well plates (AlphaPlate-384, PerkinElmer, USA). Biotinylated peptide for BRDT was synthesized in-house on a CEM Liberty 9008005 microwave peptide synthesizer: H4-tetra acetyl, Biotin-PEG2-SGRGKacGGKacGLGKacG-GAKacRHRK-COOH. Addition to wells was performed with either a multichannel pipet (for optimization experiments) or a Biotek EL406 liquid handler. After a 1 minute 1000 rpm spin-down, 100 nl of compounds from stock plates were added by pin transfer using a Janus Workstation (PerkinElmer, USA). The streptavidin-coated donor beads (25 µg/ml final) were added as with previous solution in a 2×, 10 µl volume. Following this addition, the plates were sealed with foil to block light exposure and to prevent evaporation. The plates were spun down again at 1000 rpm for 1 minute. Next, the plates were incubated in the room with the plate reader (for temperature equilibration) for 1.5 hour prior to reading the assay. AlphaScreen measurements were performed on an Envision 2104 (PerkinElmer, USA) utilizing the manufacturer's protocol.

Sequence Alignment

Amino acid sequences for full-length bromodomain-containing proteins were obtained from the US National Heart, Lung and Blood Institute (Human BRDT accession number Q58F21; Human BRD4 accession number O60885; Mouse BRDT accession number Q91Y44). Multiple sequence alignments of full-length BRDT and BRD4 were generated using MAFFT (v6.240) (Katoh et al., *Nucleic Acids Res.* 33:511 (2005); Katoh et al., *Nucleic Acids Res.* 30:3059 (2002); and Katoh and Toh, *Brief Bioinform.* 9:286 (2008)). The E-INS-i algorithm was selected as suitable for sequences containing potentially large unalignable regions, and the BLOSUM62 scoring matrix was used as suitable for highly evolutionarily conserved sequences. Gap opening penalty and offset value were set to default parameters.

Mouse Studies (+)-JQ1 was dissolved in DMSO at 50 mg/ml and then diluted 1:10 in (2-Hydroxypropyl)-β-cyclodextrin (Sigma-Aldrich, St. Louis, Mo.). The subsequent mixture was injected intraperitoneal into male mice at 1% of the body weight of the mouse (final amount is 50 mg/kg/day). The control was DMSO dissolved 1:10 in (2-Hydroxypropyl)-β-cyclodextrin and injected similarly. Juvenile or adult C57BL6/J/129S5 hybrid mice for these studies were weighed daily before injections and fed ad libitum. These studies were approved by the Administrative Committee on Laboratory Animal Care at Baylor College of Medicine, and all experiments were conducted in accordance with the NIH guide for the Care and Use of Laboratory Animals.

Histological Analysis

Histological analysis of Bouin's fixed testes and epididymides was performed as previously described (Kumar et al., *Nature Genetics* 15:201 (1997)) using Periodic acid-Schiff and hematoxylin. Rabbit anti-TNP2 (1:600) staining and hematoxylin counter-staining was performed as described (Zhao et al., *Biol. Reprod.* 71:1016 (2004)) using Bouin's fixed testes.

Epididymal Sperm Counts

Counts were performed on spermatozoa isolated from the entire epididymis or from the caudal epididymis of adult mice as described (Roy et al., *Faseb J.* 21:1013 (2007)). In brief, epididymides were dissected and placed in prewarmed M2 medium, minced, and incubated at 37° C. in a incubator prior to counting.

Fertilization and Embryo Developmental Potential

To evaluate the ability of spermatozoa of treated mice to mate with females and fertilize oocytes, 21-day-old C57BL6/J/129S5 hybrid females were injected with 5 IU of pregnant mare serum gonadotropin (PMSG; Calbiochem, EMD, Gibbstown, N.J.) followed by 5 IU of human chorionic gonadotropin (hCG; Calbiochem, EMD, Gibbstown, N.J.) 48 hours later and mated to treated males. Oocytes were isolated from ampullas of oviducts of females with copulation plugs, counted, and cultured in M16 medium (Sigma-Aldrich, St. Louis, Mo.) for 24 hours (for counting of 2 cell embryos) and 48 hours (for counting of 4 cell embryos) as described (Andreu-Vieyra et al., *PLoS Biol.* 8:e1000453 (2010); and Burns et al., *Science* 300:633 (2003)).

Quantitative RT-PCR Analysis

Total RNAs from mouse testes were isolated using TRizol reagent (Invitrogen, Carlsbad, Calif.). Total RNA was then reversely transcribed using Superscript III reverse transcriptase (Invitrogen, Carlsbad, Calif.). Quantitative PCR was performed using SYBR green master mix and customized primers (Table 1).

TABLE 1

Primers for quantitative PCR

| Gene name | Forward | Reverse |
| --- | --- | --- |
| Plzf | TGGAGAAGCATTTGGGTATCTACTC | AAGACGGCATGCTCAACACA |
| Stra8 | GAGTGAGGCCCAGCATATGTC | CCTCTGGATTTTCTGAGTTGCA |
| Brdt | GCTTTGGGACTCCACAACTACTATG | GATTGTCCATTTTCCCCTTGATC |
| Ccna1 | TTTCCCCAATGCTGGTTGA | AACCAAAATCCGTTGCTTCT |

TABLE 1-continued

Primers for quantitative PCR

| Gene name | Forward | Reverse |
|---|---|---|
| His1h1t | GCTGATTCCTGAGGCCCTTT | CAGGGCAGCAAGGGACAT |
| Papolb | CGCCAACAGAGAAACAACATTTAG | CCAACCAGGATTCGGATCTTT |
| Klf17 | CCTCCCGTTTGTTCTCAACTTG | GGTGCATAGCCTGTTCCTTATTG |
| Prm1 | TGCACAGAATAGCAAGTCCATCA | TGTGGCGAGATGCTCTTGAA |

All quantitative PCR assays were conducted in duplicate for each sample. Gapdh was used as an internal control for the quantification.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference. The subject matter described herein may be related to subject matter of U.S. provisional applications 61/334,991, 61/370,745, and 61/375,663, each of which is incorporated herein by this reference.

What is claimed is:

1. A method of reducing or inhibiting spermatogenesis in a healthy fertile male subject, the method comprising administering an effective amount of a compound or a salt thereof that inhibits a bromodomain testis-specific protein (BRDT) to the male subject, wherein the compound is of Formula (I):

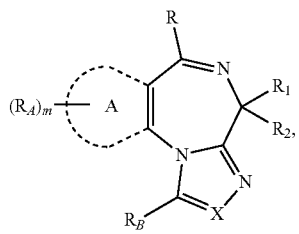

wherein:
X is N or $CR_5$;
$R_5$ is H, alkyl, cycloalkyl, heterocycloalkyl, aryl, or heteroaryl;
$R_B$ is H, alkyl, hydroxylalkyl, aminoalkyl, alkoxyalkyl, haloalkyl, hydroxy, alkoxy, or —COO—$R_3$, wherein alkyl is optionally substituted with halogen or —OH;
ring A is phenyl or thienyl;
each $R_A$ is independently alkyl, cycloalkyl, heterocycloalkyl, aryl, or heteroaryl, each of which is optionally substituted with halogen, amino, or —OH; or any two $R_A$ together with the atoms to which each is attached, can form a fused aryl or heteroaryl group;
R is alkyl, cycloalkyl, heterocycloalkyl, aryl, or heteroaryl; each of which is optionally substituted with halogen, alkyl, amino, —OH, or aryl;
$R_1$ is —$(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, aryl optionally substituted with alkyl, halogen, amino, or —OH, or heteroaryl optionally substituted with alkyl, halogen, amino, or —OH;
$R_2$ is H, D (deuterium), halogen, or alkyl optionally substituted with halogen, amino, or —OH;
each $R_3$ is independently selected from the group consisting of:
(i) H, aryl, or heteroaryl;
(ii) heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted with halogen, alkyl, amino, —OH, or heterocyclyl;
(iv) N=$CR_4R_6$;
each $R_4$ is independently H, alkyl, alkyl, cycloalkyl, heterocycloalkyl, aryl, or heteroaryl, each of which is optionally substituted with halogen, alkyl, amino, —$B(OH)_2$, —$SO_2Na$, or —OH;
or $R_3$ and $R_4$ are taken together with the nitrogen atom to which they are attached to form a 4-10-membered ring;
$R_6$ is alkyl, alkenyl, cycloalkyl, cycloalkenyl, heterocycloalkyl, aryl, or heteroaryl, each of which is optionally substituted with halogen, alkyl, amino, —$B(OH)_2$, —$SO_2Na$, or —OH; or $R_4$ and $R_6$ are taken together with the carbon atom to which they are attached to form a 4-10-membered ring;
m is 0, 1, 2, or 3;
wherein the compound contains a fluorine or chlorine atom.

2. A method of reducing the rate of male fertility in a healthy fertile male subject, the method comprising administering an effective amount of a compound or a salt thereof that inhibits a BRDT to the male subject, wherein the compound is of Formula (I):

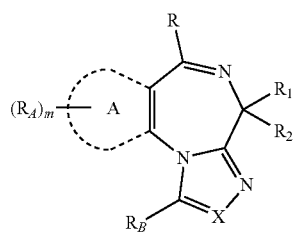

wherein:
X is N or $CR_5$;
$R_5$ is H, alkyl, cycloalkyl, heterocycloalkyl, aryl, or heteroaryl;
$R_B$ is H, alkyl, hydroxylalkyl, aminoalkyl, alkoxyalkyl, haloalkyl, hydroxy, alkoxy, or —COO—$R_3$, wherein alkyl is optionally substituted with halogen or —OH;
ring A is phenyl or thienyl;
each $R_A$ is independently alkyl, cycloalkyl, heterocycloalkyl, aryl, or heteroaryl, each of which is optionally substituted with halogen, amino, or —OH; or any two $R_A$ together with the atoms to which each is attached, can form a fused aryl or heteroaryl group;
R is alkyl, cycloalkyl, heterocycloalkyl, aryl, or heteroaryl; each of which is optionally substituted with halogen, alkyl, amino, —OH, or aryl;
$R_1$ is —$(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, aryl optionally substituted with alkyl, halogen, amino, or —OH, or heteroaryl optionally substituted with alkyl, halogen, amino, or —OH;
$R_2$ is H, D (deuterium), halogen, or alkyl optionally substituted with halogen, amino, or —OH;
each $R_3$ is independently selected from the group consisting of:
(i) H, aryl, or heteroaryl;
(ii) heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted with halogen, alkyl, amino, —OH, or heterocyclyl;
(iv) N=$CR_4R_6$;
each $R_4$ is independently H, alkyl, alkyl, cycloalkyl, heterocycloalkyl, aryl, or heteroaryl, each of which is optionally substituted with halogen, alkyl, amino, —$B(OH)_2$, —$SO_2Na$, or —OH;
or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted with halogen, alkyl, amino, —B(OH)$_2$, —SO$_2$Na, or —OH; or $R_4$ and $R_6$ are taken together with the carbon atom to which they are attached to form a 4-10-membered ring;

m is 0, 1, 2, or 3;

wherein the compound contains a fluorine or chlorine atom.

3. The method of claim 1, wherein the method comprises administering the compound or a salt thereof in an amount sufficient to reduce sperm number and/or reduce sperm motility.

4. The method of claim 1, wherein the method comprises administering the compound or a salt thereof in an amount sufficient to induce azoospermia, oligozoospermia, and/or asthenozoospermia.

5. The method of claim 4, wherein the method induces a contraceptive effect in the subject.

6. The method of claim 1, wherein the compound or a salt thereof is administered to the subject orally, transdermally, or by injection.

7. The method of claim 6, wherein the compound or a salt thereof is administered in the form of a tablet or capsule.

8. The method of claim 6, wherein the compound or a salt thereof is administered by parenteral injection, intramuscular injection, intravenous injection, subcutaneous implantation, subcutaneous injection, or transdermal preparation.

9. The method of claim 1, wherein the compound or a salt thereof is administered in combination with a pharmaceutically acceptable carrier, excipient, or diluent.

10. The method of claim 1, wherein the compound is JQ1 or a compound of Formula II:

(II)

wherein

X is N or CR$_5$;

$R_5$ is H, alkyl, cycloalkyl, heterocycloalkyl, aryl, or heteroaryl, each of which is optionally substituted;

$R_B$ is H, alkyl, hydroxylalkyl, aminoalkyl, alkoxyalkyl, haloalkyl, hydroxy, alkoxy, or —COO—R$_3$, each of which wherein alkyl is optionally substituted with halogen or —OH;

each $R_A$ is independently alkyl, cycloalkyl, heterocycloalkyl, aryl, or heteroaryl, each of which is optionally substituted with halogen, amino, or —OH; or any two $R_A$ together with the atoms to which each is attached, can form a fused aryl or heteroaryl group;

R is alkyl, cycloalkyl, heterocycloalkyl, aryl, or heteroaryl; each of which is optionally substituted with halogen, alkyl, amino, —OH, or aryl;

R'$_1$ is H, —COO—R$_3$, —CO—R$_3$, optionally substituted aryl, or optionally substituted heteroaryl, each of which is optionally substituted with halogen, amino, or —OH;

each $R_3$ is independently selected from the group consisting of:

(i) H, aryl, substituted aryl, or heteroaryl, or substituted heteroaryl;

(ii) heterocycloalkyl or substituted heterocycloalkyl;

(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted with halogen, alkyl, amino, —OH, or heterocyclyl;

m is 0, 1, 2, or 3, or salt thereof;

wherein the compound contains a fluorine or chlorine atom.

11. The method of claim 10, wherein the subject is human.

12. The method of claim 2, wherein the method comprises administering the compound or a salt thereof in an amount sufficient to reduce sperm number and/or reduce sperm motility.

13. The method of claim 2, wherein the method comprises administering the compound or a salt thereof in an amount sufficient to induce azoospermia, oligozoospermia, and/or asthenozoospermia.

14. The method of claim 13, wherein the method induces a contraceptive effect in the subject.

15. The method of claim 2, wherein the compound or a salt thereof is administered to the subject orally, transdermally, or by injection.

16. The method of claim 15, wherein the compound or a salt thereof is administered in the form of a tablet or capsule.

17. The method of claim 15, wherein the compound or a salt thereof is administered by parenteral injection, intramuscular injection, intravenous injection, subcutaneous implantation, subcutaneous injection, or transdermal preparation.

18. The method of claim 2, wherein the compound or a salt thereof is administered in combination with a pharmaceutically acceptable carrier, excipient, or diluent.

19. The method of claim 2, wherein the compound is JQ1 or a compound of Formula (I):

(I)

wherein:

X is N or CR$_5$;

$R_5$ is H, alkyl, cycloalkyl, heterocycloalkyl, aryl, or heteroaryl;

$R_B$ is H, alkyl, hydroxylalkyl, aminoalkyl, alkoxyalkyl, haloalkyl, hydroxy, alkoxy, or —COO—R$_3$, wherein alkyl is optionally substituted with halogen or —OH;

ring A is phenyl or thienyl;

each $R_A$ is independently alkyl, cycloalkyl, heterocycloalkyl, aryl, or heteroaryl, each of which is optionally substituted with halogen, amino, or —OH; or any two $R_A$ together with the atoms to which each is attached, can form a fused aryl or heteroaryl group;

R is alkyl, cycloalkyl, heterocycloalkyl, aryl, or heteroaryl; each of which is optionally substituted with halogen, alkyl, amino, —OH, or aryl;

$R_1$ is —(CH$_2$)$_n$-L, in which n is 0-3 and L is H, —COO—$R_3$, —CO—$R_3$, —CO—N($R_3R_4$), —S(O)$_2$—$R_3$, —S(O)$_2$—N($R_3R_4$), N($R_3R_4$), N($R_4$)C(O)$R_3$, aryl optionally substituted with alkyl, halogen, amino, or —OH, or heteroaryl optionally substituted with alkyl, halogen, amino, or —OH;

$R_2$ is H, D (deuterium), halogen, or alkyl optionally substituted with halogen, amino, or —OH;

each $R_3$ is independently selected from the group consisting of:
(i) H, aryl, or heteroaryl;
(ii) heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted with halogen, alkyl, amino, —OH, or heterocyclyl;
(iv) N=CR$_4$R$_6$;
each $R_4$ is independently H, alkyl, alkyl, cycloalkyl, heterocycloalkyl, aryl, or heteroaryl, each of which is optionally substituted with halogen, alkyl, amino, —B(OH)$_2$, —SO$_2$Na, or —OH;
or $R_3$ and $R_4$ are taken together with the nitrogen atom to which they are attached to form a 4-10-membered ring;
$R_6$ is alkyl, alkenyl, cycloalkyl, cycloalkenyl, heterocycloalkyl, aryl, or heteroaryl, each of which is optionally substituted with halogen, alkyl, amino, —B(OH)$_2$, —SO$_2$Na, or —OH; or $R_4$ and $R_6$ are taken together with the carbon atom to which they are attached to form a 4-10-membered ring;

m is 0, 1, 2, or 3;
or a salt thereof;
wherein the compound contains a fluorine or chlorine atom.

20. The method of claim 2, wherein the subject is human.

21. The method of claim 1, wherein the compound is JQ1 or a compound of Formula III:

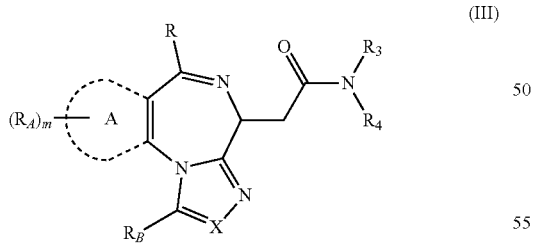

(III)

wherein
X is N or CR$_5$;
$R_5$ is H, alkyl, cycloalkyl, heterocycloalkyl, aryl, or heteroaryl;
$R_B$ is H, alkyl, hydroxylalkyl, aminoalkyl, alkoxyalkyl, haloalkyl, hydroxy, alkoxy, or —COO—$R_3$, wherein alkyl is optionally substituted with halogen or —OH;
ring A is phenyl or thienyl;
each $R_A$ is independently alkyl, cycloalkyl, heterocycloalkyl, aryl, or heteroaryl, each of which is optionally substituted with halogen, amino, or —OH; or any two $R_A$ together with the atoms to which each is attached, can form a fused aryl or heteroaryl group;

R is alkyl, cycloalkyl, heterocycloalkyl, aryl, or heteroaryl, each of which is optionally substituted with halogen, alkyl, amino, —OH, or aryl;

each $R_3$ is independently selected from the group consisting of:
(i) H, aryl, or heteroaryl;
(ii) heterocycloalkyl;
(iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted with halogen, alkyl, amino, —OH, or heterocyclyl; and
(iv) NH$_2$, N=CR$_4$R$_6$;
each $R_4$ is independently H, alkyl, alkyl, cycloalkyl, heterocycloalkyl, aryl, or heteroaryl, each of which is optionally substituted with halogen, alkyl, amino, —B(OH)$_2$, —SO$_2$Na, or —OH;
or $R_3$ and $R_4$ are taken together with the nitrogen atom to which they are attached to form a 4-10-membered ring;
$R_6$ is alkyl, alkenyl, cycloalkyl, cycloalkenyl, heterocycloalkyl, aryl, or heteroaryl, each of which is optionally substituted with halogen, alkyl, amino, —B(OH)$_2$, —SO$_2$Na, or —OH; or $R_4$ and $R_6$ are taken together with the carbon atom to which they are attached to form a 4-10-membered ring; and m is 0, 1, 2, or 3;
wherein the compound contains a fluorine or chlorine atom.

22. The method of claim 1, wherein the compound is JQ1 or a compound of Formula IV:

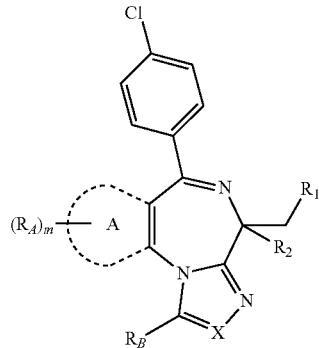

(IV)

wherein
X is N or CR$_5$;
$R_5$ is H, alkyl, cycloalkyl, heterocycloalkyl, aryl, or heteroaryl;
$R_B$ is H, alkyl, hydroxylalkyl, aminoalkyl, alkoxyalkyl, haloalkyl, hydroxy, alkoxy, or —COO—$R_3$, wherein alkyl is optionally substituted with halogen or —OH;
ring A is phenyl or thienyl;
each $R_A$ is independently alkyl, cycloalkyl, heterocycloalkyl, aryl, or heteroaryl, each of which is optionally substituted with halogen, amino, or —OH; or any two $R_A$ together with the atoms to which each is attached, can form a fused aryl or heteroaryl group;

R₁ is —(CH₂)ₙ-L, in which n is 0-3 and L is H, —COO—R₃, —CO—R₃, —CO—N(R₃R₄), —S(O)₂—R₃, —S(O)₂—N(R₃R₄), N(R₃R₄), N(R₄)C(O)R₃, aryl optionally substituted with alkyl, halogen, amino, or —OH, or heteroaryl optionally substituted with alkyl, halogen, amino, or —OH;

R₂ is H, D (deuterium), halogen, or alkyl optionally substituted with halogen, amino, or —OH;

each R₃ is independently selected from the group consisting of:

(i) H, aryl, or heteroaryl;

(ii) heterocycloalkyl;

(iii) —C₁-C₈ alkyl, —C₂-C₈ alkenyl or —C₂-C₈ alkynyl, each containing 0, 1, 2, or 3 heteroatoms selected from O, S, or N; —C₃-C₁₂ cycloalkyl, substituted —C₃-C₁₂ cycloalkyl, —C₃-C₁₂ cycloalkenyl, or substituted —C₃-C₁₂ cycloalkenyl, each of which may be optionally substituted with halogen, alkyl, amino, —OH, or heterocyclyl; and (iv) N=CR₄R₆;

each R₄ is independently H, alkyl, alkyl, cycloalkyl, heterocycloalkyl, aryl, or heteroaryl, each of which is optionally substituted with halogen, alkyl, amino, —B(OH)₂, —SO₂Na, or —OH;

or R₃ and R₄ are taken together with the nitrogen atom to which they are attached to form a 4-10-membered ring;

R₆ is alkyl, alkenyl, cycloalkyl, cycloalkenyl, heterocycloalkyl, aryl, or heteroaryl, each of which is optionally substituted with halogen, alkyl, amino, —B(OH)₂, —SO₂Na, or —OH; or R₄ and R₆ are taken together with the carbon atom to which they are attached to form a 4-10-membered ring; and m is 0, 1, 2, or 3;

wherein the compound contains a fluorine or chlorine atom.

23. The method of claim 1, wherein the compound is JQ1 or a compound of Formulae V-XXII:

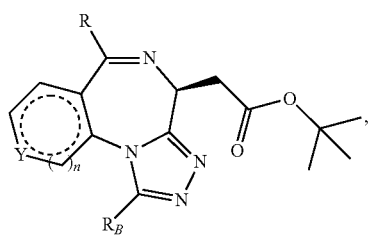

(V)

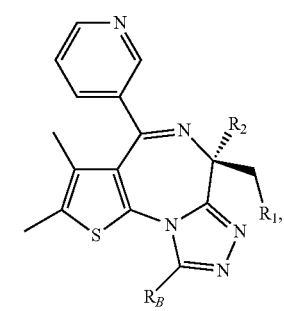

(VI)

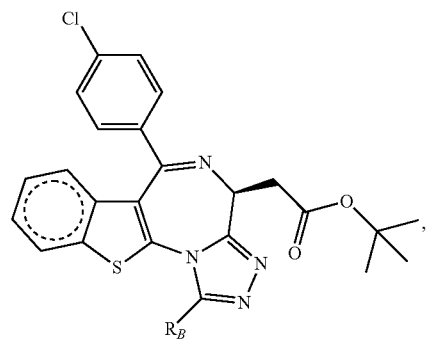

(VII)

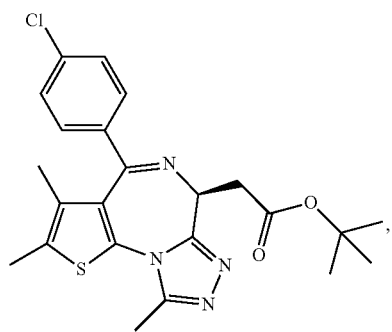

(VIII)

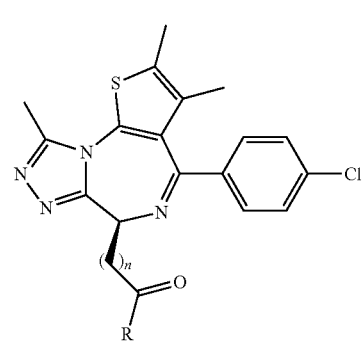

(IX)

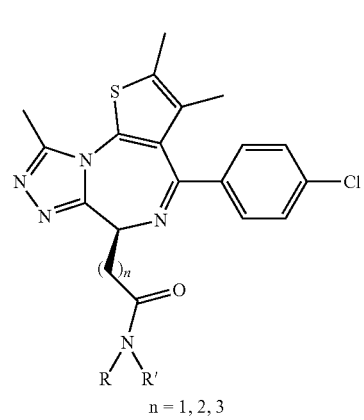

(X)

-continued
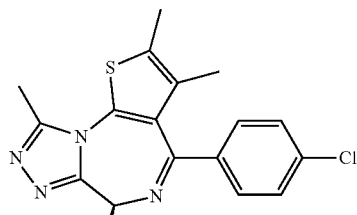
(XI)
n = 1, 2, 3
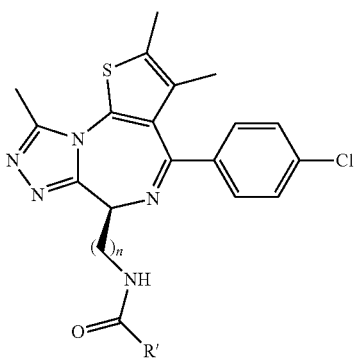
(XII)
n = 1, 2, 3
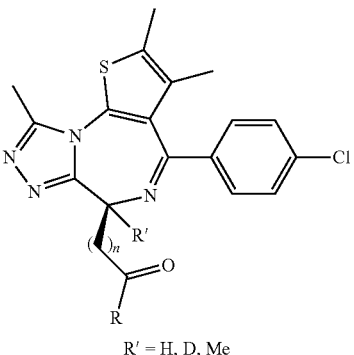
(XIII)
R' = H, D, Me
n = 1, 2, 3
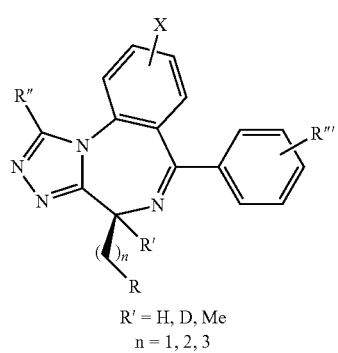
(XIV)
R' = H, D, Me
n = 1, 2, 3
-continued
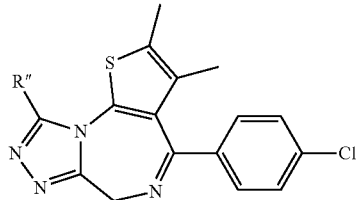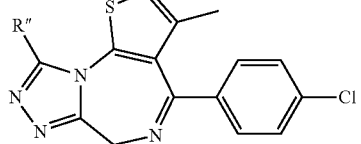
(XV)
R'' = OMe, CH$_2$OH, CH$_2$NH$_2$, CH$_2$OMe
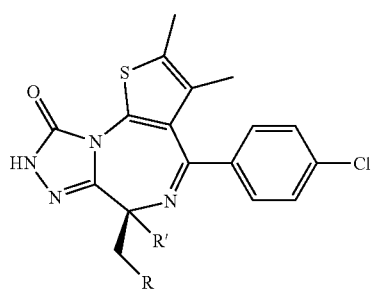
(XVI)
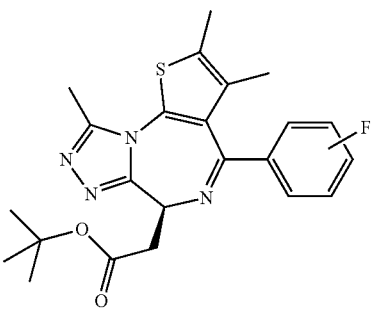
(XVII)
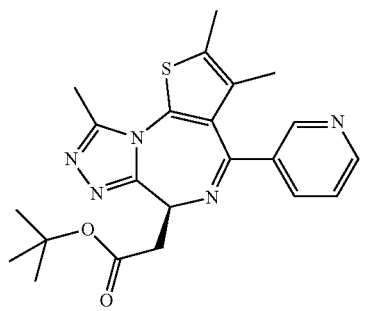
(XVIII)
Also 2- and 4-pyridyl
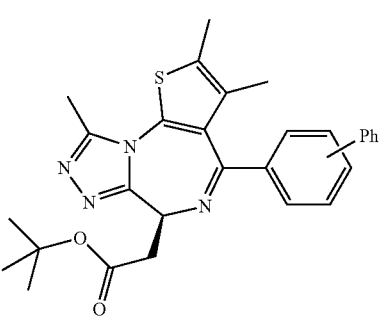
(XIX)

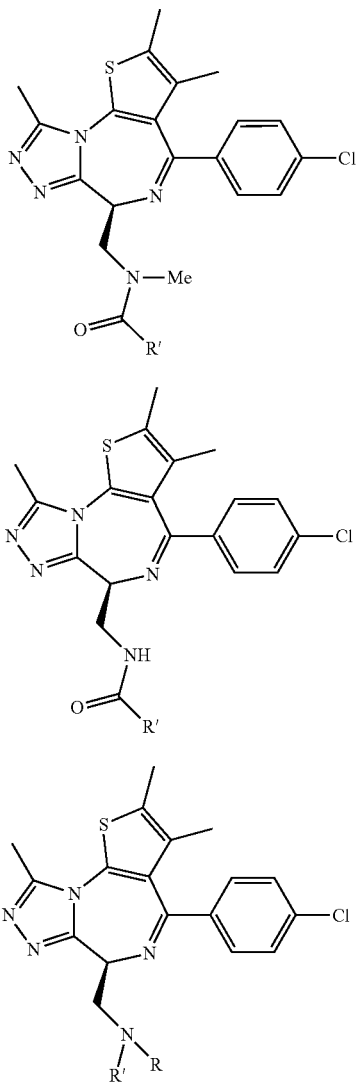

(XX)

(XXI)

(XXII)

wherein:
- R is H, aryl, substituted aryl, heteroaryl, heteroaryl, heterocycloalkyl, —$C_1$-$C_8$ alkyl, —$C_2$-$C_8$ alkenyl, —$C_2$-$C_8$ alkynyl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted with halogen, alkyl, amino, —OH, or aryl;
- R' is H, aryl, substituted aryl, heteroaryl, heteroaryl, heterocycloalkyl, —$C_1$-$C_8$ alkyl, —$C_2$-$C_8$ alkenyl, —$C_2$-$C_8$ alkynyl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted with halogen, amino, or —OH; and
- X is a substituent of an aryl group;
- wherein the compound contains a fluorine or chlorine atom.

24. The method of claim 2, wherein the compound is JQ1 or a compound of Formula III:

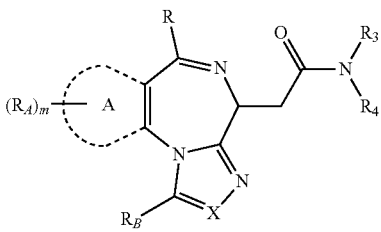

(III)

wherein
- X is N or $CR_5$;
  - $R_5$ is H, alkyl, cycloalkyl, heterocycloalkyl, aryl, or heteroaryl;
  - $R_B$ is H, alkyl, hydroxylalkyl, aminoalkyl, alkoxyalkyl, haloalkyl, hydroxy, alkoxy, or —COO—$R_3$, wherein alkyl is optionally substituted with halogen or —OH;
- ring A is phenyl or thienyl;
  - each $R_A$ is independently alkyl, cycloalkyl, heterocycloalkyl, aryl, or heteroaryl, each of which is optionally substituted with halogen, amino, or —OH; or any two $R_A$ together with the atoms to which each is attached, can form a fused aryl or heteroaryl group;
- R is alkyl, cycloalkyl, heterocycloalkyl, aryl, or heteroaryl; each of which is optionally substituted with halogen, alkyl, amino, —OH, or aryl;
- each $R_3$ is independently selected from the group consisting of:
  - (i) H, aryl, or heteroaryl;
  - (ii) heterocycloalkyl;
  - (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted with halogen, alkyl, amino, —OH, or heterocyclyl; and
  - (iv) $NH_2$, N=$CR_4R_6$;
    - each $R_4$ is independently H, alkyl, alkyl, cycloalkyl, heterocycloalkyl, aryl, or heteroaryl, each of which is optionally substituted with halogen, alkyl, amino, —$B(OH)_2$, —$SO_2Na$, or —OH;
    - or $R_3$ and $R_4$ are taken together with the nitrogen atom to which they are attached to form a 4-10-membered ring;
  - $R_6$ is alkyl, alkenyl, cycloalkyl, cycloalkenyl, heterocycloalkyl, aryl, or heteroaryl, each of which is optionally substituted with halogen, alkyl, amino, —$B(OH)_2$, —$SO_2Na$, or —OH; or $R_4$ and $R_6$ are taken together with the carbon atom to which they are attached to form a 4-10-membered ring; and
- m is 0, 1, 2, or 3;
- wherein the compound contains a fluorine or chlorine atom.

25. The method of claim 2, wherein the compound is JQ1 or a compound of Formula IV:

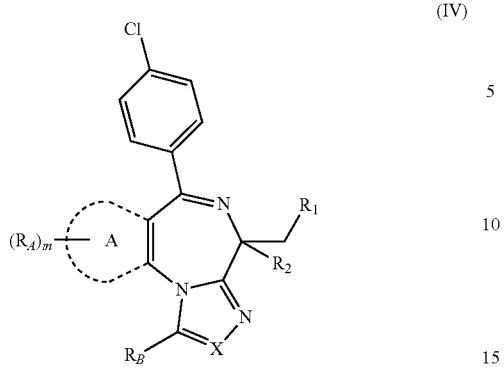

(IV)

wherein
X is N or CR$_5$;
  R$_5$ is H, alkyl, cycloalkyl, heterocycloalkyl, aryl, or heteroaryl;
  R$_B$ is H, alkyl, hydroxylalkyl, aminoalkyl, alkoxyalkyl, haloalkyl, hydroxy, alkoxy, or —COO—R$_3$, wherein alkyl is optionally substituted with halogen or —OH;
ring A is phenyl or thienyl;
  each R$_A$ is independently alkyl, cycloalkyl, heterocycloalkyl, aryl, or heteroaryl, each of which is optionally substituted with halogen, amino, or —OH; or any two R$_A$ together with the atoms to which each is attached, can form a fused aryl or heteroaryl group;
R$_1$ is —(CH$_2$)$_n$-L, in which n is 0-3 and L is H, —COO—R$_3$, —CO—R$_3$, —CO—N(R$_3$R$_4$), —S(O)$_2$—R$_3$, —S(O)$_2$—N(R$_3$R$_4$), N(R$_3$R$_4$), N(R$_4$)C(O)R$_3$, aryl optionally substituted with alkyl, halogen, amino, or —OH, or heteroaryl optionally substituted with alkyl, halogen, amino, or —OH;
R$_2$ is H, D (deuterium), halogen, or alkyl optionally substituted with halogen, amino, or —OH;
each R$_3$ is independently selected from the group consisting of:
  (i) H, aryl, or heteroaryl;
  (ii) heterocycloalkyl;
  (iii) —C$_1$-C$_8$ alkyl, —C$_2$-C$_8$ alkenyl or —C$_2$-C$_8$ alkynyl, each containing 0, 1, 2, or 3 heteroatoms selected from O, S, or N; —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted with halogen, alkyl, amino, —OH, or heterocyclyl; and
  (iv) N=CR$_4$R$_6$;
    each R$_4$ is independently H, alkyl, alkyl, cycloalkyl, heterocycloalkyl, aryl, or heteroaryl, each of which is optionally substituted with halogen, alkyl, amino, —B(OH)$_2$, —SO$_2$Na, or —OH;
    or R$_3$ and R$_4$ are taken together with the nitrogen atom to which they are attached to form a 4-10-membered ring;
  R$_6$ is alkyl, alkenyl, cycloalkyl, cycloalkenyl, heterocycloalkyl, aryl, or heteroaryl, each of which is optionally substituted with halogen, alkyl, amino, —B(OH)$_2$, —SO$_2$Na, or —OH; or R$_4$ and R$_6$ are taken together with the carbon atom to which they are attached to form a 4-10-membered ring; and
m is 0, 1, 2, or 3;
wherein the compound contains a fluorine or chlorine atom.
26. The method of claim 2, wherein the compound is JQ1 or a compound of Formulae V-XXII:

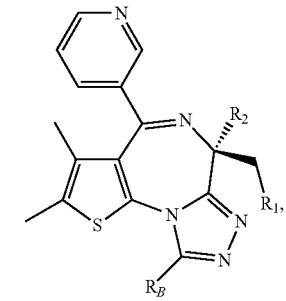

(V)

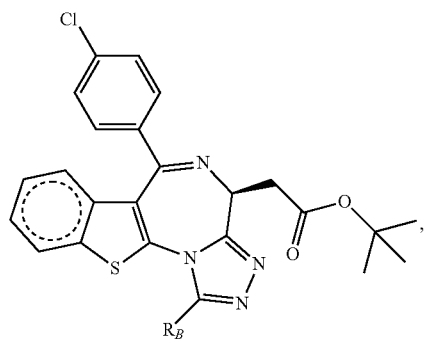

(VI)

(VII)

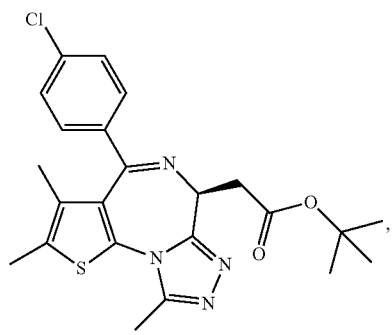

(VIII)

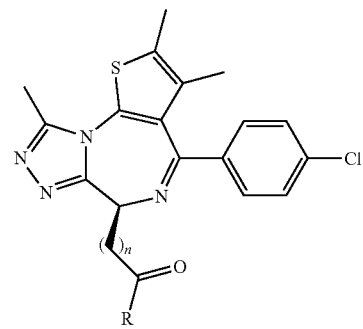

(IX)

n = 1, 2, 3

(X)
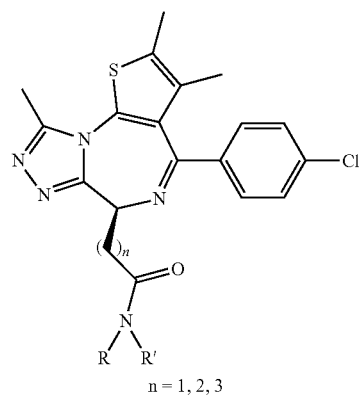
n = 1, 2, 3
(XI)
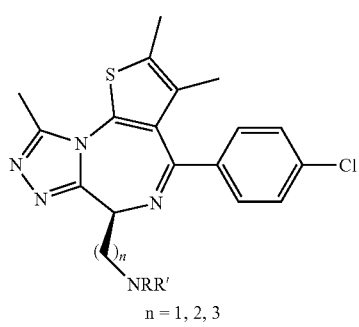
n = 1, 2, 3
(XII)
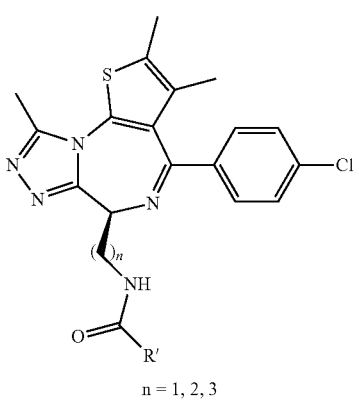
n = 1, 2, 3
(XIII)
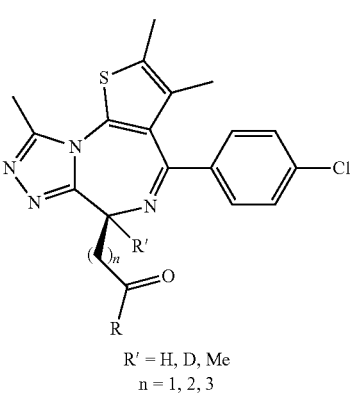
R' = H, D, Me
n = 1, 2, 3
(XIV)
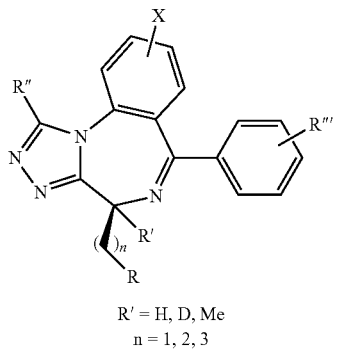
R' = H, D, Me
n = 1, 2, 3
(XV)
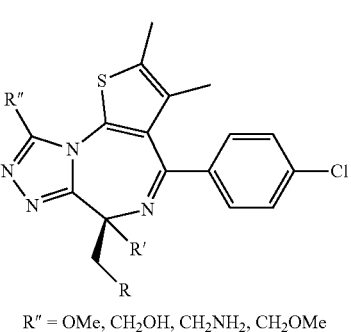
R'' = OMe, CH$_2$OH, CH$_2$NH$_2$, CH$_2$OMe
(XVI)
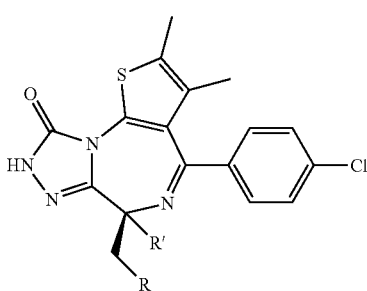
(XVII)
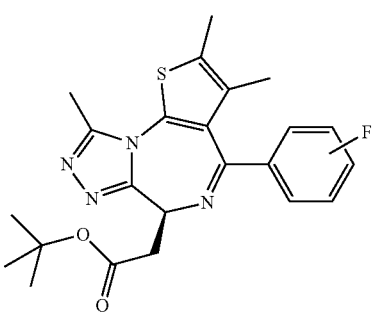
(XVIII)
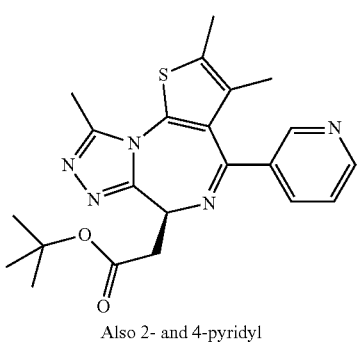
Also 2- and 4-pyridyl (XIX)

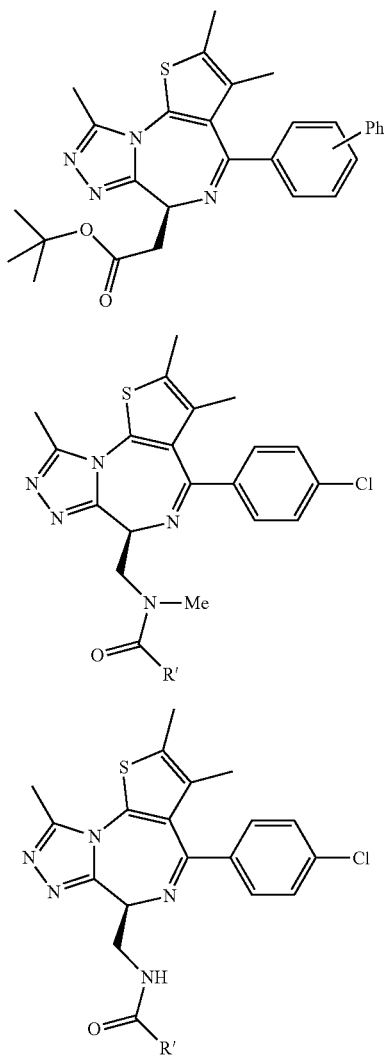

(XX)

(XXI)

-continued (XXII)

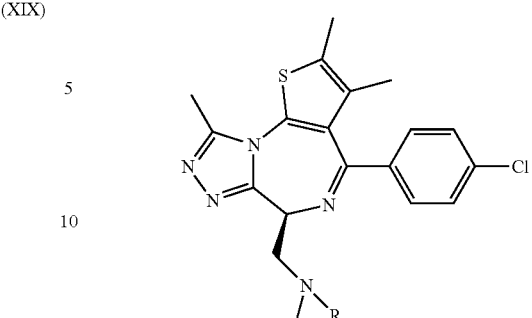

wherein:
R is H, aryl, substituted aryl, heteroaryl, heteroaryl, heterocycloalkyl, —C$_1$-C$_8$ alkyl, —C$_2$-C$_8$ alkenyl, —C$_2$-C$_8$ alkynyl, —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted with halogen, alkyl, amino, —OH, or aryl;

R' is H, aryl, substituted aryl, heteroaryl, heteroaryl, heterocycloalkyl, —C$_1$-C$_8$ alkyl, —C$_2$-C$_8$ alkenyl, —C$_2$-C$_8$ alkynyl, —C$_3$-C$_{12}$ cycloalkyl, substituted —C$_3$-C$_{12}$ cycloalkyl, —C$_3$-C$_{12}$ cycloalkenyl, or substituted —C$_3$-C$_{12}$ cycloalkenyl, each of which may be optionally substituted with halogen, amino, or —OH; and X is a substituent of an aryl group;
Y is C; and n is 1 in Formula (V);
wherein the compound contains a fluorine or chlorine atom.

* * * * *

UNITED STATES PATENT AND TRADEMARK OFFICE
CERTIFICATE OF CORRECTION

PATENT NO. : 9,789,120 B2
APPLICATION NO. : 14/977343
DATED : October 17, 2017
INVENTOR(S) : James E. Bradner et al.

Page 1 of 1

It is certified that error appears in the above-identified patent and that said Letters Patent is hereby corrected as shown below:

In the Specification

Column 1, Lines 21-25, change the paragraph:
"This work was supported by the following grant from the National Institutes of Health, Grant No: K08CA128972 (Bradner). The government has certain rights in the invention."

To:
-- This invention was made with government support under grant number K08 CA128972 awarded by The National Institutes of Health. The government has certain rights in the invention. --

Signed and Sealed this
Twenty-second Day of October, 2019

Andrei Iancu
*Director of the United States Patent and Trademark Office*

SEQUENCE LISTING

```
<160> NUMBER OF SEQ ID NOS: 20

<210> SEQ ID NO 1
<211> LENGTH: 801
<212> TYPE: PRT
<213> ORGANISM: Homo sapiens

<400> SEQUENCE: 1

Met Leu Gln Asn Val Thr Pro His Asn Lys Leu Pro Gly Glu Gly Asn
 1               5                  10                  15

Ala Gly Leu Leu Gly Leu Gly Pro Glu Ala Ala Pro Gly Lys Arg
                20                  25                  30

Ile Arg Lys Pro Ser Leu Leu Tyr Glu Gly Phe Glu Ser Pro Thr Met
            35                  40                  45

Ala Ser Val Pro Ala Leu Gln Leu Thr Pro Ala Asn Pro Pro Pro Pro
        50                  55                  60

Glu Val Ser Asn Pro Lys Lys Pro Gly Arg Val Thr Asn Gln Leu Gln
65                  70                  75                  80

Tyr Leu His Lys Val Val Met Lys Ala Leu Trp Lys His Gln Phe Ala
                85                  90                  95

Trp Pro Phe Arg Gln Pro Val Asp Ala Val Lys Leu Gly Leu Pro Asp
                100                 105                 110

Tyr His Lys Ile Ile Lys Gln Pro Met Asp Met Gly Thr Ile Lys Arg
            115                 120                 125

Arg Leu Glu Asn Asn Tyr Tyr Trp Ala Ala Ser Glu Cys Met Gln Asp
        130                 135                 140

Phe Asn Thr Met Phe Thr Asn Cys Tyr Ile Tyr Asn Lys Pro Thr Asp
145                 150                 155                 160

Asp Ile Val Leu Met Ala Gln Thr Leu Glu Lys Ile Phe Leu Gln Lys
                165                 170                 175

Val Ala Ser Met Pro Gln Glu Glu Gln Glu Leu Val Val Thr Ile Pro
                180                 185                 190
```

-continued

```
Lys Asn Ser His Lys Lys Gly Ala Lys Leu Ala Ala Leu Gln Gly Ser
        195                 200                 205
Val Thr Ser Ala His Gln Val Pro Ala Val Ser Ser Val Ser His Thr
    210                 215                 220
Ala Leu Tyr Thr Pro Pro Glu Ile Pro Thr Thr Val Leu Asn Ile
225                 230                 235                 240
Pro His Pro Ser Val Ile Ser Ser Pro Leu Leu Lys Ser Leu His Ser
                245                 250                 255
Ala Gly Pro Pro Leu Leu Ala Val Thr Ala Ala Pro Pro Ala Gln Pro
            260                 265                 270
Leu Ala Lys Lys Lys Gly Val Lys Arg Lys Ala Asp Thr Thr Thr Pro
        275                 280                 285
Thr Pro Thr Ala Ile Leu Ala Pro Gly Ser Pro Ala Ser Pro Pro Gly
    290                 295                 300
Ser Leu Glu Pro Lys Ala Ala Arg Leu Pro Pro Met Arg Arg Glu Ser
305                 310                 315                 320
Gly Arg Pro Ile Lys Pro Pro Arg Lys Asp Leu Pro Asp Ser Gln Gln
                325                 330                 335
Gln His Gln Ser Ser Lys Lys Gly Lys Leu Ser Glu Gln Leu Lys His
            340                 345                 350
Cys Asn Gly Ile Leu Lys Glu Leu Leu Ser Lys Lys His Ala Ala Tyr
        355                 360                 365
Ala Trp Pro Phe Tyr Lys Pro Val Asp Ala Ser Ala Leu Gly Leu His
    370                 375                 380
Asp Tyr His Asp Ile Ile Lys His Pro Met Asp Leu Ser Thr Val Lys
385                 390                 395                 400
Arg Lys Met Glu Asn Arg Asp Tyr Arg Asp Ala Gln Glu Phe Ala Ala
                405                 410                 415
Asp Val Arg Leu Met Phe Ser Asn Cys Tyr Lys Tyr Asn Pro Pro Asp
            420                 425                 430
His Asp Val Val Ala Met Ala Arg Lys Leu Gln Asp Val Phe Glu Phe
        435                 440                 445
Arg Tyr Ala Lys Met Pro Asp Glu Pro Leu Glu Pro Gly Pro Leu Pro
    450                 455                 460
Val Ser Thr Ala Met Pro Pro Gly Leu Ala Lys Ser Ser Ser Glu Ser
465                 470                 475                 480
Ser Ser Glu Glu Ser Ser Ser Glu Ser Ser Glu Glu Glu Glu Glu
                485                 490                 495
Glu Asp Glu Glu Asp Glu Glu Glu Ser Glu Ser Ser Asp Ser
            500                 505                 510
Glu Glu Glu Arg Ala His Arg Leu Ala Glu Leu Gln Glu Gln Leu Arg
        515                 520                 525
Ala Val His Glu Gln Leu Ala Ala Leu Ser Gln Gly Pro Ile Ser Lys
    530                 535                 540
Pro Lys Arg Lys Arg Glu Lys Glu Lys Lys Lys Arg Lys Ala
545                 550                 555                 560
Glu Lys His Arg Gly Arg Ala Gly Ala Asp Glu Asp Lys Gly Pro
                565                 570                 575
Arg Ala Pro Arg Pro Pro Gln Pro Lys Lys Ser Lys Lys Ala Ser Gly
            580                 585                 590
Ser Gly Gly Gly Ser Ala Ala Leu Gly Pro Ser Gly Phe Gly Pro Ser
        595                 600                 605
```

-continued

```
Gly Gly Ser Gly Thr Lys Leu Pro Lys Lys Ala Thr Lys Thr Ala Pro
            610                 615                 620
Pro Ala Leu Pro Thr Gly Tyr Asp Ser Glu Glu Glu Glu Ser Arg
625                 630                 635                 640
Pro Met Ser Tyr Asp Glu Lys Arg Gln Leu Ser Leu Asp Ile Asn Lys
                    645                 650                 655
Leu Pro Gly Glu Lys Leu Gly Arg Val Val His Ile Ile Gln Ala Arg
                660                 665                 670
Glu Pro Ser Leu Arg Asp Ser Asn Pro Glu Glu Ile Glu Ile Asp Phe
            675                 680                 685
Glu Thr Leu Lys Pro Ser Thr Leu Arg Glu Leu Glu Arg Tyr Val Leu
        690                 695                 700
Ser Cys Leu Arg Lys Lys Pro Arg Lys Pro Tyr Thr Ile Lys Lys Pro
705                 710                 715                 720
Val Gly Lys Thr Lys Glu Glu Leu Ala Leu Glu Lys Lys Arg Glu Leu
                    725                 730                 735
Glu Lys Arg Leu Gln Asp Val Ser Gly Gln Leu Asn Ser Thr Lys Lys
                740                 745                 750
Pro Pro Lys Lys Ala Asn Glu Lys Thr Glu Ser Ser Ala Gln Gln
            755                 760                 765
Val Ala Val Ser Arg Leu Ser Ala Ser Ser Ser Ser Asp Ser Ser
        770                 775                 780
Ser Ser Ser Ser Ser Ser Ser Ser Asp Thr Ser Asp Ser Asp Ser
785                 790                 795                 800
Gly

<210> SEQ ID NO 2
<211> LENGTH: 726
<212> TYPE: PRT
<213> ORGANISM: Homo sapiens

<400> SEQUENCE: 2

Met Ser Thr Ala Thr Val Ala Pro Ala Gly Ile Pro Ala Thr Pro
  1               5                  10                  15
Gly Pro Val Asn Pro Pro Pro Glu Val Ser Asn Pro Ser Lys Pro
                 20                  25                  30
Gly Arg Lys Thr Asn Gln Leu Gln Tyr Met Gln Asn Val Val Lys
             35                  40                  45
Thr Leu Trp Lys His Gln Phe Ala Trp Pro Phe Tyr Gln Pro Val Asp
 50                  55                  60
Ala Ile Lys Leu Asn Leu Pro Asp Tyr His Lys Ile Ile Lys Asn Pro
 65                  70                  75                  80
Met Asp Met Gly Thr Ile Lys Lys Arg Leu Glu Asn Asn Tyr Tyr Trp
                     85                  90                  95
Ser Ala Ser Glu Cys Met Gln Asp Phe Asn Thr Met Phe Thr Asn Cys
                100                 105                 110
Tyr Ile Tyr Asn Lys Pro Thr Asp Asp Ile Val Leu Met Ala Gln Ala
            115                 120                 125
Leu Glu Lys Ile Phe Leu Gln Lys Val Ala Gln Met Pro Gln Glu Glu
        130                 135                 140
Val Glu Leu Leu Pro Pro Ala Pro Lys Gly Lys Gly Arg Lys Pro Ala
145                 150                 155                 160
Ala Gly Ala Gln Ser Ala Gly Thr Gln Gln Val Ala Val Ser Ser
                    165                 170                 175
```

```
Val Ser Pro Ala Thr Pro Phe Gln Ser Val Pro Pro Thr Val Ser Gln
                180                 185                 190

Thr Pro Val Ile Ala Ala Thr Pro Val Pro Thr Ile Thr Ala Asn Val
            195                 200                 205

Thr Ser Val Pro Val Pro Pro Ala Ala Pro Pro Pro Ala Thr
210                 215                 220

Pro Ile Val Pro Val Val Pro Pro Thr Pro Pro Val Val Lys Lys Lys
225                 230                 235                 240

Gly Val Lys Arg Lys Ala Asp Thr Thr Thr Pro Thr Thr Ser Ala Ile
                245                 250                 255

Thr Ala Ser Arg Ser Glu Ser Pro Pro Pro Leu Ser Asp Pro Lys Gln
            260                 265                 270

Ala Lys Val Val Ala Arg Arg Glu Ser Gly Gly Arg Pro Ile Lys Pro
        275                 280                 285

Pro Lys Lys Asp Leu Glu Asp Gly Glu Val Pro Gln His Ala Gly Lys
    290                 295                 300

Lys Gly Lys Leu Ser Glu His Leu Arg Tyr Cys Asp Ser Ile Leu Arg
305                 310                 315                 320

Glu Met Leu Ser Lys Lys His Ala Ala Tyr Ala Trp Pro Phe Tyr Lys
                325                 330                 335

Pro Val Asp Ala Glu Ala Leu Glu Leu His Asp Tyr His Asp Ile Ile
            340                 345                 350

Lys His Pro Met Asp Leu Ser Thr Val Lys Arg Lys Met Asp Gly Arg
        355                 360                 365

Glu Tyr Pro Asp Ala Gln Gly Phe Ala Ala Asp Val Arg Leu Met Phe
    370                 375                 380

Ser Asn Cys Tyr Lys Tyr Asn Pro Pro Asp His Glu Val Val Ala Met
385                 390                 395                 400

Ala Arg Lys Leu Gln Asp Val Phe Glu Met Arg Phe Ala Lys Met Pro
                405                 410                 415

Asp Glu Pro Val Glu Ala Pro Ala Leu Pro Ala Pro Ala Ala Pro Met
            420                 425                 430

Val Ser Lys Gly Ala Glu Ser Ser Arg Ser Ser Glu Glu Ser Ser Ser
        435                 440                 445

Asp Ser Gly Ser Ser Asp Ser Glu Glu Glu Arg Ala Thr Arg Leu Ala
    450                 455                 460

Glu Leu Gln Glu Gln Leu Lys Ala Val His Glu Gln Leu Ala Ala Leu
465                 470                 475                 480

Ser Gln Ala Pro Val Asn Lys Pro Lys Lys Lys Lys Glu Lys Lys Glu
                485                 490                 495

Lys Glu Lys Lys Lys Lys Asp Lys Glu Lys Glu Lys Glu Lys His Lys
            500                 505                 510

Val Lys Ala Glu Glu Lys Lys Ala Lys Val Ala Pro Pro Ala Lys
        515                 520                 525

Gln Ala Gln Gln Lys Lys Ala Pro Ala Lys Lys Ala Asn Ser Thr Thr
    530                 535                 540

Thr Ala Gly Arg Gln Leu Lys Lys Gly Gly Lys Gln Ala Ser Ala Ser
545                 550                 555                 560

Tyr Asp Ser Glu Glu Glu Glu Gly Leu Pro Met Ser Tyr Asp Glu
                565                 570                 575

Lys Arg Gln Leu Ser Leu Asp Ile Asn Arg Leu Pro Gly Glu Lys Leu
            580                 585                 590

Gly Arg Val Val His Ile Ile Gln Ser Arg Glu Pro Ser Leu Arg Asp
```

```
                595                 600                 605
Ser Asn Pro Asp Glu Ile Glu Ile Asp Phe Glu Thr Leu Lys Pro Thr
610                 615                 620

Thr Leu Arg Glu Leu Glu Arg Tyr Val Lys Ser Cys Leu Gln Lys Lys
625                 630                 635                 640

Gln Arg Lys Pro Phe Ser Ala Ser Gly Lys Gln Ala Ala Lys Ser
                645                 650                 655

Lys Glu Glu Leu Ala Gln Glu Lys Lys Lys Glu Leu Glu Lys Arg Leu
                660                 665                 670

Gln Asp Val Ser Gly Gln Leu Ser Ser Lys Lys Pro Ala Arg Lys
                675                 680                 685

Glu Lys Pro Gly Ser Ala Pro Ser Gly Gly Pro Ser Arg Leu Ser Ser
690                 695                 700

Ser Ser Ser Ser Glu Ser Gly Ser Ser Ser Ser Gly Ser Ser Ser
705                 710                 715                 720

Asp Ser Ser Asp Ser Glu
                725

<210> SEQ ID NO 3
<211> LENGTH: 722
<212> TYPE: PRT
<213> ORGANISM: Homo sapiens

<400> SEQUENCE: 3

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
                20                  25                  30

Ala Gln Pro Gln Pro Ala Asn Ala Ala Ser Thr Asn Pro Pro Pro
            35                  40                  45

Glu Thr Ser Asn Pro Asn Lys Pro Lys Arg Gln Thr Asn Gln Leu Gln
50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
                85                  90                  95

Tyr Tyr Lys Ile Ile Lys Thr Pro Met Asp Met Gly Thr Ile Lys Lys
                100                 105                 110

Arg Leu Glu Asn Asn Tyr Tyr Trp Asn Ala Gln Glu Cys Ile Gln Asp
                115                 120                 125

Phe Asn Thr Met Phe Thr Asn Cys Tyr Ile Tyr Asn Lys Pro Gly Asp
                130                 135                 140

Asp Ile Val Leu Met Ala Glu Ala Leu Glu Lys Leu Phe Leu Gln Lys
145                 150                 155                 160

Ile Asn Glu Leu Pro Thr Glu Glu Thr Glu Ile Met Ile Val Gln Ala
                165                 170                 175

Lys Gly Arg Gly Arg Gly Arg Lys Glu Thr Gly Thr Ala Lys Pro Gly
                180                 185                 190

Val Ser Thr Val Pro Asn Thr Thr Gln Ala Ser Thr Pro Pro Gln Thr
            195                 200                 205

Gln Thr Pro Gln Pro Asn Pro Pro Val Gln Ala Thr Pro His Pro
                210                 215                 220

Phe Pro Ala Val Thr Pro Asp Leu Ile Val Gln Thr Pro Val Met Thr
225                 230                 235                 240
```

```
Val Val Pro Pro Gln Pro Leu Gln Thr Pro Pro Val Pro Pro Gln
            245                 250                 255

Pro Gln Pro Pro Ala Pro Ala Pro Gln Pro Val Gln Ser His Pro
        260                 265                 270

Pro Ile Ile Ala Ala Thr Pro Gln Pro Val Lys Thr Lys Gly Val
            275                 280                 285

Lys Arg Lys Ala Asp Thr Thr Thr Pro Thr Thr Ile Asp Pro Ile His
290                 295                 300

Glu Pro Pro Ser Leu Pro Glu Pro Lys Thr Thr Lys Leu Gly Gln
305                 310                 315                 320

Arg Arg Glu Ser Ser Arg Pro Val Lys Pro Pro Lys Lys Asp Val Pro
                325                 330                 335

Asp Ser Gln Gln His Pro Ala Pro Glu Lys Ser Ser Lys Val Ser Glu
            340                 345                 350

Gln Leu Lys Cys Cys Ser Gly Ile Leu Lys Glu Met Phe Ala Lys Lys
        355                 360                 365

His Ala Ala Tyr Ala Trp Pro Phe Tyr Lys Pro Val Asp Val Glu Ala
    370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                405                 410                 415

Glu Phe Gly Ala Asp Val Arg Leu Met Phe Ser Asn Cys Tyr Lys Tyr
            420                 425                 430

Asn Pro Pro Asp His Glu Val Val Ala Met Ala Arg Lys Leu Gln Asp
        435                 440                 445

Val Phe Glu Met Arg Phe Ala Lys Met Pro Asp Glu Pro Glu Glu Pro
    450                 455                 460

Val Val Ala Val Ser Ser Pro Ala Val Pro Pro Thr Lys Val Val
465                 470                 475                 480

Ala Pro Pro Ser Ser Ser Asp Ser Ser Ser Asp Ser Ser Ser Asp Ser
                485                 490                 495

Asp Ser Ser Thr Asp Asp Ser Glu Glu Glu Arg Ala Gln Arg Leu Ala
            500                 505                 510

Glu Leu Gln Glu Gln Leu Lys Ala Val His Glu Gln Leu Ala Ala Leu
        515                 520                 525

Ser Gln Pro Gln Gln Asn Lys Pro Lys Lys Lys Glu Lys Asp Lys Lys
    530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Lys Lys Thr Lys Lys Asn
                565                 570                 575

Asn Ser Ser Asn Ser Asn Val Ser Lys Lys Glu Pro Ala Pro Met Lys
            580                 585                 590

Ser Lys Pro Pro Thr Tyr Glu Ser Glu Glu Asp Lys Cys Lys
        595                 600                 605

Pro Met Ser Tyr Glu Glu Lys Arg Gln Leu Ser Leu Asp Ile Asn Lys
    610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
```

```
                    660                 665                 670
Ser Cys Leu Arg Lys Arg Lys Pro Gln Ala Glu Lys Val Asp Val
            675                 680                 685

Ile Ala Gly Ser Ser Lys Met Lys Gly Phe Ser Ser Ser Glu Ser Glu
            690                 695                 700

Ser Ser Ser Glu Ser Ser Ser Asp Ser Glu Asp Ser Glu Thr Gly
705                 710                 715                 720

Pro Ala

<210> SEQ ID NO 4
<211> LENGTH: 947
<212> TYPE: PRT
<213> ORGANISM: Homo sapiens

<400> SEQUENCE: 4

Met Ser Leu Pro Ser Arg Gln Thr Ala Ile Ile Val Asn Pro Pro
  1               5                  10                  15

Pro Glu Tyr Ile Asn Thr Lys Lys Asn Gly Arg Leu Thr Asn Gln Leu
                 20                  25                  30

Gln Tyr Leu Gln Lys Val Val Leu Lys Asp Leu Trp Lys His Ser Phe
             35                  40                  45

Ser Trp Pro Phe Gln Arg Pro Val Asp Ala Val Lys Leu Gln Leu Pro
 50                  55                  60

Asp Tyr Tyr Thr Ile Ile Lys Asn Pro Met Asp Leu Asn Thr Ile Lys
 65                  70                  75                  80

Lys Arg Leu Glu Asn Lys Tyr Tyr Ala Lys Ala Ser Glu Cys Ile Glu
                 85                  90                  95

Asp Phe Asn Thr Met Phe Ser Asn Cys Tyr Leu Tyr Asn Lys Pro Gly
                100                 105                 110

Asp Asp Ile Val Leu Met Ala Gln Ala Leu Glu Lys Leu Phe Met Gln
            115                 120                 125

Lys Leu Ser Gln Met Pro Gln Glu Glu Gln Val Val Gly Val Lys Glu
130                 135                 140

Arg Ile Lys Lys Gly Thr Gln Gln Asn Ile Ala Val Ser Ser Ala Lys
145                 150                 155                 160

Glu Lys Ser Ser Pro Ser Ala Thr Glu Lys Val Phe Lys Gln Gln Glu
                165                 170                 175

Ile Pro Ser Val Phe Pro Lys Thr Ser Ile Ser Pro Leu Asn Val Val
            180                 185                 190

Gln Gly Ala Ser Val Asn Ser Ser Ser Gln Thr Ala Ala Gln Val Thr
        195                 200                 205

Lys Gly Val Lys Arg Lys Ala Asp Thr Thr Thr Pro Ala Thr Ser Ala
210                 215                 220

Val Lys Ala Ser Ser Glu Phe Ser Pro Thr Phe Thr Glu Lys Ser Val
225                 230                 235                 240

Ala Leu Pro Pro Ile Lys Glu Asn Met Pro Lys Asn Val Leu Pro Asp
                245                 250                 255

Ser Gln Gln Gln Tyr Asn Val Val Lys Thr Val Lys Val Thr Glu Gln
            260                 265                 270

Leu Arg His Cys Ser Glu Ile Leu Lys Glu Met Leu Ala Lys Lys His
        275                 280                 285

Phe Ser Tyr Ala Trp Pro Phe Tyr Asn Pro Val Asp Val Asn Ala Leu
290                 295                 300

Gly Leu His Asn Tyr Tyr Asp Val Val Lys Asn Pro Met Asp Leu Gly
```

```
            305                 310                 315                 320
        Thr Ile Lys Glu Lys Met Asp Asn Gln Glu Tyr Lys Asp Ala Tyr Lys
                        325                 330                 335

Phe Ala Ala Asp Val Arg Leu Met Phe Met Asn Cys Tyr Lys Tyr Asn
                        340                 345                 350

Pro Pro Asp His Glu Val Val Thr Met Ala Arg Met Leu Gln Asp Val
                        355                 360                 365

Phe Glu Thr His Phe Ser Lys Ile Pro Ile Glu Pro Val Glu Ser Met
                370                 375                 380

Pro Leu Cys Tyr Ile Lys Thr Asp Ile Thr Glu Thr Thr Gly Arg Glu
        385                 390                 395                 400

Asn Thr Asn Glu Ala Ser Ser Glu Gly Asn Ser Ser Asp Ser Glu
                        405                 410                 415

Asp Glu Arg Val Lys Arg Leu Ala Lys Leu Gln Glu Gln Leu Lys Ala
                        420                 425                 430

Val His Gln Gln Leu Gln Val Leu Ser Gln Val Pro Phe Arg Lys Leu
                        435                 440                 445

Asn Lys Lys Lys Glu Lys Ser Lys Glu Lys Lys Glu Lys Val
                450                 455                 460

Asn Asn Ser Asn Glu Asn Pro Arg Lys Met Cys Glu Gln Met Arg Leu
        465                 470                 475                 480

Lys Glu Lys Ser Lys Arg Asn Gln Pro Lys Arg Lys Gln Gln Phe
                        485                 490                 495

Ile Gly Leu Lys Ser Glu Asp Glu Asp Asn Ala Lys Pro Met Asn Tyr
                        500                 505                 510

Asp Glu Lys Arg Gln Leu Ser Leu Asn Ile Asn Lys Leu Pro Gly Asp
                        515                 520                 525

Lys Leu Gly Arg Val Val His Ile Ile Gln Ser Arg Glu Pro Ser Leu
                        530                 535                 540

Ser Asn Ser Asn Pro Asp Glu Ile Glu Ile Asp Phe Glu Thr Leu Lys
        545                 550                 555                 560

Ala Ser Thr Leu Arg Glu Leu Glu Lys Tyr Val Ser Ala Cys Leu Arg
                        565                 570                 575

Lys Arg Pro Leu Lys Pro Ala Lys Lys Ile Met Met Ser Lys Glu
                        580                 585                 590

Glu Leu His Ser Gln Lys Lys Gln Glu Leu Glu Lys Arg Leu Leu Asp
                        595                 600                 605

Val Asn Asn Gln Leu Asn Ser Arg Lys Arg Gln Thr Lys Ser Asp Lys
                        610                 615                 620

Thr Gln Pro Ser Lys Ala Val Glu Asn Val Ser Arg Leu Ser Glu Ser
        625                 630                 635                 640

Ser Ser Ser Ser Ser Ser Ser Glu Ser Ser Ser Ser Ser Asp
                        645                 650                 655

Leu Ser Ser Asp Ser Ser Asp Ser Glu Ser Glu Met Phe Pro Lys
                        660                 665                 670

Phe Thr Glu Val Lys Pro Asn Asp Ser Pro Ser Lys Glu Asn Val Lys
                        675                 680                 685

Lys Met Lys Asn Glu Cys Ile Leu Pro Glu Gly Arg Thr Gly Val Thr
                        690                 695                 700

Gln Ile Gly Tyr Cys Val Gln Asp Thr Thr Ser Ala Asn Thr Thr Leu
        705                 710                 715                 720

Val His Gln Thr Thr Pro Ser His Val Met Pro Pro Asn His His Gln
                        725                 730                 735
```

Leu Ala Phe Asn Tyr Gln Glu Leu Glu His Leu Gln Thr Val Lys Asn
            740                 745                 750

Ile Ser Pro Leu Gln Ile Leu Pro Pro Ser Gly Asp Ser Glu Gln Leu
            755                 760                 765

Ser Asn Gly Ile Thr Val Met His Pro Ser Gly Asp Ser Asp Thr Thr
770                 775                 780

Met Leu Glu Ser Glu Cys Gln Ala Pro Val Gln Lys Asp Ile Lys Ile
785                 790                 795                 800

Lys Asn Ala Asp Ser Trp Lys Ser Leu Gly Lys Pro Val Lys Pro Ser
            805                 810                 815

Gly Val Met Lys Ser Ser Asp Glu Leu Phe Asn Gln Phe Arg Lys Ala
            820                 825                 830

Ala Ile Glu Lys Glu Val Lys Ala Arg Thr Gln Glu Leu Ile Arg Lys
            835                 840                 845

His Leu Glu Gln Asn Thr Lys Glu Leu Lys Ala Ser Gln Glu Asn Gln
        850                 855                 860

Arg Asp Leu Gly Asn Gly Leu Thr Val Glu Ser Phe Ser Asn Lys Ile
865                 870                 875                 880

Gln Asn Lys Cys Ser Gly Glu Glu Gln Lys His Gln Gln Ser Ser
            885                 890                 895

Glu Ala Gln Asp Lys Ser Lys Leu Trp Leu Leu Lys Asp Arg Asp Leu
            900                 905                 910

Ala Arg Gln Lys Glu Gln Glu Arg Arg Arg Glu Ala Met Val Gly
            915                 920                 925

Thr Ile Asp Met Thr Leu Gln Ser Asp Ile Met Thr Met Phe Glu Asn
            930                 935                 940

Asn Phe Asp
945

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
tggagaagca tttgggtatc tactc                                    25

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
aagacggcat gctcaacaca                                          20

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
gagtgaggcc cagcatatgt c                                        21

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
cctctggatt ttctgagttg ca                                              22

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gctttgggac tccacaacta ctatg                                           25

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
gattgtccat tttccccttg atc                                             23

<210> SEQ ID NO 11
<211> LENGTH: 19
<212> TYPE: DNA
<213> ORGANISM: Artificial Sequence
<220> FEATURE:
<223> OTHER INFORMATION: Synthetic primer

<400> SEQUENCE: 11
tttccccaat gctggttga                                                  19

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
aaccaaaatc cgttgcttcc t                                               21

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
gctgattcct gaggcccttt                                                 20

<210> SEQ ID NO 14
<211> LENGTH: 18
<212> TYPE: DNA
<213> ORGANISM: Artificial Sequence
<220> FEATURE:
<223> OTHER INFORMATION: Synthetic primer

```
<400> SEQUENCE: 14
cagggcagca agggacat                                                 18

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
cgccaacaga gaaacaacat ttag                                          24

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
ccaaccagga ttcggatctt t                                             21

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
cctcccgttt gttctcaact tg                                            22

<210> SEQ ID NO 18
<211> LENGTH: 23
<212> TYPE: DNA
<213> ORGANISM: Artificial Sequence
<220> FEATURE:
<223> OTHER INFORMATION: Synthetic primer

<400> SEQUENCE: 18
ggtgcatagc ctgttcctta ttg                                           23

<210> SEQ ID NO 19
<211> LENGTH: 23
<212> TYPE: DNA
<213> ORGANISM: Artificial Sequence
<220> FEATURE:
<223> OTHER INFORMATION: Synthetic primer

<400> SEQUENCE: 19
tgcacagaat agcaagtcca tca                                           23

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
tgtggcgaga tgctcttgaa                                               20
```